US010056549B2

(12) United States Patent
Montenegro et al.

(10) Patent No.: US 10,056,549 B2
(45) Date of Patent: Aug. 21, 2018

(54) COMPOUNDS FOR ELECTRONIC DEVICES

(75) Inventors: Elvira Montenegro, Weinheim (DE); Arne Buesing, Frankfurt am Main (DE); Frank Voges, Bad Duerkheim (DE); Christof Pflumm, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 930 days.

(21) Appl. No.: 14/115,118

(22) PCT Filed: Apr. 14, 2012

(86) PCT No.: PCT/EP2012/001624
§ 371 (c)(1),
(2), (4) Date: Nov. 1, 2013

(87) PCT Pub. No.: WO2012/150001
PCT Pub. Date: Nov. 8, 2012

(65) Prior Publication Data
US 2014/0061548 A1 Mar. 6, 2014

(30) Foreign Application Priority Data

May 5, 2011 (EP) ..................................... 11003705
Aug. 31, 2011 (EP) ..................................... 11007067

(51) Int. Cl.
H01L 51/00 (2006.01)
C09B 57/00 (2006.01)
C09B 57/10 (2006.01)
C07D 219/04 (2006.01)
C07D 221/20 (2006.01)
C07D 405/04 (2006.01)
C07D 409/04 (2006.01)
C07D 413/04 (2006.01)
C07D 265/38 (2006.01)

(52) U.S. Cl.
CPC ........ *H01L 51/0036* (2013.01); *C07D 219/04* (2013.01); *C07D 221/20* (2013.01); *C07D 265/38* (2013.01); *C07D 405/04* (2013.01); *C07D 409/04* (2013.01); *C07D 413/04* (2013.01); *C09B 57/00* (2013.01); *C09B 57/10* (2013.01); *H01L 51/0035* (2013.01); *H01L 51/0052* (2013.01); *H01L 51/0059* (2013.01); *H01L 51/0071* (2013.01); *H01L 51/0072* (2013.01); *H01L 51/0073* (2013.01); *H01L 51/0074* (2013.01); *H01L 51/0085* (2013.01); *H01L 51/0087* (2013.01); *Y02E 10/549* (2013.01)

(58) Field of Classification Search
CPC ...................................... C07D 219/00–219/16
See application file for complete search history.

(56) References Cited

U.S. PATENT DOCUMENTS

| 4,561,001 | A | 12/1985 | Gunn et al. |
| 9,458,182 | B2 | 10/2016 | Langer et al. |
| 2007/0290610 | A1 | 12/2007 | Park et al. |
| 2008/0008907 | A1 | 1/2008 | Cho et al. |
| 2008/0079356 | A1 | 4/2008 | Park et al. |
| 2008/0100207 | A1 | 5/2008 | Park et al. |
| 2008/0122346 | A1 | 5/2008 | Lyu et al. |
| 2009/0026928 | A1 | 1/2009 | Park et al. |
| 2010/0096982 | A1 | 4/2010 | Eum et al. |
| 2010/0171417 | A1* | 7/2010 | Kitamura ............. C07D 401/10 313/504 |
| 2011/0108820 | A1 | 5/2011 | Kobayashi |
| 2011/0266533 | A1 | 11/2011 | Buesing et al. |
| 2011/0309341 | A1 | 12/2011 | Ohuchi et al. |
| 2012/0168730 | A1 | 7/2012 | Kim et al. |
| 2012/0211729 | A1 | 8/2012 | Yamauchi |
| 2013/0075715 | A1 | 3/2013 | Yokoyama et al. |
| 2014/0042425 | A1 | 2/2014 | Yokoyama et al. |
| 2014/0070146 | A1 | 3/2014 | Parham et al. |

FOREIGN PATENT DOCUMENTS

| JP | 61-044955 A | 3/1986 |
| JP | 10-310574 A | 11/1998 |
| JP | 2007-332139 A | 12/2007 |
| JP | 2009-029807 A | 2/2009 |
| JP | 2010-045301 A | 2/2010 |
| JP | 2010-059158 A | 3/2010 |
| JP | 2010272618 A | 12/2010 |
| JP | 2011049546 A | 3/2011 |

(Continued)

OTHER PUBLICATIONS

New Ambipolar Organic Semiconductors. 2. Effects of Electron Acceptor Strength on Intramolecular Charge Transfer Photophysics, Highly Efficient Electroluminescence, and Field-Effect Charge Transport of Phenoxazine-Based Donor-Acceptor Materials Chem. Mater., 2008, 20 (13), pp. 4212-4223.*
U.S. Appl. No. 14/115,107.
International Preliminary Report on Patentability for PCT/EP2012/001624, dated Nov. 5, 2013.
Nowakowska-Oleksy et al., "Phenoxazine Based Units—Synthesis, Photophysics and Electrochemistry", Journal of Fluorescence, vol. 21, pp. 169-178 (2011).
Memminger et al., "Phenothiazinophanes: Synthesis, Structure, and Intramolecular Electronic Communication", Organic Letters, vol. 10, No. 13, pp. 2797-2800 (2008).
Bronger et al., "Influence of the Bite Angle on the Hydroformylation of Internal Olefins to Linear Aldehydes", Organometallics, vol. 22, pp. 5358-5369 (2003).
International Search Report for PCT/EP2012/001624 dated Jul. 20, 2012.

(Continued)

*Primary Examiner* — Alex A Rolland
(74) *Attorney, Agent, or Firm* — Drinker Biddle & Reath LLP

(57) ABSTRACT

The present invention relates to a compound of the formula (I), to the use of the compound in an electronic device, and to an electronic device comprising a compound of the formula (I). The present invention furthermore relates to a process for the preparation of a compound of the formula (I) and to a formulation comprising one or more compounds of the formula (I).

17 Claims, No Drawings

(56) References Cited

FOREIGN PATENT DOCUMENTS

| | | |
|---|---|---|
| JP | 2011-071452 A | 4/2011 |
| JP | 2011-178742 A | 9/2011 |
| JP | 2011-210749 A | 10/2011 |
| JP | 2012-059904 A | 3/2012 |
| KR | 20110111692 A | 10/2011 |
| KR | 20110113469 A | 10/2011 |
| KR | 20140026536 A | 3/2014 |
| WO | WO-2010001982 A1 | 1/2010 |
| WO | WO-2010050781 A1 | 5/2010 |
| WO | WO-2010058859 A1 | 5/2010 |
| WO | WO-2010/062107 A1 | 6/2010 |
| WO | WO-2010/083871 A1 | 7/2010 |
| WO | WO-201079051 A1 | 7/2010 |
| WO | WO-2010/114266 A2 | 10/2010 |
| WO | WO-2010/147319 A2 | 12/2010 |
| WO | WO-2011/155169 A1 | 12/2011 |
| WO | WO-2012/147330 A1 | 11/2012 |

OTHER PUBLICATIONS

Zhu, Y., et al., "New Ambipolar Organic Semiconductors. 1. Synthesis, Single-Crystal Structures, Redox Properties, and Photophysics of Pehnoxazine-Based Donor-Acceptor Molecules", Chemistry of Materials, 2008, vol. 20, No. 13, pp. 4200-4211.
English Translation of Korean Office Action for Korean Application No. 10-2013-7032237, dated Oct. 11, 2017.

* cited by examiner

COMPOUNDS FOR ELECTRONIC DEVICES

CROSS-REFERENCE TO RELATED APPLICATIONS

This application is a national stage application (under 35 U.S.C. § 371) of PCT/EP2012/001624, filed Apr. 14, 2012, which claims benefit of European application 11003705.8, filed May 5, 2011, and European application 11007067.9, filed Aug. 31, 2011.

The present invention relates to a compound of the formula (I), to the use of the compound in an electronic device, and to an electronic device comprising a compound of the formula (I). The present invention furthermore relates to a process for the preparation of a compound of the formula (I) and to compositions and to a formulation comprising one or more compounds of the formula (I).

The development of functional compounds for use in electronic devices is currently the subject of intensive research. The aim here is, in particular, the development of compounds with which improved properties of electronic devices in one or more relevant points can be achieved, such as, for example, power efficiency, lifetime or colour coordinates of the emitted light.

In accordance with the present invention, the term electronic device is taken to mean, inter alia, organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

Of particular interest is the provision of compounds for use in the last-mentioned electronic devices called OLEDs. The general structure and the functional principle of OLEDs are known to the person skilled in the art and are described, inter alia, in U.S. Pat. No. 4,539,507, U.S. Pat. No. 5,151,629, EP 0676461 and WO 1998/27136.

Further improvements are still necessary with respect to the performance data of OLEDs, in particular with a view to broad commercial use, for example in display devices or as light sources. Of particular importance in this connection are the lifetime, the efficiency and the operating voltage of the OLEDs and the colour values achieved. In particular in the case of blue-emitting OLEDs, there is potential for improvement with respect to the lifetime of the devices. In addition, it is desirable, for use as functional materials in electronic devices, for the compounds to have high thermal stability and a high glass-transition temperature and to be capable of sublimation without decomposition.

In this connection, there is, in particular, a need for alternative hole-transport materials. In hole-transport materials in accordance with the prior art, the voltage generally increases with the layer thickness of the hole-transport layer. In practice, a greater layer thickness of the hole-transport layer would frequently be desirable, but this often has the consequence of a higher operating voltage and worse performance data. In this connection, there is a need for novel hole-transport materials which have high charge-carrier mobility, enabling thicker hole-transport layers to be achieved with an only slight increase in the operating voltage.

The prior art discloses the use, in particular, of arylamine compounds and carbazole compounds as hole-transport materials for OLEDs.

The application WO 2010/083871 discloses the use of dihydroacridine derivatives which are substituted by one or more arylamino groups as functional materials in OLEDs, preferably as hole-transport and hole-injection materials.

Furthermore, the application WO 2011/107186 discloses the use of dihydroacridine derivatives which are substituted by one or more carbazole groups as functional materials in OLEDs, preferably as hole-transport and hole-injection materials.

Again furthermore, the application US 2010/0019658 discloses the use of dihydroacridine derivatives which carry aryl or heteroaryl groups as substituents of the methylene group of the dihydroacridine as functional materials in OLEDs.

However, there continues to be a need for alternative hole-transport and hole-injection materials for use in OLEDs. In particular, there is a need for materials with which the above-mentioned, highly desired improvements in the performance data and properties of OLEDs can be achieved.

There is likewise a need for alternative matrix materials for use in OLEDs and in other electronic devices. In particular, there is a need for matrix materials for phosphorescent dopants and for matrix materials for mixed-matrix systems, which preferably result in good efficiency, a long lifetime and a low operating voltage of the electronic devices.

The present invention is thus based on the technical object of providing compounds which are suitable for use in electronic devices, such as, for example, OLEDs, and which can be employed, in particular, as hole-transport materials and/or as matrix materials.

As part of the present invention, it has now been found that compounds of the formula (1) indicated below are highly suitable for the above-mentioned uses.

The invention thus relates to a compound of a formula (I)

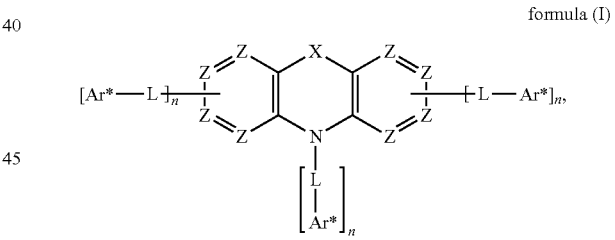

formula (I)

where the following applies to the symbols and indices occurring:

Ar* is on each occurrence, identically or differently, an aromatic ring system having 6 to 24 aromatic ring atoms or an electron-rich heteroaryl group having 5 to 18 aromatic ring atoms, each of which may be substituted by one or more radicals $R^2$;

L is on each occurrence, identically or differently, a single bond, C=O, C=$NR^2$, Si$(R^2)_2$, $PR^2$, P(=O)($R^2$), O, S, SO, $SO_2$, an alkylene group having 1 to 20 C atoms or an alkenylene or alkynylene group having 2 to 20 C atoms, where one or more $CH_2$ groups in the said groups may be replaced by C=O, C=$NR^2$, C=O—O, C=O—$NR^2$, Si$(R^2)_2$, $NR^2$, P(=O)($R^2$), O, S, SO or $SO_2$ and where one or more H atoms in the above-mentioned groups may be replaced by D, F, Cl, Br, I, CN or $NO_2$, or an aromatic ring system having 6 to 24 aromatic ring atoms, which may be substituted by one or more radicals $R^2$, or any desired combination of 1, 2, 3, 4 or 5 identical or different groups selected from the above-mentioned groups;

X is a divalent group selected from $C(R^1)_2$, $Si(R^1)_2$, $NR^1$, $PR^1$, O and S;

Z is on each occurrence, identically or differently, $CR^2$ or N if Z carries no substituents, and is equal to C if Z carries a substituent;

$R^1$ is on each occurrence, identically or differently, H, D, F, Cl, Br, I, $C(=O)R^3$, CN, $Si(R^3)_3$, $NO_2$, $P(=O)(R^3)_2$, $S(=O)R^3$, $S(=O)_2R^3$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^3$ and where one or more $CH_2$ groups in the above-mentioned groups may be replaced by $-R^3C=CR^3-$, $-C\equiv C-$, $Si(R^3)_2$, C=O, C=S, $C=NR^3$, $-C(=O)O-$, $-C(=O)NR^3-$, $NR^3$, $P(=O)(R^3)$, $-O-$, $-S-$, SO or $SO_2$ and where one or more H atoms in the above-mentioned groups may be replaced by D, F, Cl, Br, I, CN or $NO_2$, or an aromatic ring system having 6 to 30 aromatic ring atoms, which may in each case be substituted by one or more radicals $R^3$, where two or more non-aromatic radicals $R^1$ may be linked to one another and may form a ring;

$R^2$ is on each occurrence, identically or differently, H, D, F, Cl, Br, I, $C(=O)R^3$, CN, $Si(R^3)_3$, $NO_2$, $P(=O)(R^3)_2$, $S(=O)R^3$, $S(=O)_2R^3$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^3$ and where one or more $CH_2$ groups in the above-mentioned groups may be replaced by $-R^3C=CR^3-$, $-C\equiv C-$, $Si(R^3)_2$, C=O, C=S, $C=NR^3$, $-C(=O)O-$, $-C(=O)NR^3-$, $NR^3$, $P(=O)(R^3)$, $-O-$, $-S-$, SO or $SO_2$ and where one or more H atoms in the above-mentioned groups may be replaced by D, F, Cl, Br, I, CN or $NO_2$, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which may be substituted by one or more radicals $R^3$, where two or more radicals $R^2$ may be linked to one another and may form a ring;

$R^3$ is on each occurrence, identically or differently, H, D, F, Cl, Br, I, $C(=O)R^4$, CN, $Si(R^4)_3$, $NO_2$, $P(=O)(R^4)_2$, $S(=O)R^4$, $S(=O)_2R^4$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^4$ and where one or more $CH_2$ groups in the above-mentioned groups may be replaced by $-R^4C=CR^4-$, $-C\equiv C-$, $Si(R^4)_2$, C=O, C=S, $C=NR^4$, $-C(=O)O-$, $-C(=O)NR^4-$, $NR^4$, $P(=O)(R^4)$, $-O-$, $-S-$, SO or $SO_2$ and where one or more H atoms in the above-mentioned groups may be replaced by D, F, Cl, Br, I, CN or $NO_2$, or an aromatic or heteroaromatic ring system having 5 to 30 aromatic ring atoms, which may in each case be substituted by one or more radicals $R^4$, or an aryloxy or heteroaryloxy group having 5 to 30 aromatic ring atoms, which may be substituted by one or more radicals $R^4$, where two or more radicals $R^3$ may be linked to one another and may form a ring;

$R^4$ is on each occurrence, identically or differently, H, D, F or an aliphatic, aromatic or heteroaromatic organic radical having 1 to 20 C atoms, in which, in addition, one or more H atoms may be replaced by D or F; two or more substituents $R^4$ here may be linked to one another and may form a ring;

n is on each occurrence, identically or differently, 0 or 1, where at least two indices n must be equal to 1; for n=0, a group $R^2$ is bonded at the corresponding position;

where the compound does not contain a carbazole group; and where at least one group Ar* which represents an electron-rich heteroaryl group having 5 to 18 aromatic ring atoms or an aromatic ring system having 12 to 24 aromatic ring atoms must be present in the compound.

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp$^3$-hybridised C, Si, N or O atom, an sp$^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or CH$_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, nbutylthio, i-butylthio, s-butylthio, t-butylthio, n-pentylthio, s-pentylthio, nhexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present description, intended to be taken to mean, inter alia, that the two radicals are linked to one another by a chemical bond. This is illustrated by the following scheme:

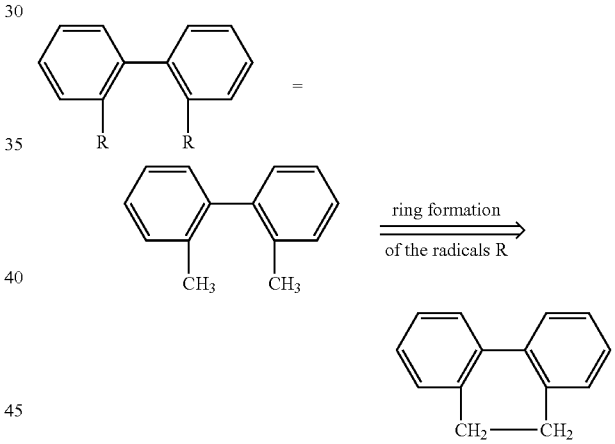

Furthermore, however, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

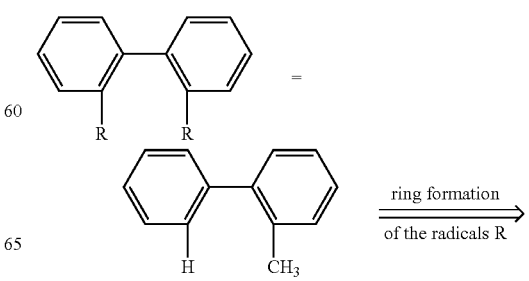

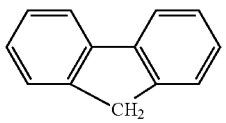

For clarification, it should be noted that the formulation "non-aromatic radicals" in the definition of $R^1$ relates to any types of aromatic groups, inter alia aryl groups and aromatic ring systems. This excludes, for example, the group X in the embodiment $C(R^1)_2$ or $Si(R^1)_2$ representing a spiro centre which is bonded to four aromatic rings, as is the case in a spirobifluorene derivative.

The term "electron-rich heteroaryl group" as embodiment of Ar* is, in accordance with the present invention, taken to mean a heteroaryl group, as defined above, which contains at least one heteroaromatic five-membered ring containing precisely one heteroatom, where carbazole derivatives are not taken to be electron-rich heteroaryl groups in accordance with the present invention. Carbazole derivatives in the sense of the present invention are also taken to mean carbazole derivatives with condensed-on groups, such as, for example, indenocarbazoles or indolocarbazoles, and carbazole derivatives in which one or more carbon atoms in the aromatic six-membered rings have been replaced by nitrogen.

Preferred electron-rich heteroaryl groups as groups Ar* in accordance with the present invention are compounds of the following formula (H)

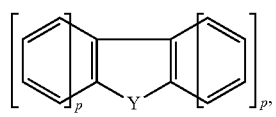

formula (H)

where
Y is selected from $NR^2$, $PR^2$, O and S; and
p is on each occurrence equal to 0 or 1, where, for p=0, radicals $R^2$ are bonded at the relevant positions, and where, for Y=$NR^2$, the two indices P cannot both be equal to 1;
the group is substituted by radicals $R^2$ at all free positions, and
the group may be connected to the group L at any desired position, where the bonding may also occur at the site of the bond $NR^2$ or $PR^2$.

Particular preference is given to groups of the formulae (H-1) to (H-5)

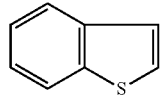

formula (H-1)

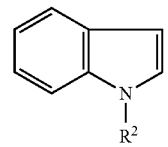

formula (H-2)

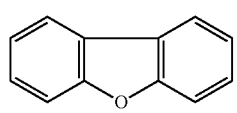

formula (H-3)

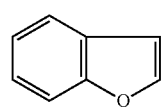

formula (H-4)

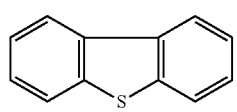

formula (H-5)

where the groups may be substituted by radicals $R^2$ at all free positions, and
the groups may be connected to the group L at any desired position, where the bonding make also occur at the site of the bond $NR^2$.

The groups of the formula (H-1) and (H-3) are connected to the group L in positions 1, 2, 3 or 4 of the dibenzothiophene or dibenzofuran basic structure.

Further embodiments according to the invention of the group Ar*, besides the electron-rich heteroaryl groups defined above, are aromatic ring systems containing 6 to 24 aromatic ring atoms, which may be substituted by one or more radicals $R^2$. Preference is given to aromatic ring systems which contain no condensed aryl groups having more than 14 aromatic ring atoms and particularly preferably those which contain no aryl groups having more than 10 aromatic ring atoms. Very particular preference is given to aromatic ring systems which comprise exclusively aryl groups having 6 aromatic ring atoms (=phenyl groups). Still more preferably, Ar* represents a phenyl group, a biphenyl group or a terphenyl group.

Preferred aromatic ring systems as groups Ar* are reproduced by the following formulae:

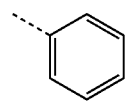

formula (A-1)

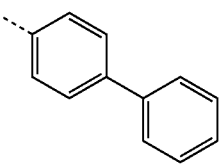

formula (A-2)

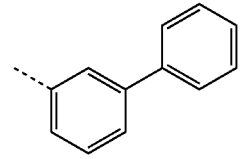

formula (A-3)

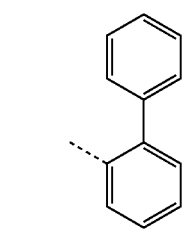

formula (A-4)

formula (A-5)
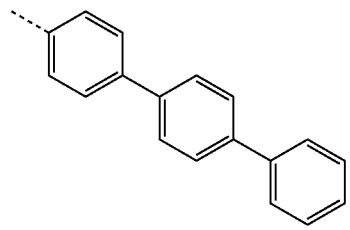
formula (A-6)
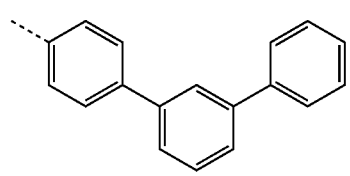
formula (A-7)
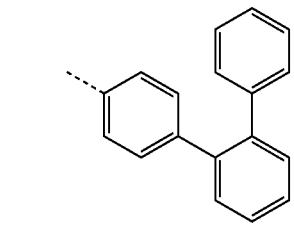
formula (A-8)
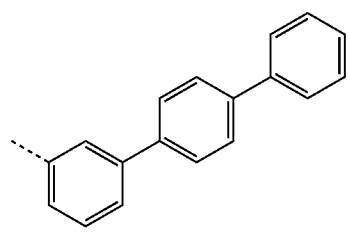
formula (A-9)
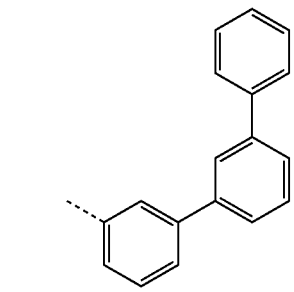
formula (A-10)
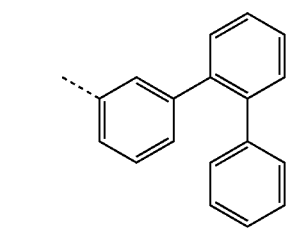
formula (A-11)
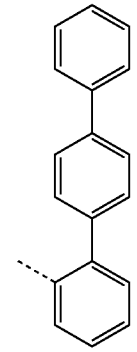
formula (A-12)
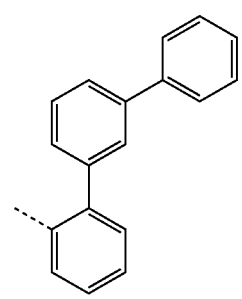
formula (A-13)
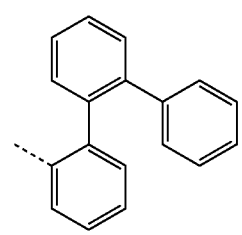
formula (A-14)
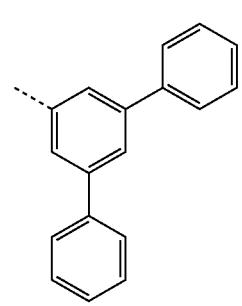
formula (A-15)
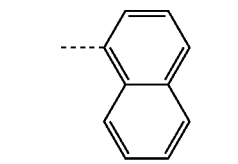
formula (A-16)
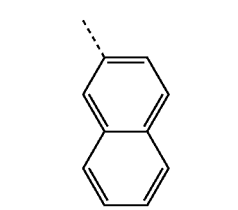

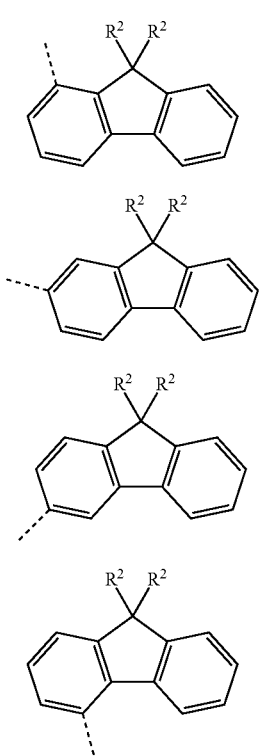

formula (A-17)

formula (A-18)

formula (A-19)

formula (A-20)

where the structures may be substituted by one or more radicals $R^2$, and $R^2$ is defined as indicated above.

The groups of the formula (A-1) to (A-14) are preferably substituted by a radical $R^2$ selected from F and an alkyl group having 1 to 10 C atoms, particularly preferably by a radical $R^2$ selected from F and an alkyl group having 1 to 5 C atoms, very particularly preferably by a radical selected from F and methyl, in at least one ortho-position of a phenyl group.

In a preferred embodiment of the invention, the group L is on each occurrence, identically or differently, a single bond, $Si(R^2)_2$, O, S, an alkylene group having 1 to 10 C atoms or an alkenylene or alkynylene group having 2 to 10 C atoms, where one or more $CH_2$ groups in the said groups may be replaced by $Si(R^2)_2$, O or S and where one or more H atoms in the said groups may be replaced by D, F or CN, or an aromatic ring system having 6 to 24 aromatic ring atoms, which may be substituted by one or more radicals $R^2$.

L is particularly preferably on each occurrence, identically or differently, a single bond or an aromatic ring system having 6 to 12 aromatic ring atoms, which may be substituted by one or more radicals $R^2$.

L is very particularly preferably a single bond.

According to a preferred embodiment, precisely one group L-Ar* is bonded to the nitrogen atom of the basic structure of the formula (I), and precisely one further group L-Ar* is bonded to the aromatic six-membered ring of the basic structure of the formula (I). This corresponds to an embodiment in which precisely two of the three indices n present in formula (I) are equal to 1 and precisely one of the indices n is equal to zero. According to a further preferred embodiment, all indices n are equal to 1, so that a group L-Ar* is bonded both to the nitrogen atom and also to the two aromatic six-membered rings of the basic structure of the formula (I).

It is furthermore preferred for the bonding position of the group L-Ar* to the aromatic six-membered ring of the basic structure of the formula (I) to be in the para- or meta-position to the nitrogen atom, particularly preferably in the para-position to the nitrogen atom.

It is preferred in accordance with the invention for L in the group L-Ar* which is bonded to the nitrogen atom to represent a single bond and for Ar* to represent an aromatic ring system having 6 to 24 aromatic ring atoms, which may be substituted by one or more radicals $R^2$. Ar* is in this case particularly preferably an aromatic ring system having 6 to 18 aromatic ring atoms, very particularly preferably an aromatic ring system having 12 to 18 aromatic ring atoms, which may be substituted by one or more radicals $R^2$.

It is furthermore preferred in accordance with the invention for X to be selected from $C(R^1)_2$, O and S. X is particularly preferably equal to $C(R^1)_2$.

Further preferably, a maximum of one group Z per aromatic six-membered ring of the basic structure of the formula (I) is equal to N. Particularly preferably, no group Z is equal to N, so that all groups Z are equal to C if a substituent is bonded, and are equal to $CR^2$ if no substituent is bonded.

According to a preferred embodiment, $R^1$ is on each occurrence, identically or differently, H, D, F, a straight-chain alkyl, alkoxy or thioalkyl group having 1 to 10 C atoms or a branched or cyclic alkyl, alkoxy or thioalkyl group having 3 to 10 C atoms or an alkenyl or alkynyl group having 2 to 10 C atoms, where the above-mentioned groups may each be substituted by one or more radicals $R^3$ and where one or more $CH_2$ groups in the above-mentioned groups may be replaced by $Si(R^3)_2$, O or S and where one or more H atoms in the above-mentioned groups may be replaced by D, F or CN, or an aromatic ring system having 6 to 18 aromatic ring atoms, which may in each case be substituted by one or more radicals $R^3$, where two or more alkyl, alkoxy or thioalkyl groups $R^1$ may be linked to one another and may form a ring.

$R^1$ is particularly preferably on each occurrence, identically or differently, H, D, a straight-chain alkyl or alkoxy group having 1 to 10 C atoms or a branched or cyclic alkyl or alkoxy group having 3 to 10 C atoms, where the above-mentioned groups may each be substituted by one or more radicals $R^3$, or an aromatic ring system having 6 to 12 aromatic ring atoms, which may in each case be substituted by one or more radicals $R^3$, where two or more alkyl or alkoxy groups $R^1$ may be linked to one another and may form a ring.

It is furthermore preferred in accordance with the invention for radicals $R^1$ on a group $X=C(R^1)_2$ to form a cycloalkyl ring with one another. Particular preference is given to a cyclohexyl and a cyclopentyl ring, each of which may be substituted by one or more radicals $R^3$.

It is furthermore preferred for at least one group $R^1$ in a group $X=C(R^1)_2$ in the compound according to the invention not to be an aromatic group, i.e. not to be an aromatic ring system and not to be an aryl group. The groups $R^1$ in a group $X=C(R^1)_2$ in the compound according to the invention particularly preferably do not represent an aromatic ring system and do not represent an aryl group.

In accordance with a preferred embodiment, $R^2$ is on each occurrence, identically or differently, H, D, F, CN, $Si(R^3)_3$, a straight-chain alkyl or alkoxy group having 1 to 10 C atoms or a branched or cyclic alkyl or alkoxy group having 3 to 10 C atoms, where the above-mentioned groups may each be substituted by one or more radicals $R^3$ and where one or more $CH_2$ groups in the above-mentioned groups may be replaced by Si(R³)₂, O and S, or an aromatic or heteroaromatic ring system having 5 to 18 aromatic ring atoms, which may in each case be substituted by one or more radicals R³, where two or more radicals R² may be linked to one another and may form a ring.

In accordance with a further preferred embodiment, R³ is on each occurrence, identically or differently, H, D, F, CN, Si(R⁴)₃ or a straight-chain alkyl or alkoxy group having 1 to 10 C atoms or a branched or cyclic alkyl or alkoxy group having 3 to 10 C atoms, where the above-mentioned groups may each be substituted by one or more radicals R⁴ and where one or more CH₂ groups in the above-mentioned groups may be replaced by Si(R⁴)₂, O and S, or an aromatic or heteroaromatic ring system having 5 to 18 aromatic ring atoms, which may in each case be substituted by one or more radicals R⁴, where two or more radicals R³ may be linked to one another and may form a ring.

In accordance with a further preferred embodiment, the compound according to the invention contains no heteroaryl group selected from triazine, pyrimidine, pyrazine, pyridazine, pyridine, imidazole and benzimidazole and no keto group, no phosphorus oxide group and no sulfur oxide group. The compound according to invention particularly preferably contains no electron-deficient heteroaryl group and no keto group, no phosphorus oxide group and no sulfur oxide group.

An electron-deficient heteroaryl group for the purposes of the present invention is taken to mean, in particular, heteroaromatic six-membered rings having one or more nitrogen atoms and heteroaromatic five-membered rings having two or more heteroatoms, in particular heteroatoms selected from N, O and S.

In accordance with a further preferred embodiment, the compound according to the invention contains no further arylamino group in addition to the amino group of the basic structure.

Preferred embodiments of the compound of the formula (I) according to the invention are reproduced by the following formulae (I-A), (I-B) and (I-C):

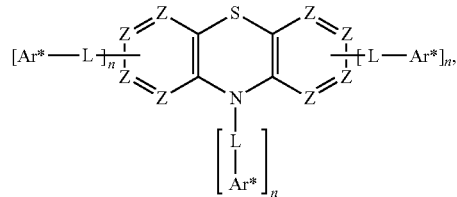

formula (I-A)

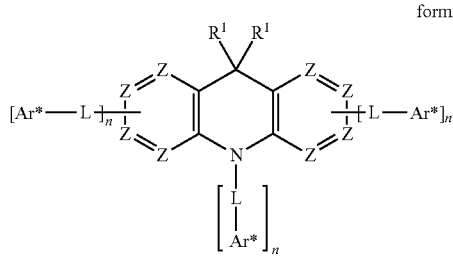

formula (I-B)

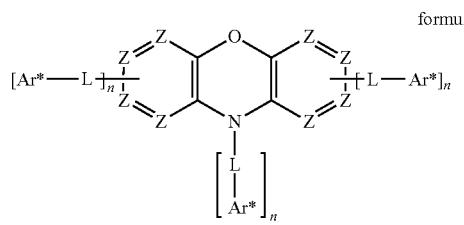

formula (I-C)

where the symbols and indices occurring are as defined above. Preference is given to the combination of the above-mentioned preferred embodiments of the groups R¹, Ar*, L and Z and of the index n with the structures of the formulae (I-A) to (I-C).

Preferred embodiments of the formula (I-A) are the formulae (I-A-1) and (I-A-2)

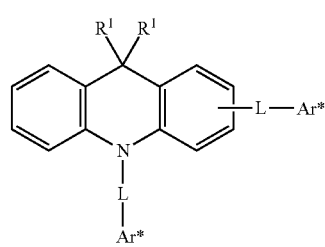

formula (I-A-1)

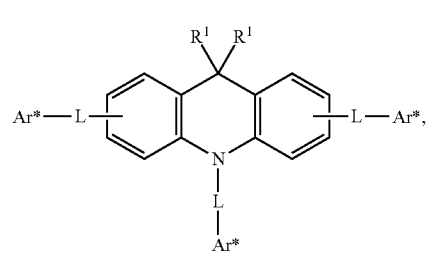

formula (I-A-2)

where the symbols occurring are defined as indicated above and the free positions on the aromatic six-membered rings may be substituted by radicals R².

Preference is given to the combination of the above-mentioned preferred embodiments of the groups R¹, Ar* and L with the structures of the formulae (I-A-1) and (I-A-2). It is furthermore preferred for the groups L-Ar* to be bonded in the meta- or para-positions to the nitrogen atom, particularly preferably in the para-position to the nitrogen atom.

Preferred embodiments of the formula (I-B) are the formulae (I-B-1) and (I-B-2)

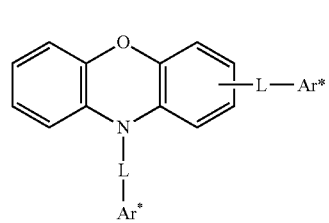

formula (I-B-1)

-continued

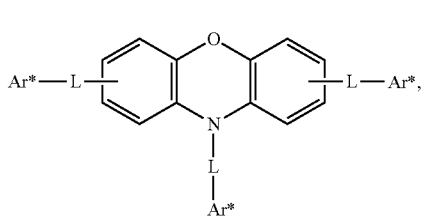

formula (I-B-2)

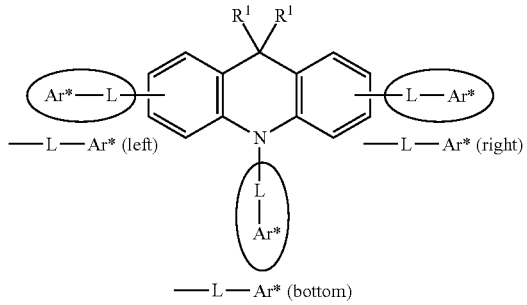

where the symbols occurring are defined as indicated above and the free positions on the aromatic six-membered rings may be substituted by radicals $R^2$.

Preference is given to the combination of the above-mentioned preferred embodiments of the groups Ar* and L with the structures of the formulae (I-B-1) and (I-B-2). It is furthermore preferred for the groups L-Ar* be bonded in the meta- or para-positions to the nitrogen atom, particularly preferably in the para-position to the nitrogen atom.

Preferred embodiments of the formula (I-C) are the formulae (I-C-1) and (I-C-2)

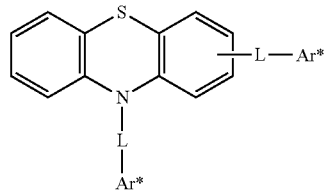

formula (I-C-1)

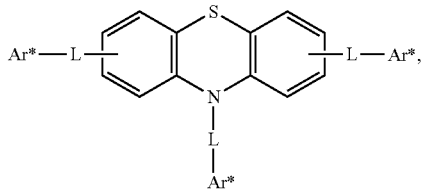

formula (I-C-2)

where the symbols occurring are defined as indicated above and the free positions on the aromatic six-membered rings may be substituted by radicals $R^2$.

Preference is given to the combination of the above-mentioned preferred embodiments of the groups Ar* and L with the structures of the formulae (I-C-1) and (I-C-2). It is furthermore preferred for the groups L-Ar* to be bonded in the meta- or para-positions to the nitrogen atom, particularly preferably in the para-position to the nitrogen atom.

Furthermore, the following combinations of groups Ar* of the formulae (H-1), (H-3), (A-1) and (A-2) with the preferred structures of the formulae (I-A-1), (I-A-2), (I-B-1), (I-B-2), (I-C-1) and (I-C-2) are preferred (L is a single bond in all cases shown in the table):

The various groups L-Ar* occurring are denoted here as follows (shown for the example of the formula (I-A-2):

|  | Basic structure | —L—Ar* (left) | —L—Ar* (right) | —L—Ar* (bottom) |
|---|---|---|---|---|
| (I-A-1-1) | (I-A-1) | — | (H-1) | (H-1) |
| (I-A-1-2) | see above | — | (H-1) | (H-3) |
| (I-A-1-3) | see above | — | (H-1) | (A-1) |
| (I-A-1-4) | see above | — | (H-1) | (A-2) |
| (I-A-1-5) | see above | — | (H-3) | (H-1) |
| (I-A-1-6) | see above | — | (H-3) | (H-3) |
| (I-A-1-7) | see above | — | (H-3) | (A-1) |
| (I-A-1-8) | see above | — | (H-3) | (A-2) |
| (I-A-1-9) | see above | — | (A-1) | (H-1) |
| (I-A-1-10) | see above | — | (A-1) | (H-3) |
| (I-A-1-11) | see above | — | (A-1) | (A-1) |
| (I-A-1-12) | see above | — | (A-1) | (A-2) |
| (I-A-1-13) | see above | — | (A-2) | (H-1) |
| (I-A-1-14) | see above | — | (A-2) | (H-3) |
| (I-A-1-15) | see above | — | (A-2) | (A-1) |
| (I-A-1-16) | see above | — | (A-2) | (A-2) |
| (I-A-2-1) | (I-A-2) | (H-1) | (H-1) | (H-1) |
| (I-A-2-2) | see above | (H-1) | (H-3) | (H-1) |
| (I-A-2-3) | see above | (H-1) | (A-1) | (H-1) |
| (I-A-2-4) | see above | (H-1) | (A-2) | (H-1) |
| (I-A-2-5) | see above | (H-3) | (H-3) | (H-1) |
| (I-A-2-6) | see above | (H-3) | (A-1) | (H-1) |
| (I-A-2-7) | see above | (H-3) | (A-2) | (H-1) |
| (I-A-2-8) | see above | (A-1) | (A-1) | (H-1) |
| (I-A-2-9) | see above | (A-1) | (A-2) | (H-1) |
| (I-A-2-10) | see above | (A-2) | (A-2) | (H-1) |
| (I-A-2-11) | see above | (H-1) | (H-1) | (H-3) |
| (I-A-2-12) | see above | (H-1) | (H-3) | (H-3) |
| (I-A-2-13) | see above | (H-1) | (A-1) | (H-3) |
| (I-A-2-14) | see above | (H-1) | (A-2) | (H-3) |
| (I-A-2-15) | see above | (H-3) | (H-3) | (H-3) |
| (I-A-2-16) | see above | (H-3) | (A-1) | (H-3) |
| (I-A-2-17) | see above | (H-3) | (A-2) | (H-3) |
| (I-A-2-18) | see above | (A-1) | (A-1) | (H-3) |
| (I-A-2-19) | see above | (A-1) | (A-2) | (H-3) |
| (I-A-2-20) | see above | (A-2) | (A-2) | (H-3) |
| (I-A-2-21) | see above | (H-1) | (H-1) | (A-1) |
| (I-A-2-22) | see above | (H-1) | (H-3) | (A-1) |
| (I-A-2-23) | see above | (H-1) | (A-1) | (A-1) |
| (I-A-2-24) | see above | (H-1) | (A-2) | (A-1) |
| (I-A-2-25) | see above | (H-3) | (H-3) | (A-1) |
| (I-A-2-26) | see above | (H-3) | (A-1) | (A-1) |
| (I-A-2-27) | see above | (H-3) | (A-2) | (A-1) |
| (I-A-2-28) | see above | (A-1) | (A-1) | (A-1) |
| (I-A-2-29) | see above | (A-1) | (A-2) | (A-1) |
| (I-A-2-30) | see above | (A-2) | (A-2) | (A-1) |
| (I-A-2-31) | see above | (H-1) | (H-1) | (A-2) |
| (I-A-2-32) | see above | (H-1) | (H-3) | (A-2) |
| (I-A-2-33) | see above | (H-1) | (A-1) | (A-2) |
| (I-A-2-34) | see above | (H-1) | (A-2) | (A-2) |
| (I-A-2-35) | see above | (H-3) | (H-3) | (A-2) |
| (I-A-2-36) | see above | (H-3) | (A-1) | (A-2) |
| (I-A-2-37) | see above | (H-3) | (A-2) | (A-2) |
| (I-A-2-38) | see above | (A-1) | (A-1) | (A-2) |
| (I-A-2-39) | see above | (A-1) | (A-2) | (A-2) |
| (I-A-2-40) | see above | (A-2) | (A-2) | (A-2) |
| (I-B-1-1) | (I-B-1) | — | (H-1) | (H-1) |
| (I-B-1-2) | see above | — | (H-1) | (H-3) |
| (I-B-1-3) | see above | — | (H-1) | (A-1) |
| (I-B-1-4) | see above | — | (H-1) | (A-2) |
| (I-B-1-5) | see above | — | (H-3) | (H-1) |
| (I-B-1-6) | see above | — | (H-3) | (H-3) |

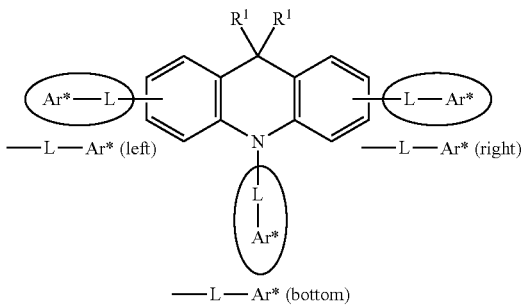

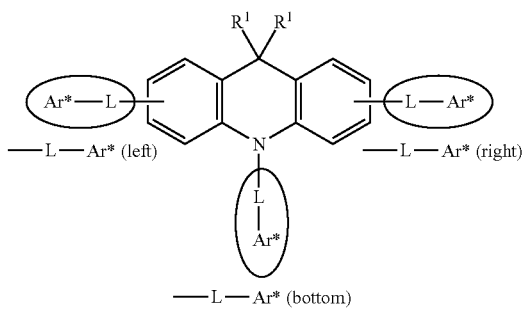

| Basic structure | —L—Ar* (left) | —L—Ar* (right) | —L—Ar* (bottom) |
|---|---|---|---|
| (I-B-1-7) | see above | — | (H-3) | (A-1) |
| (I-B-1-8) | see above | — | (H-3) | (A-2) |
| (I-B-1-9) | see above | — | (A-1) | (H-1) |
| (I-B-1-10) | see above | — | (A-1) | (H-3) |
| (I-B-1-11) | see above | — | (A-1) | (A-1) |
| (I-B-1-12) | see above | — | (A-1) | (A-2) |
| (I-B-1-13) | see above | — | (A-2) | (H-1) |
| (I-B-1-14) | see above | — | (A-2) | (H-3) |
| (I-B-1-15) | see above | — | (A-2) | (A-1) |
| (I-B-1-16) | see above | — | (A-2) | (A-2) |
| (I-B-2-1) | (I-B-2) | (H-1) | (H-1) | (H-1) |
| (I-B-2-2) | see above | (H-1) | (H-3) | (H-1) |
| (I-B-2-3) | see above | (H-1) | (A-1) | (H-1) |
| (I-B-2-4) | see above | (H-1) | (A-2) | (H-1) |
| (I-B-2-5) | see above | (H-3) | (H-3) | (H-1) |
| (I-B-2-6) | see above | (H-3) | (A-1) | (H-1) |
| (I-B-2-7) | see above | (H-3) | (A-2) | (H-1) |
| (I-B-2-8) | see above | (A-1) | (A-1) | (H-1) |
| (I-B-2-9) | see above | (A-1) | (A-2) | (H-1) |
| (I-B-2-10) | see above | (A-2) | (A-2) | (H-1) |
| (I-B-2-11) | see above | (H-1) | (H-1) | (H-3) |
| (I-B-2-12) | see above | (H-1) | (H-3) | (H-3) |
| (I-B-2-13) | see above | (H-1) | (A-1) | (H-3) |
| (I-B-2-14) | see above | (H-1) | (A-2) | (H-3) |
| (I-B-2-15) | see above | (H-3) | (H-3) | (H-3) |
| (I-B-2-16) | see above | (H-3) | (A-1) | (H-3) |
| (I-B-2-17) | see above | (H-3) | (A-2) | (H-3) |
| (I-B-2-18) | see above | (A-1) | (A-1) | (H-3) |
| (I-B-2-19) | see above | (A-1) | (A-2) | (H-3) |
| (I-B-2-20) | see above | (A-2) | (A-2) | (H-3) |
| (I-B-2-21) | see above | (H-1) | (H-1) | (A-1) |
| (I-B-2-22) | see above | (H-1) | (H-3) | (A-1) |
| (I-B-2-23) | see above | (H-1) | (A-1) | (A-1) |
| (I-B-2-24) | see above | (H-1) | (A-2) | (A-1) |
| (I-B-2-25) | see above | (H-3) | (H-3) | (A-1) |
| (I-B-2-26) | see above | (H-3) | (A-1) | (A-1) |
| (I-B-2-27) | see above | (H-3) | (A-2) | (A-1) |
| (I-B-2-28) | see above | (A-1) | (A-1) | (A-1) |
| (I-B-2-29) | see above | (A-1) | (A-2) | (A-1) |
| (I-B-2-30) | see above | (A-2) | (A-2) | (A-1) |
| (I-B-2-31) | see above | (H-1) | (H-1) | (A-2) |
| (I-B-2-32) | see above | (H-1) | (H-3) | (A-2) |
| (I-B-2-33) | see above | (H-1) | (A-1) | (A-2) |
| (I-B-2-34) | see above | (H-1) | (A-2) | (A-2) |
| (I-B-2-35) | see above | (H-3) | (H-3) | (A-2) |
| (I-B-2-36) | see above | (H-3) | (A-1) | (A-2) |
| (I-B-2-37) | see above | (H-3) | (A-2) | (A-2) |
| (I-B-2-38) | see above | (A-1) | (A-1) | (A-2) |
| (I-B-2-39) | see above | (A-1) | (A-2) | (A-2) |
| (I-B-2-40) | see above | (A-2) | (A-2) | (A-2) |
| (I-C-1-1) | (I-C-1) | — | (H-1) | (H-1) |
| (I-C-1-2) | see above | — | (H-1) | (H-3) |
| (I-C-1-3) | see above | — | (H-1) | (A-1) |
| (I-C-1-4) | see above | — | (H-1) | (A-2) |
| (I-C-1-5) | see above | — | (H-3) | (H-1) |
| (I-C-1-6) | see above | — | (H-3) | (H-3) |
| (I-C-1-7) | see above | — | (H-3) | (A-1) |
| (I-C-1-8) | see above | — | (H-3) | (A-2) |
| (I-C-1-9) | see above | — | (A-1) | (H-1) |
| (I-C-1-10) | see above | — | (A-1) | (H-3) |
| (I-C-1-11) | see above | — | (A-1) | (A-1) |
| (I-C-1-12) | see above | — | (A-1) | (A-2) |
| (I-C-1-13) | see above | — | (A-2) | (H-1) |
| (I-C-1-14) | see above | — | (A-2) | (H-3) |
| (I-C-1-15) | see above | — | (A-2) | (A-1) |
| (I-C-1-16) | see above | — | (A-2) | (A-2) |
| (I-C-2-1) | (I-C-2) | (H-1) | (H-1) | (H-1) |
| (I-C-2-2) | see above | (H-1) | (H-3) | (H-1) |
| (I-C-2-3) | see above | (H-1) | (A-1) | (H-1) |
| (I-C-2-4) | see above | (H-1) | (A-2) | (H-1) |
| (I-C-2-5) | see above | (H-3) | (H-3) | (H-1) |
| (I-C-2-6) | see above | (H-3) | (A-1) | (H-1) |
| (I-C-2-7) | see above | (H-3) | (A-2) | (H-1) |
| (I-C-2-8) | see above | (A-1) | (A-1) | (H-1) |
| (I-C-2-9) | see above | (A-1) | (A-2) | (H-1) |
| (I-C-2-10) | see above | (A-2) | (A-2) | (H-1) |
| (I-C-2-11) | see above | (H-1) | (H-1) | (H-3) |
| (I-C-2-12) | see above | (H-1) | (H-3) | (H-3) |
| (I-C-2-13) | see above | (H-1) | (A-1) | (H-3) |
| (I-C-2-14) | see above | (H-1) | (A-2) | (H-3) |
| (I-C-2-15) | see above | (H-3) | (H-3) | (H-3) |
| (I-C-2-16) | see above | (H-3) | (A-1) | (H-3) |
| (I-C-2-17) | see above | (H-3) | (A-2) | (H-3) |
| (I-C-2-18) | see above | (A-1) | (A-1) | (H-3) |
| (I-C-2-19) | see above | (A-1) | (A-2) | (H-3) |
| (I-C-2-20) | see above | (A-2) | (A-2) | (H-3) |
| (I-C-2-21) | see above | (H-1) | (H-1) | (A-1) |
| (I-C-2-22) | see above | (H-1) | (H-3) | (A-1) |
| (I-C-2-23) | see above | (H-1) | (A-1) | (A-1) |
| (I-C-2-24) | see above | (H-1) | (A-2) | (A-1) |
| (I-C-2-25) | see above | (H-3) | (H-3) | (A-1) |
| (I-C-2-26) | see above | (H-3) | (A-1) | (A-1) |
| (I-C-2-27) | see above | (H-3) | (A-2) | (A-1) |
| (I-C-2-28) | see above | (A-1) | (A-1) | (A-1) |
| (I-C-2-29) | see above | (A-1) | (A-2) | (A-1) |
| (I-C-2-30) | see above | (A-2) | (A-2) | (A-1) |
| (I-C-2-31) | see above | (H-1) | (H-1) | (A-2) |
| (I-C-2-32) | see above | (H-1) | (H-3) | (A-2) |
| (I-C-2-33) | see above | (H-1) | (A-1) | (A-2) |
| (I-C-2-34) | see above | (H-1) | (A-2) | (A-2) |
| (I-C-2-35) | see above | (H-3) | (H-3) | (A-2) |
| (I-C-2-36) | see above | (H-3) | (A-1) | (A-2) |
| (I-C-2-37) | see above | (H-3) | (A-2) | (A-2) |
| (I-C-2-38) | see above | (A-1) | (A-1) | (A-2) |
| (I-C-2-39) | see above | (A-1) | (A-2) | (A-2) |
| (I-C-2-40) | see above | (A-2) | (A-2) | (A-2) |

The compounds indicated in the table may be substituted by radicals $R^1$ and $R^2$, as defined above. In this connection, preference is given to the above-mentioned preferred embodiments of the radicals $R^1$ and $R^2$.

Examples of compounds according to the invention are shown in the following table.

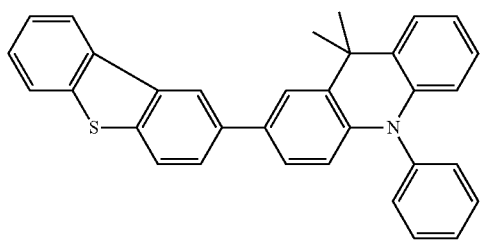 [SMILES: CC1(C)c2ccccc2N(c2ccccc2)c2ccc(-c3ccc4sc5ccccc5c4c3)cc21]
1
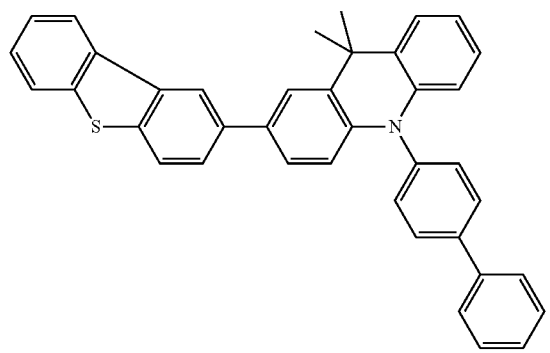 [SMILES: CC1(C)c2ccccc2N(c2ccc(-c3ccccc3)cc2)c2ccc(-c3ccc4sc5ccccc5c4c3)cc21]
2
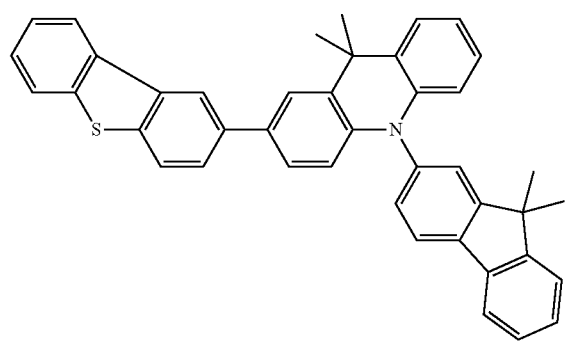 [SMILES: CC1(C)c2ccccc2-c2ccc(N3c4ccccc4C(C)(C)c4cc(-c5ccc6sc7ccccc7c6c5)ccc43)cc21]
3
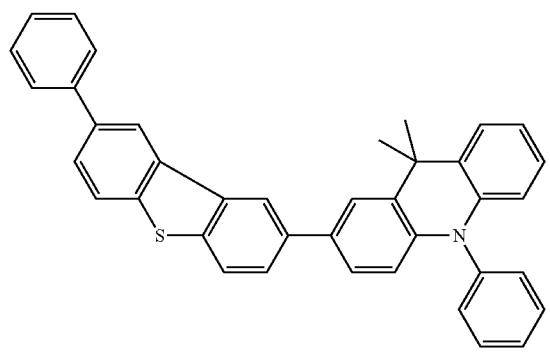 [SMILES: CC1(C)c2ccccc2N(c2ccccc2)c2ccc(-c3ccc4sc5ccc(-c6ccccc6)cc5c4c3)cc21]
4

-continued
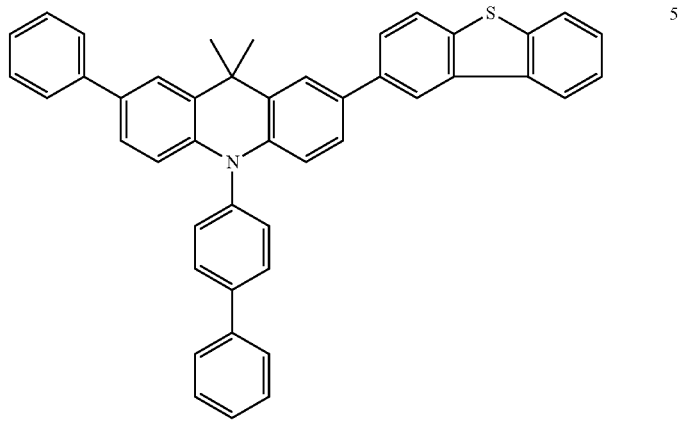
5
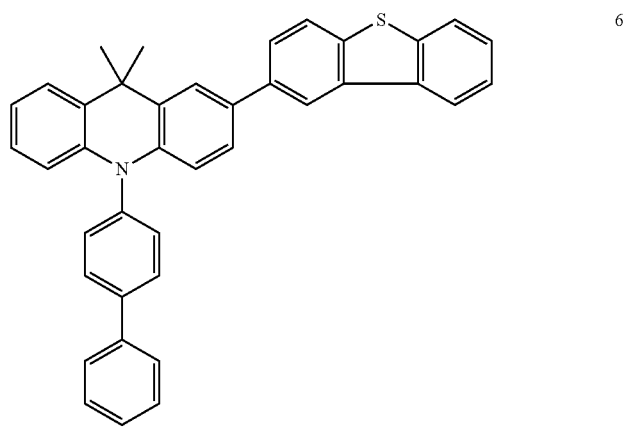
6
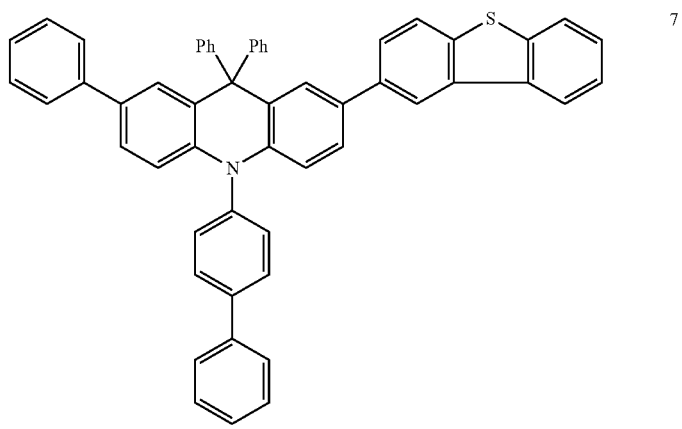
7

-continued
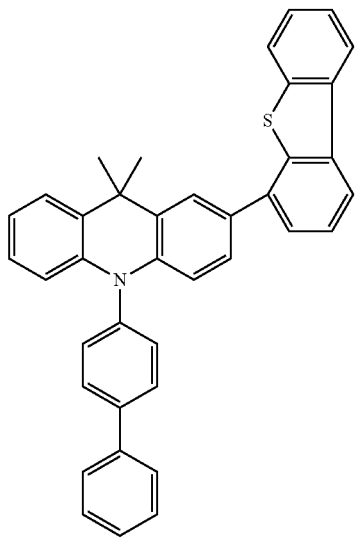
8
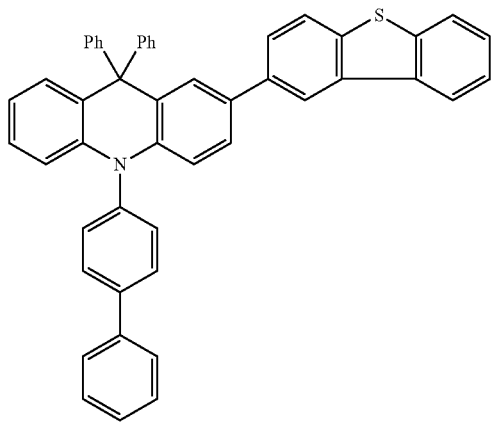
9
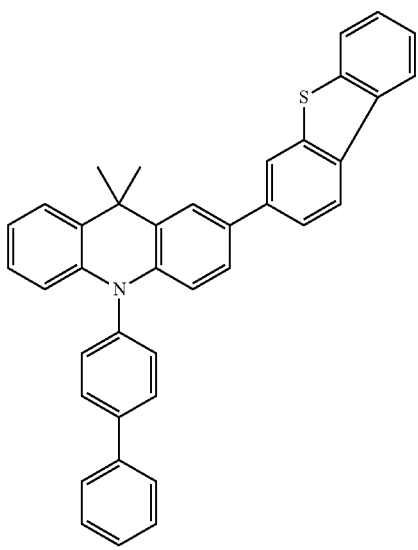 [SMILES: CC1(C)c2ccccc2N(c2ccc(-c3ccccc3)cc2)c2ccc(-c3ccc4c(c3)sc3ccccc34)cc21]
10

-continued
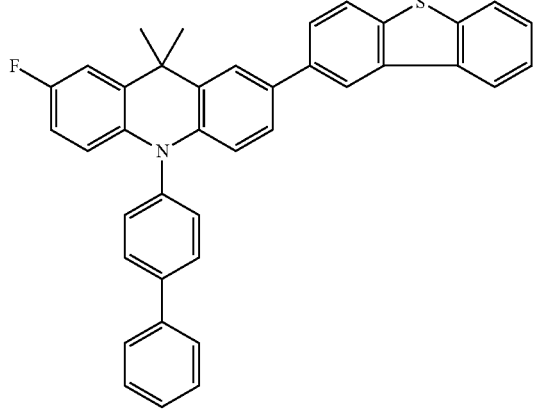
11
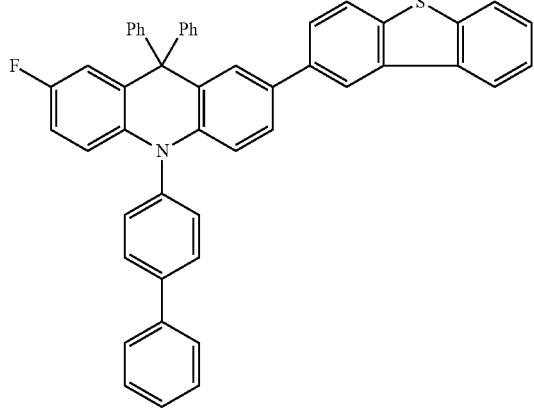
12
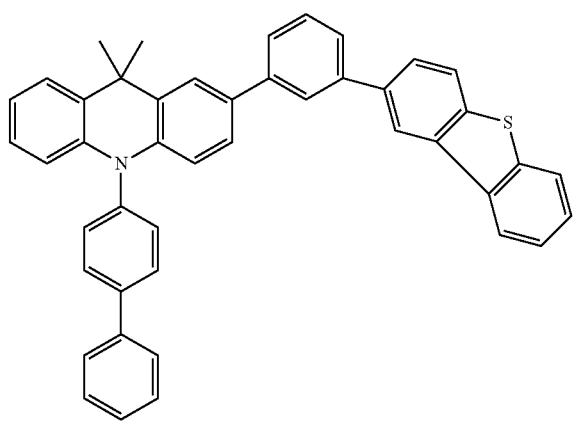 [SMILES: CC1(C)c2ccccc2N(c2ccc(-c3ccccc3)cc2)c2ccc(-c3cccc(-c4ccc5sc6ccccc6c5c4)c3)cc21]
13

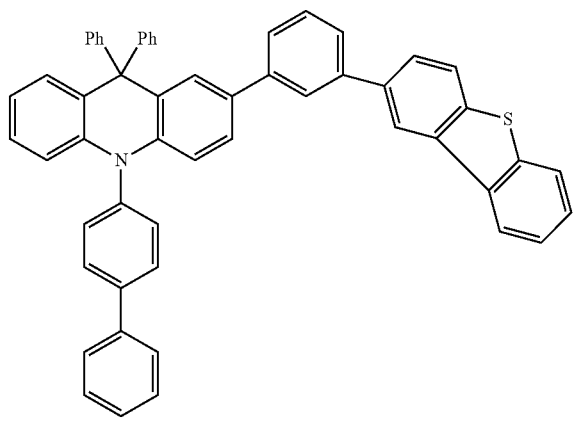 [SMILES: c1ccc(-c2ccc(N3c4ccccc4C(c4ccccc4)(c4ccccc4)c4cc(-c5cccc(-c6ccc7sc8ccccc8c7c6)c5)ccc43)cc2)cc1]
14
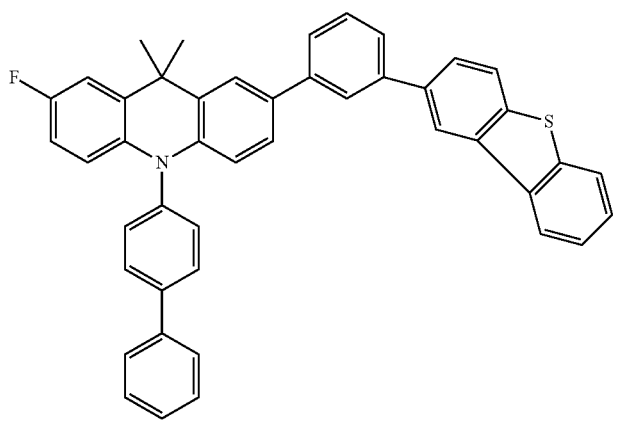
15
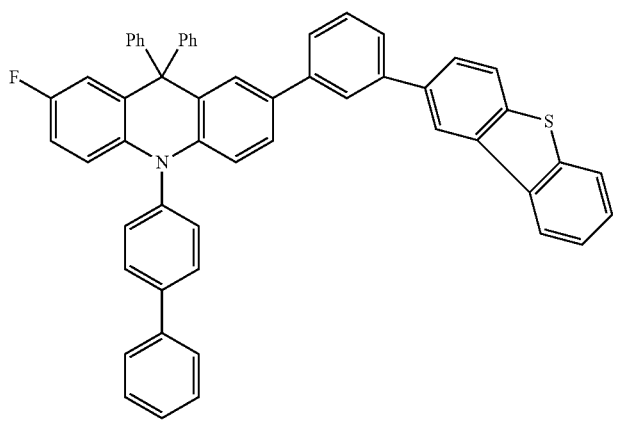
16
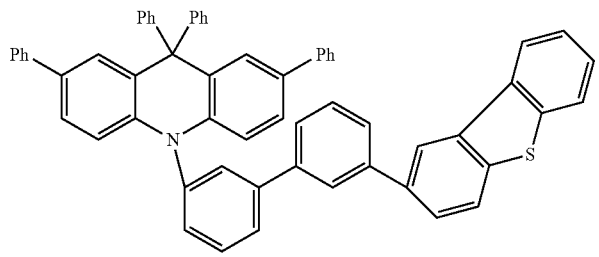 [SMILES: c1ccc(-c2ccc3c(c2)C(c2ccccc2)(c2ccccc2)c2cc(-c4ccccc4)ccc2N3c2cccc(-c3cccc(-c4ccc5sc6ccccc6c5c4)c3)c2)cc1]
17

-continued
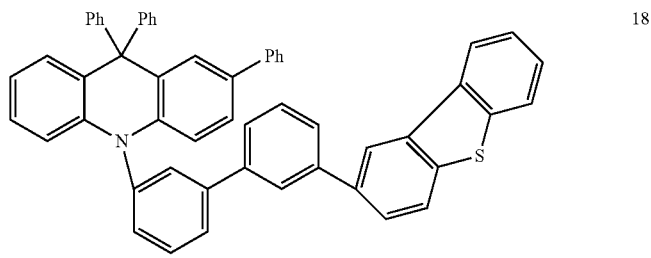
18
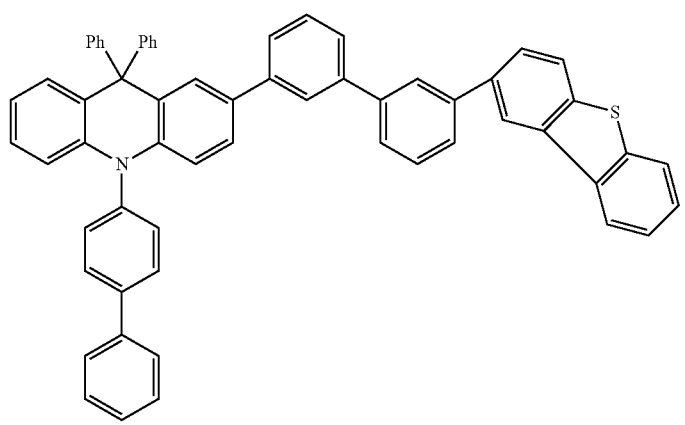 [SMILES: c1ccc(-c2ccc(N3c4ccccc4C(c4ccccc4)(c4ccccc4)c4cc(-c5cccc(-c6cccc(-c7ccc8sc9ccccc9c8c7)c6)c5)ccc43)cc2)cc1]
19
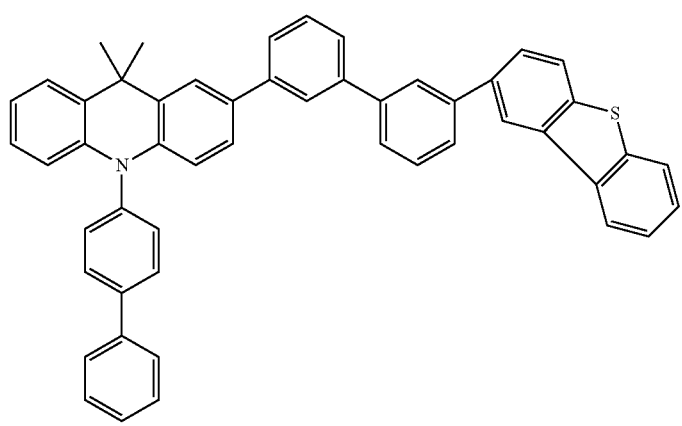 [SMILES: CC1(C)c2ccccc2N(c2ccc(-c3ccccc3)cc2)c2ccc(-c3cccc(-c4cccc(-c5ccc6sc7ccccc7c6c5)c4)c3)cc21]
20
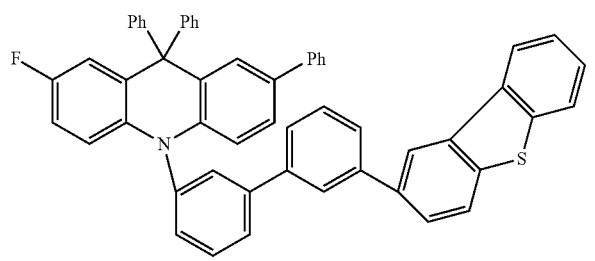 [SMILES: Fc1ccc2c(c1)C(c1ccccc1)(c1ccccc1)c1cc(-c3ccccc3)ccc1N2c1cccc(-c2cccc(-c3ccc4sc5ccccc5c4c3)c2)c1]
21
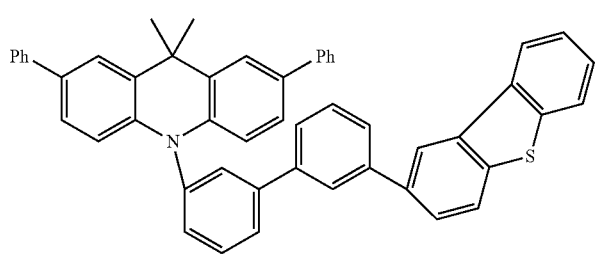 [SMILES: CC1(C)c2cc(-c3ccccc3)ccc2N(c2cccc(-c3cccc(-c4ccc5sc6ccccc6c5c4)c3)c2)c2ccc(-c3ccccc3)cc21]
22

-continued
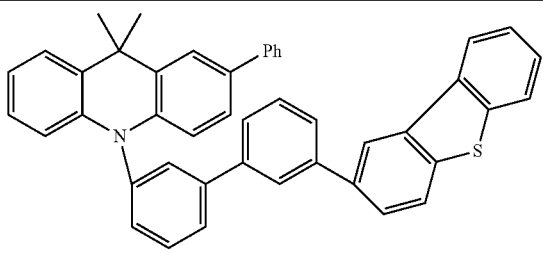
23
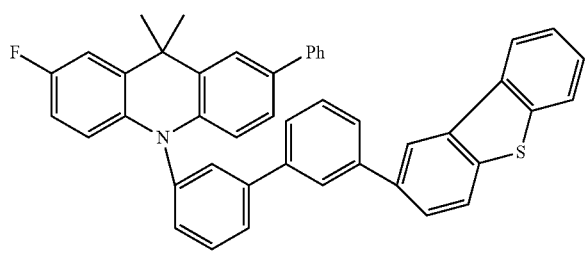 [SMILES: CC1(C)c2cc(F)ccc2N(c2cccc(-c3cccc(-c4ccc5sc6ccccc6c5c4)c3)c2)c2ccc(-c3ccccc3)cc21]
24
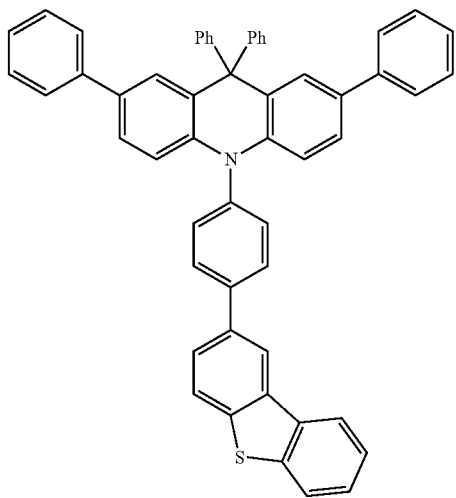
25
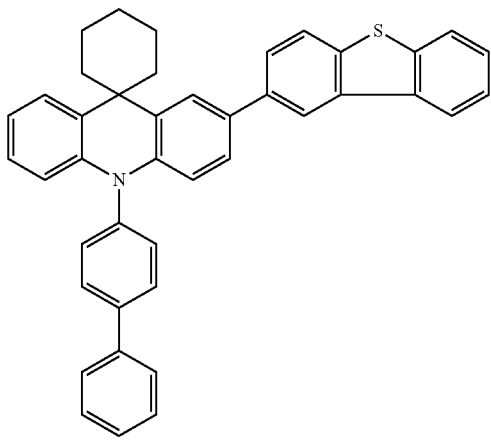
26

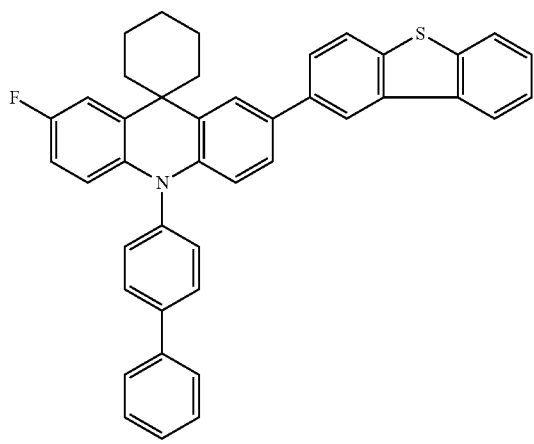 [SMILES: Fc1ccc2c(c1)C1(CCCCC1)c1cc(-c3ccc4sc5ccccc5c4c3)ccc1N2c1ccc(-c2ccccc2)cc1]
27
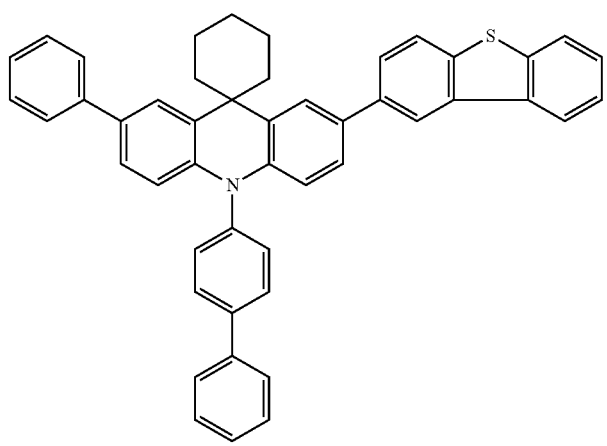 [SMILES: c1ccc(-c2ccc(N3c4ccc(-c5ccccc5)cc4C4(CCCCC4)c4cc(-c5ccc6sc7ccccc7c6c5)ccc43)cc2)cc1]
28
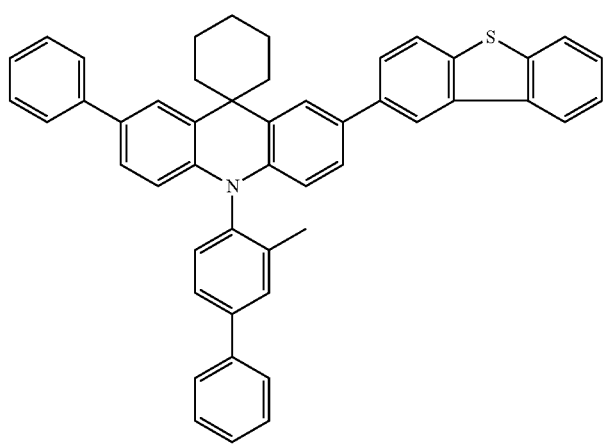 [SMILES: Cc1cc(-c2ccccc2)ccc1N1c2ccc(-c3ccccc3)cc2C2(CCCCC2)c2cc(-c3ccc4sc5ccccc5c4c3)ccc21]
29

-continued
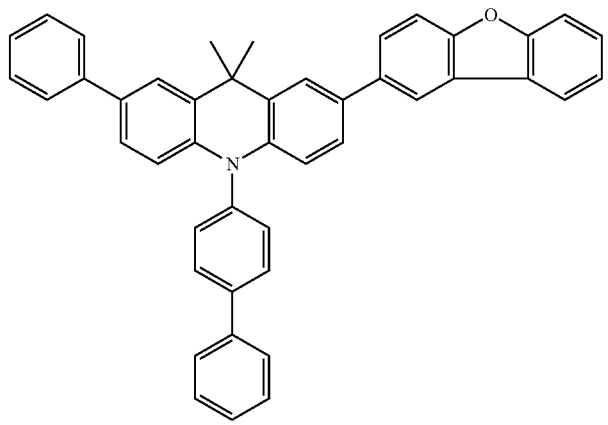 [SMILES: CC1(C)c2cc(-c3ccccc3)ccc2N(c2ccc(-c3ccccc3)cc2)c2ccc(-c3ccc4oc5ccccc5c4c3)cc21]
30
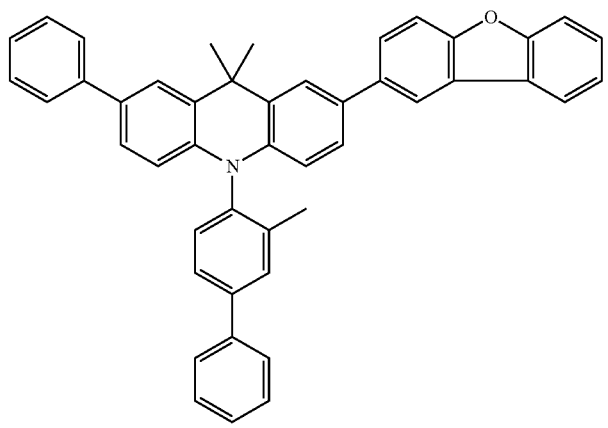 [SMILES: Cc1cc(-c2ccccc2)ccc1N1c2ccc(-c3ccccc3)cc2C(C)(C)c2cc(-c3ccc4oc5ccccc5c4c3)ccc21]
31
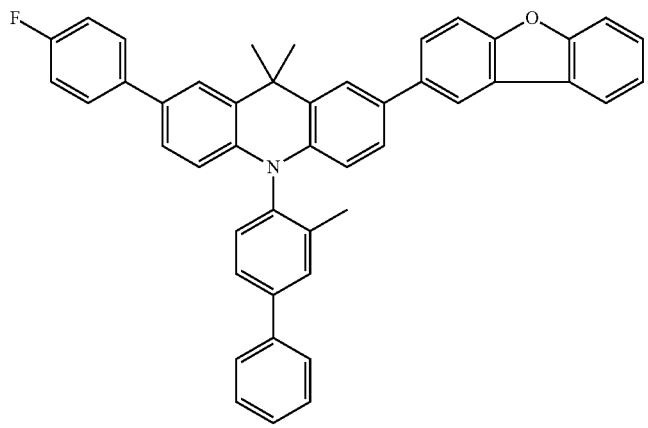 [SMILES: Cc1cc(-c2ccccc2)ccc1N1c2ccc(-c3ccc(F)cc3)cc2C(C)(C)c2cc(-c3ccc4oc5ccccc5c4c3)ccc21]
32

-continued
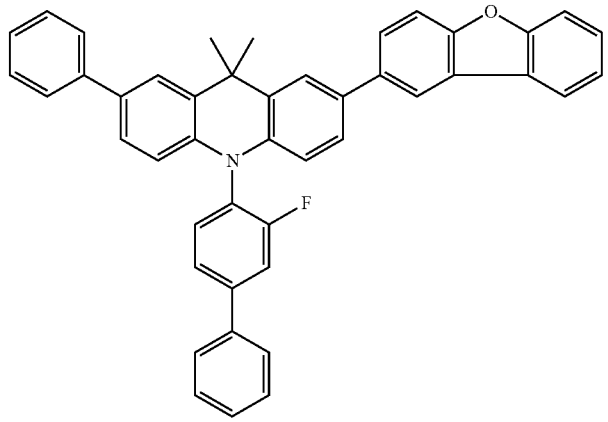 [SMILES: CC1(C)c2cc(-c3ccccc3)ccc2N(c2ccc(-c3ccccc3)cc2F)c2ccc(-c3ccc4oc5ccccc5c4c3)cc21]
33
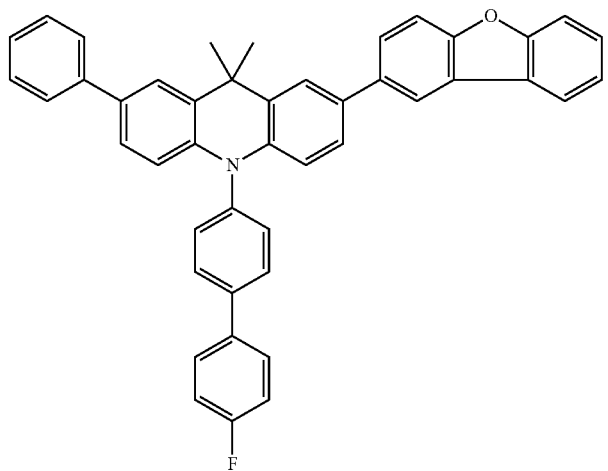 [SMILES: CC1(C)c2cc(-c3ccccc3)ccc2N(c2ccc(-c3ccc(F)cc3)cc2)c2ccc(-c3ccc4oc5ccccc5c4c3)cc21]
34
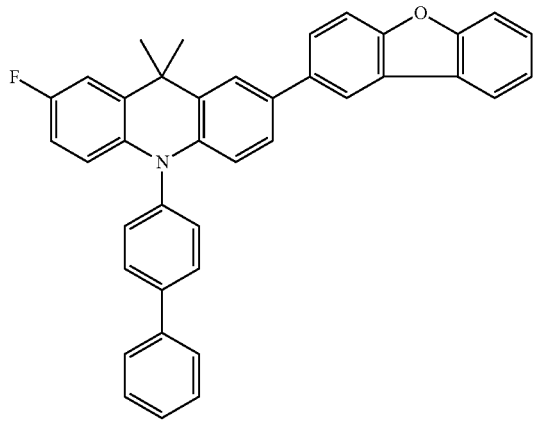 [SMILES: CC1(C)c2cc(F)ccc2N(c2ccc(-c3ccccc3)cc2)c2ccc(-c3ccc4oc5ccccc5c4c3)cc21]
35

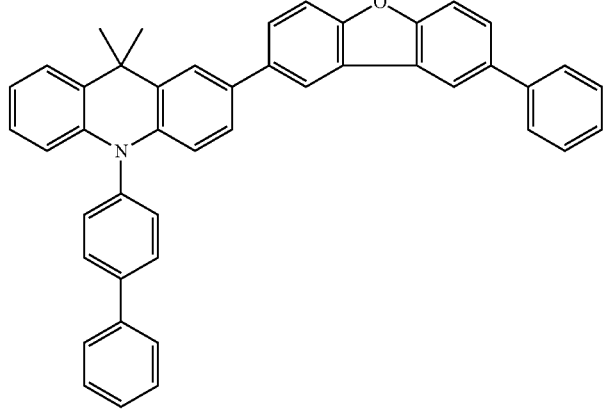
36
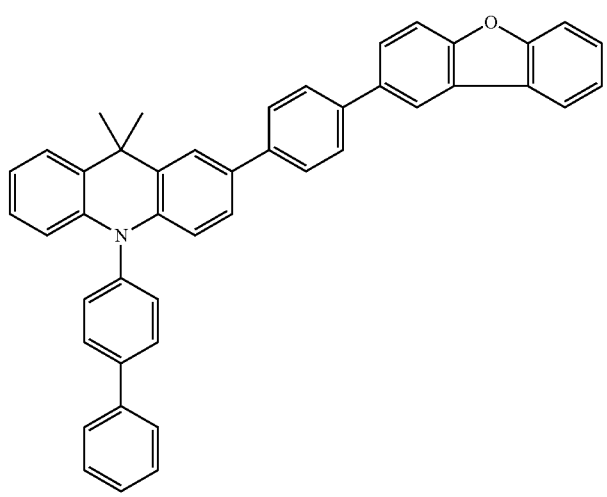 [SMILES: CC1(C)c2ccccc2N(c2ccc(-c3ccccc3)cc2)c2ccc(-c3ccc(-c4ccc5oc6ccccc6c5c4)cc3)cc21]
37
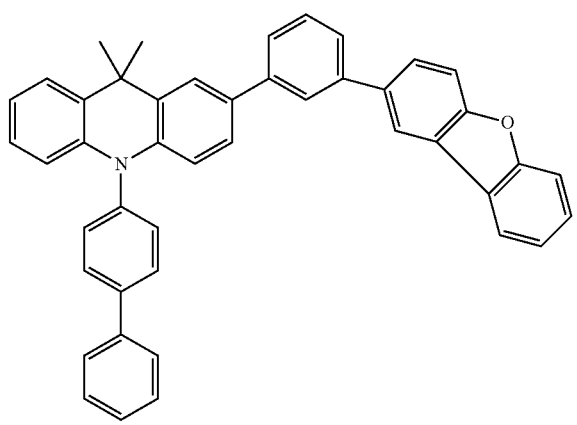 [SMILES: CC1(C)c2ccccc2N(c2ccc(-c3ccccc3)cc2)c2ccc(-c3cccc(-c4ccc5oc6ccccc6c5c4)c3)cc21]
38

-continued
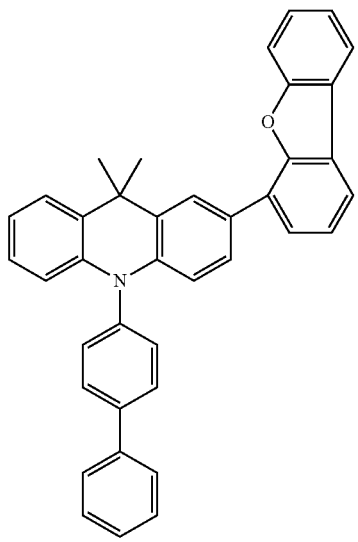 [SMILES: CC1(C)c2ccccc2N(c2ccc(-c3ccccc3)cc2)c2ccc(-c3cccc4c3oc3ccccc34)cc21]
39
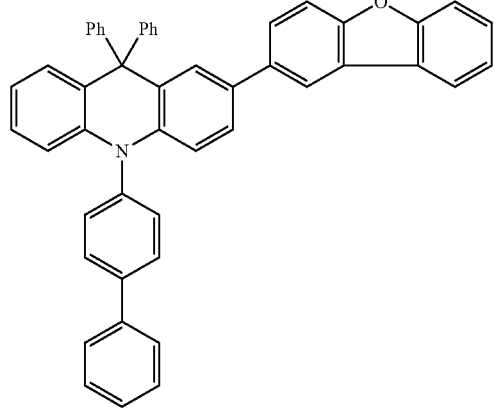
40
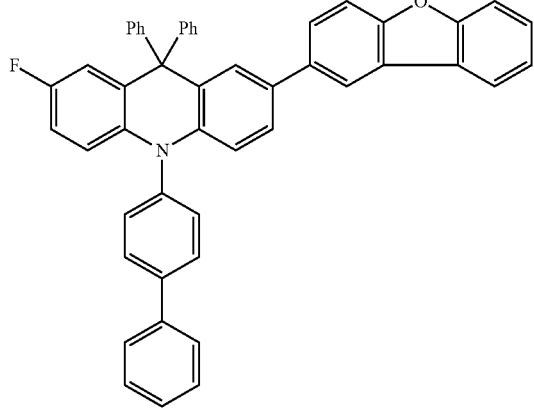
41

-continued
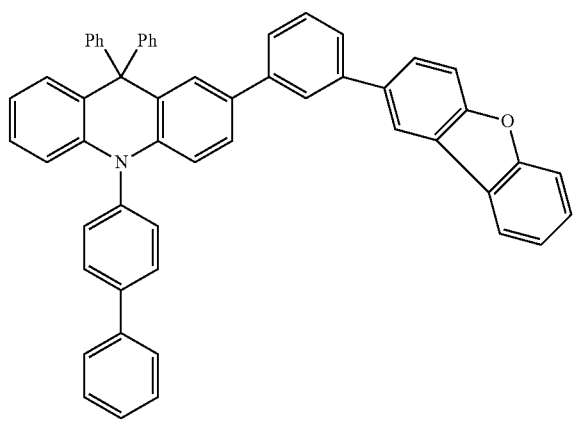
42
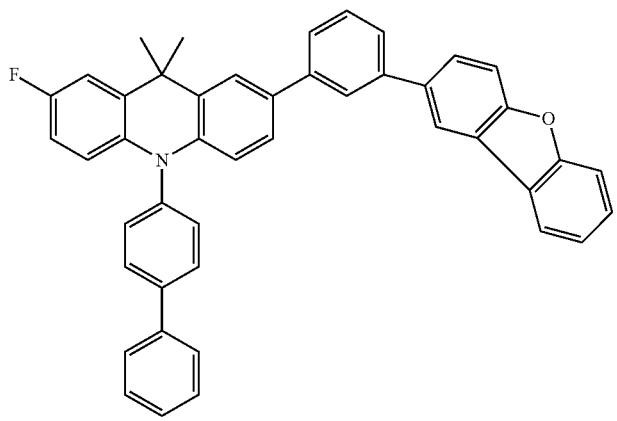
43
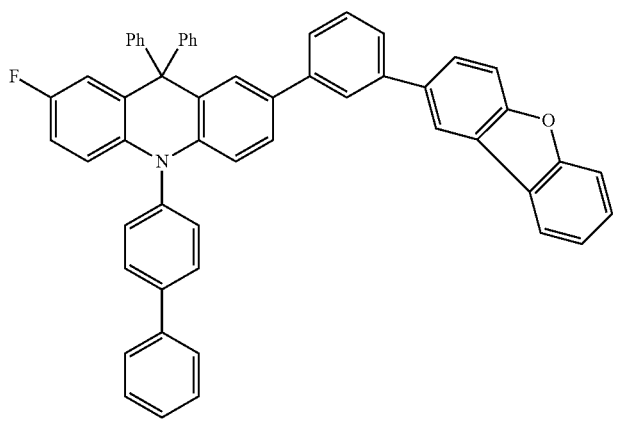 [SMILES: Fc1ccc2c(c1)C(c1ccccc1)(c1ccccc1)c1cc(-c3cccc(-c4ccc5oc6ccccc6c5c4)c3)ccc1N2c1ccc(-c2ccccc2)cc1]
44

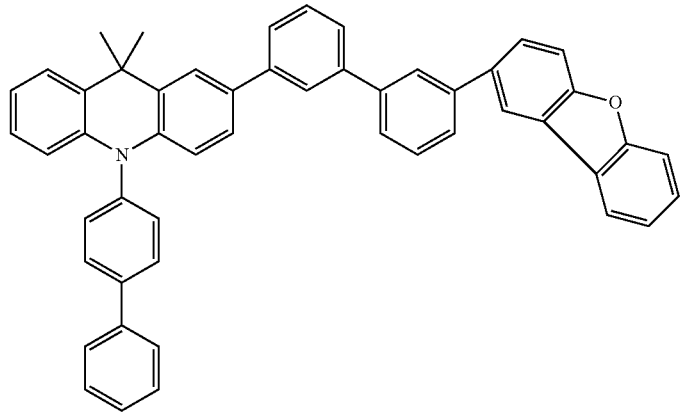 [SMILES: CC1(C)c2ccccc2N(c2ccc(-c3ccccc3)cc2)c2ccc(-c3cccc(-c4cccc(-c5ccc6oc7ccccc7c6c5)c4)c3)cc21]
45
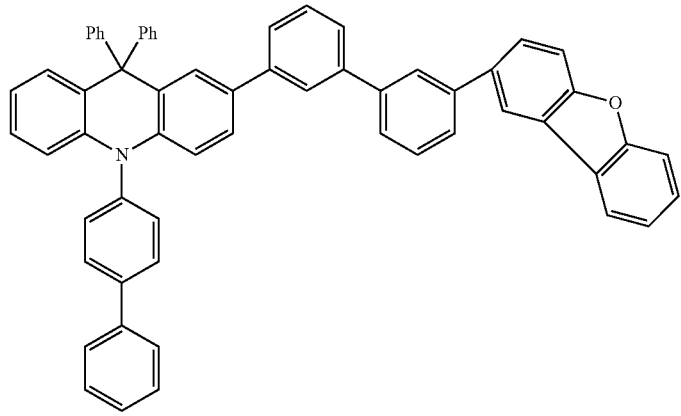
46
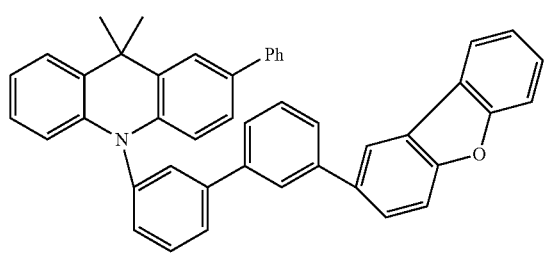 [SMILES: CC1(C)c2ccccc2N(c2cccc(-c3cccc(-c4ccc5oc6ccccc6c5c4)c3)c2)c2ccc(-c3ccccc3)cc21]
47
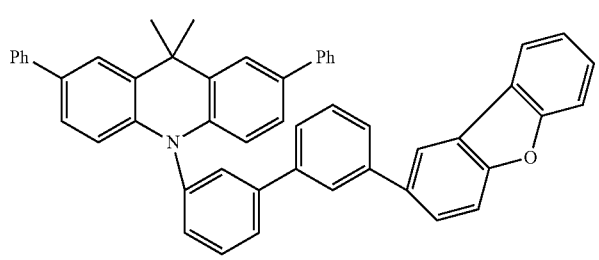
48

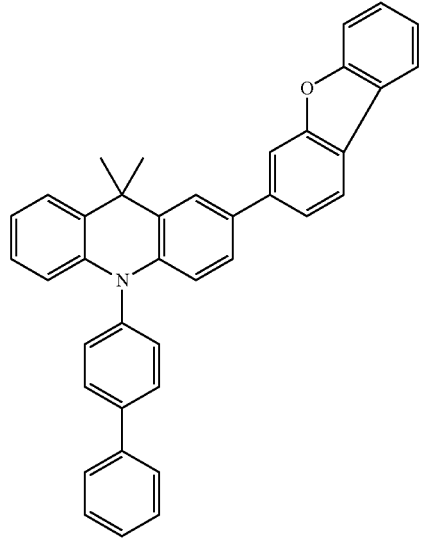 [SMILES: CC1(C)c2ccccc2N(c2ccc(-c3ccccc3)cc2)c2ccc(-c3ccc4c(c3)oc3ccccc34)cc21]
49
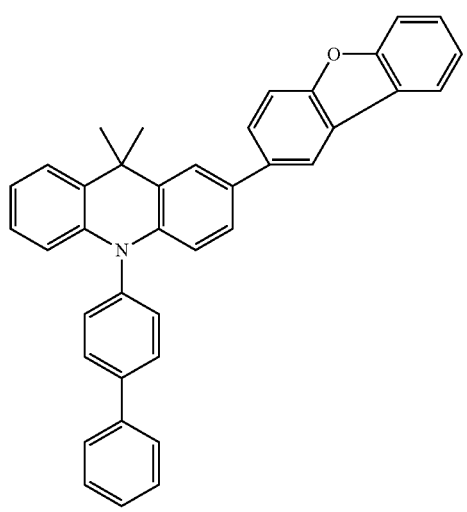 [SMILES: CC1(C)c2ccccc2N(c2ccc(-c3ccccc3)cc2)c2ccc(-c3ccc4oc5ccccc5c4c3)cc21]
50
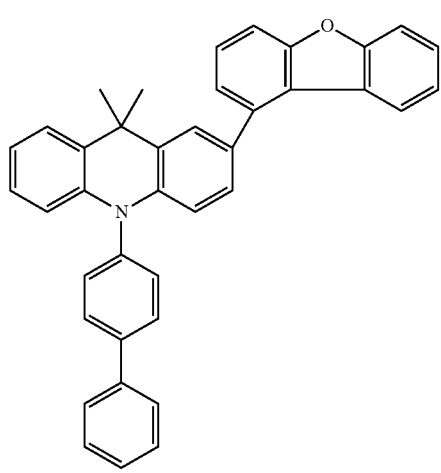 [SMILES: CC1(C)c2ccccc2N(c2ccc(-c3ccccc3)cc2)c2ccc(-c3cccc4oc5ccccc5c34)cc21]
51

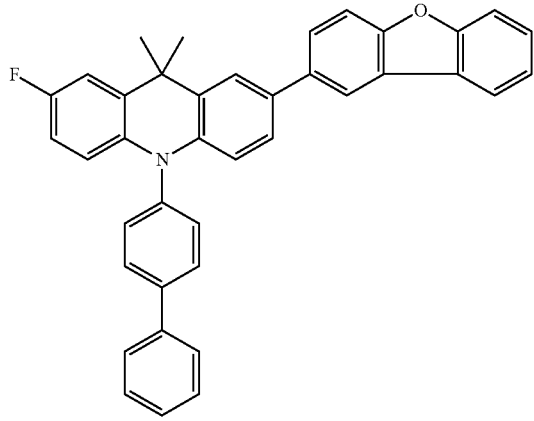
52
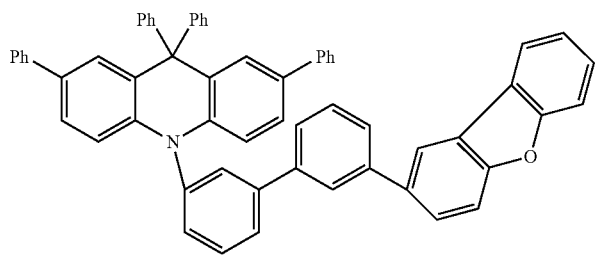
53
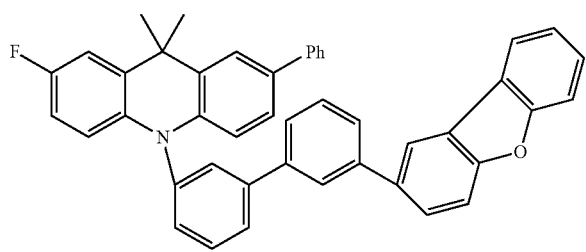 [SMILES: CC1(C)c2cc(F)ccc2N(c2cccc(-c3cccc(-c4ccc5oc6ccccc6c5c4)c3)c2)c2ccc(-c3ccccc3)cc21]
54
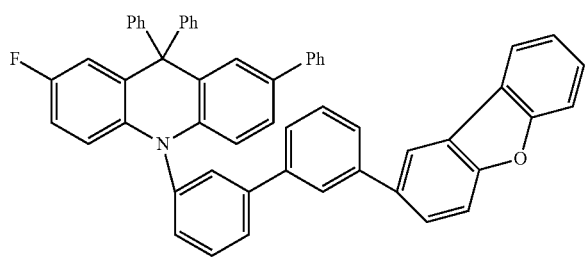
55
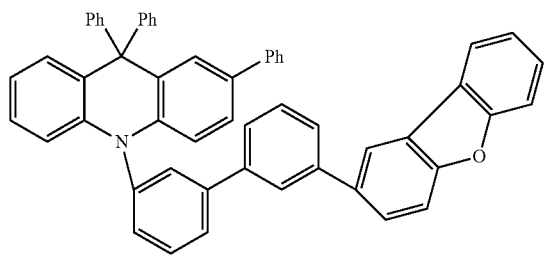
56

-continued
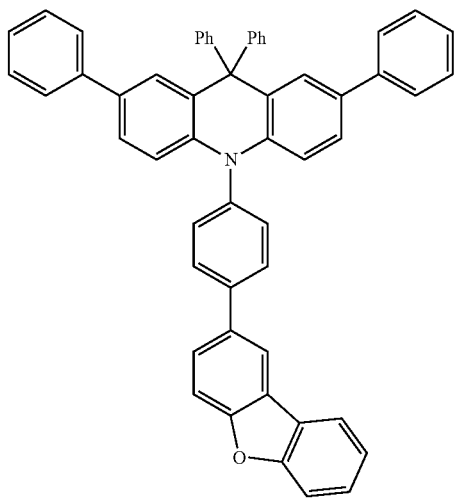 [SMILES: c1ccc(-c2ccc3c(c2)C(c2ccccc2)(c2ccccc2)c2cc(-c4ccccc4)ccc2N3c2ccc(-c3ccc4oc5ccccc5c4c3)cc2)cc1]
57
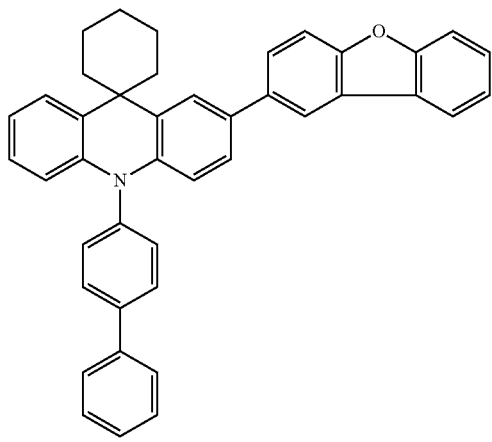 [SMILES: c1ccc(-c2ccc(N3c4ccccc4C4(CCCCC4)c4cc(-c5ccc6oc7ccccc7c6c5)ccc43)cc2)cc1]
58
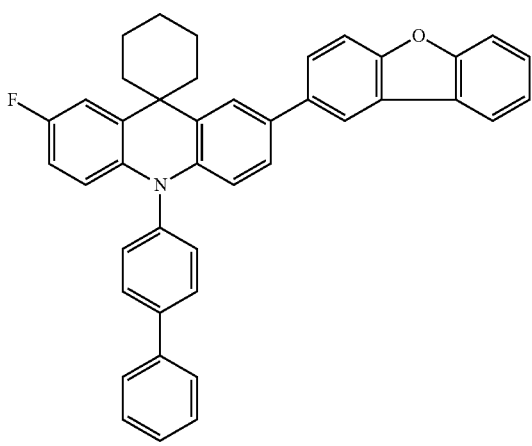 [SMILES: Fc1ccc2c(c1)C1(CCCCC1)c1cc(-c3ccc4oc5ccccc5c4c3)ccc1N2c1ccc(-c2ccccc2)cc1]
59

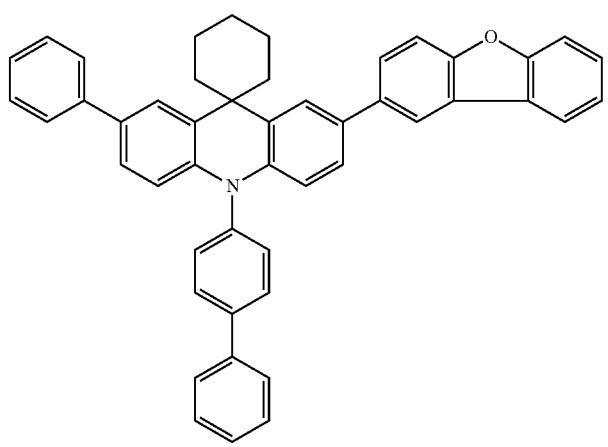
60
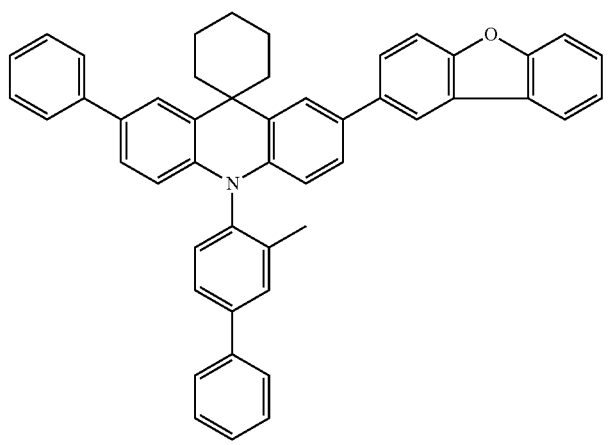 [SMILES: Cc1cc(-c2ccccc2)ccc1N1c2ccc(-c3ccccc3)cc2C2(CCCCC2)c2cc(-c3ccc4oc5ccccc5c4c3)ccc21]
61
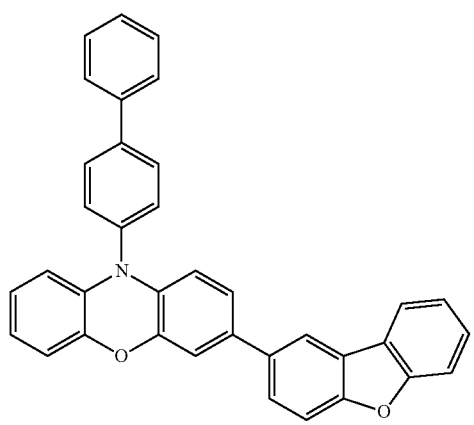 [SMILES: c1ccc(-c2ccc(N3c4ccccc4Oc4cc(-c5ccc6oc7ccccc7c6c5)ccc43)cc2)cc1]
62

-continued
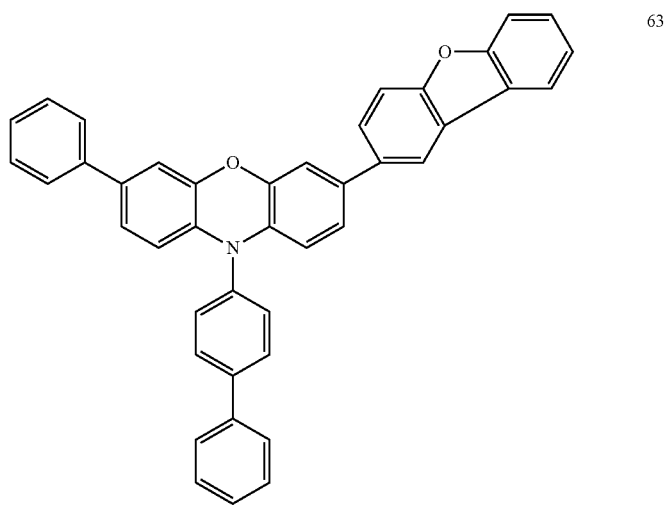
63
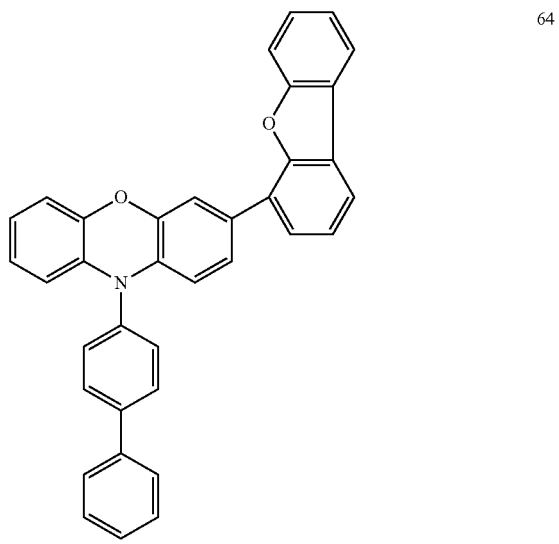
64
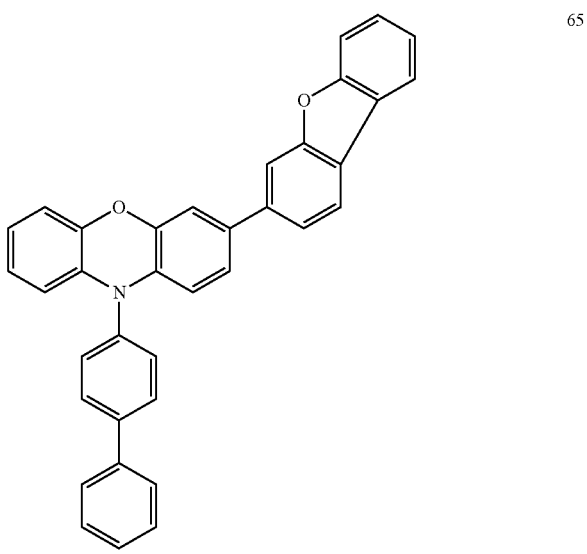
65

-continued
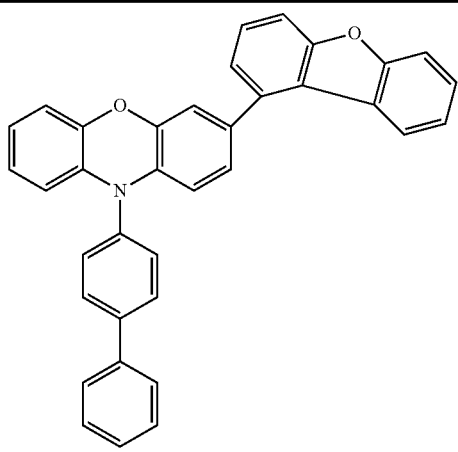
66
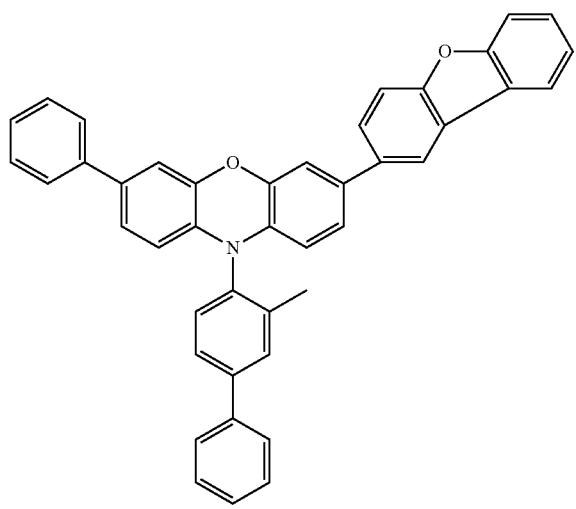
67
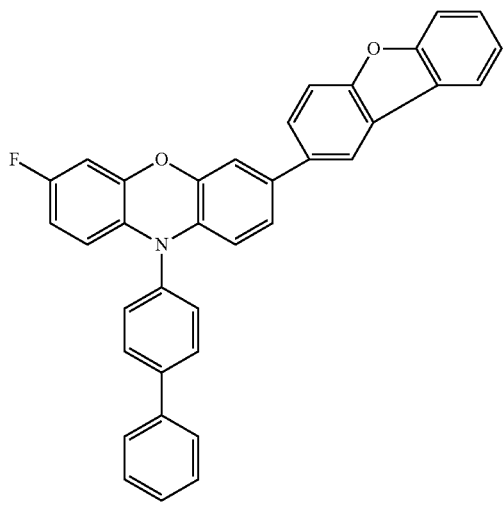 [SMILES: Fc1ccc2c(c1)Oc1cc(-c3ccc4oc5ccccc5c4c3)ccc1N2c1ccc(-c2ccccc2)cc1]
68

69
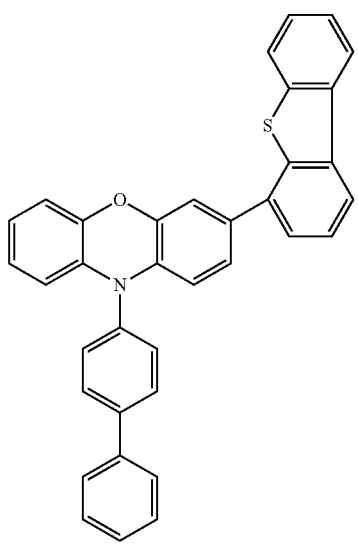 [SMILES: c1ccc(-c2ccc(N3c4ccccc4Oc4cc(-c5cccc6c5sc5ccccc56)ccc43)cc2)cc1]
70
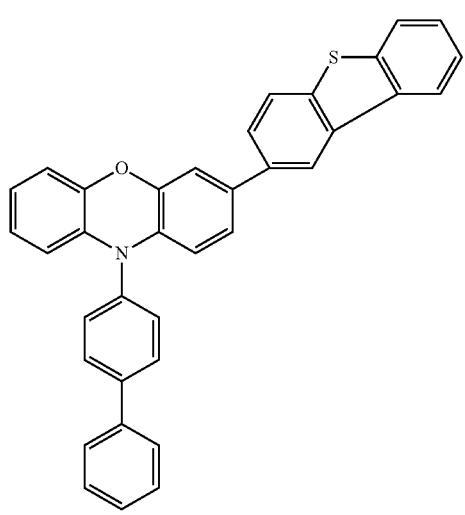 [SMILES: c1ccc(-c2ccc(N3c4ccccc4Oc4cc(-c5ccc6sc7ccccc7c6c5)ccc43)cc2)cc1]
71
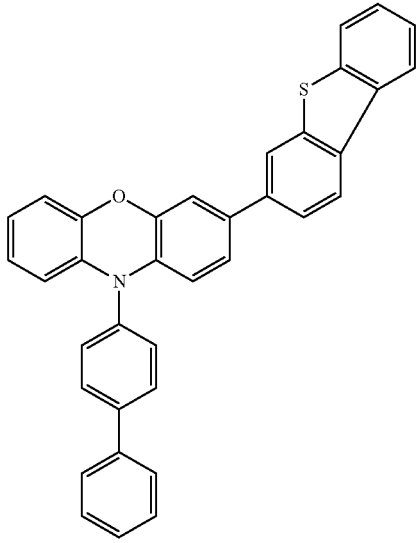 [SMILES: c1ccc(-c2ccc(N3c4ccccc4Oc4cc(-c5ccc6c(c5)sc5ccccc56)ccc43)cc2)cc1]

-continued
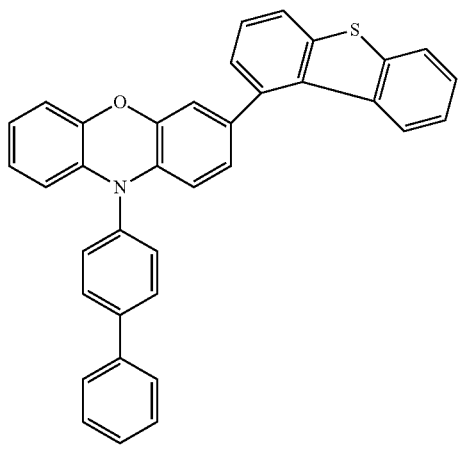 [SMILES: c1ccc(-c2ccc(N3c4ccccc4Oc4cc(-c5cccc6sc7ccccc7c56)ccc43)cc2)cc1]
72
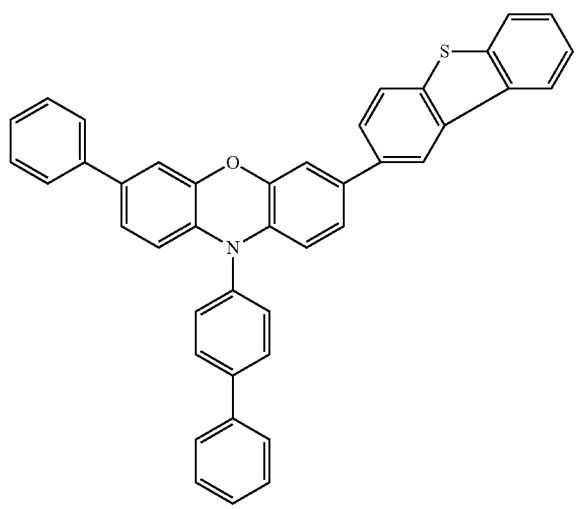
73
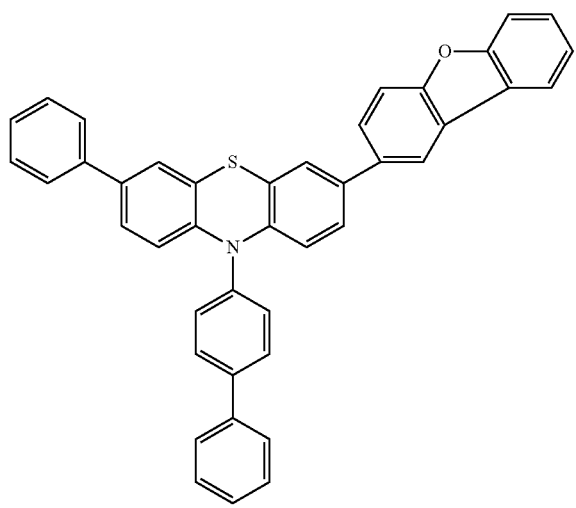
74

-continued
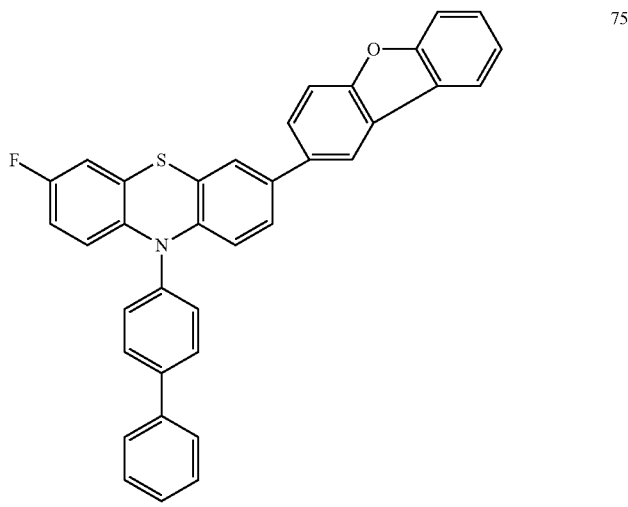
75
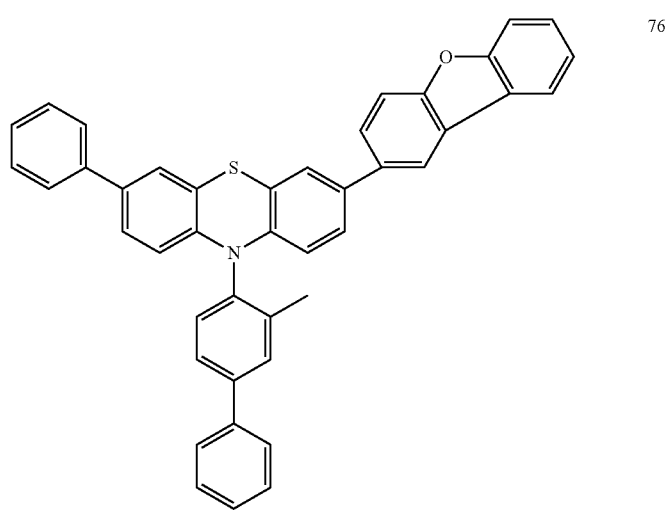
76
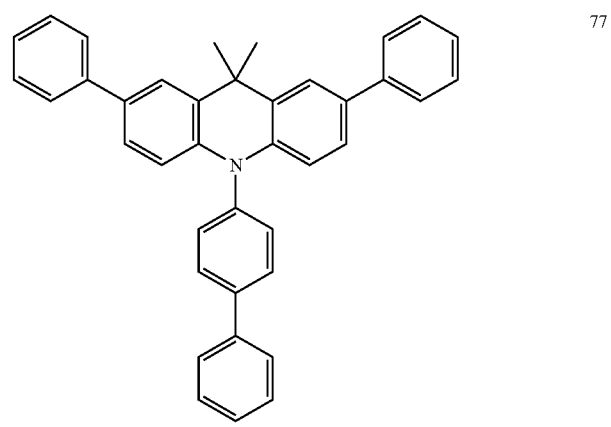
77

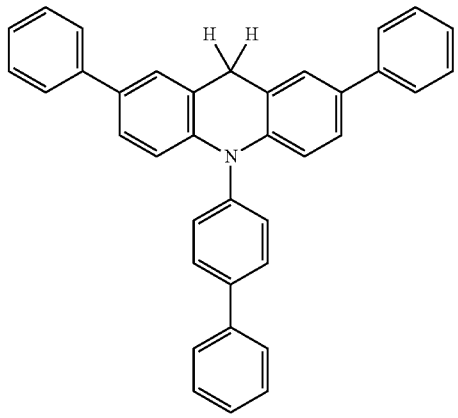 [SMILES: c1ccc(-c2ccc(N3c4ccc(-c5ccccc5)cc4Cc4cc(-c5ccccc5)ccc43)cc2)cc1]
78
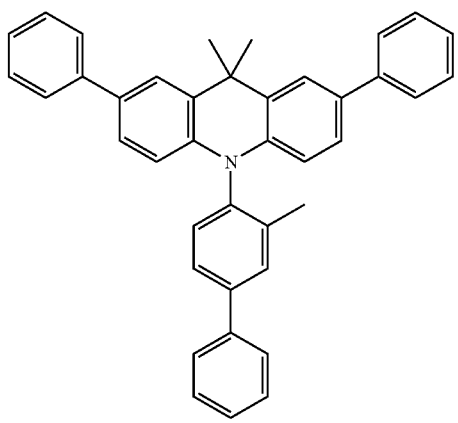 [SMILES: Cc1cc(-c2ccccc2)ccc1N1c2ccc(-c3ccccc3)cc2C(C)(C)c2cc(-c3ccccc3)ccc21]
79
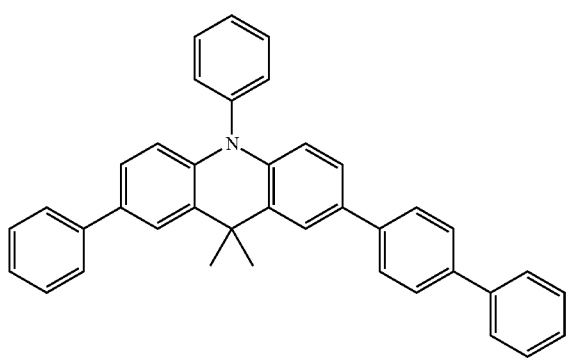 [SMILES: CC1(C)c2cc(-c3ccccc3)ccc2N(c2ccccc2)c2ccc(-c3ccc(-c4ccccc4)cc3)cc21]
80
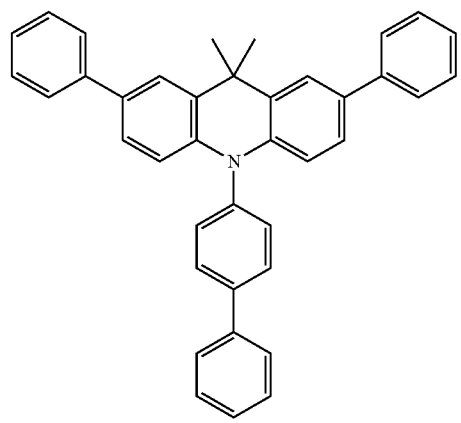 [SMILES: CC1(C)c2cc(-c3ccccc3)ccc2N(c2ccc(-c3ccccc3)cc2)c2ccc(-c3ccccc3)cc21]
81

-continued
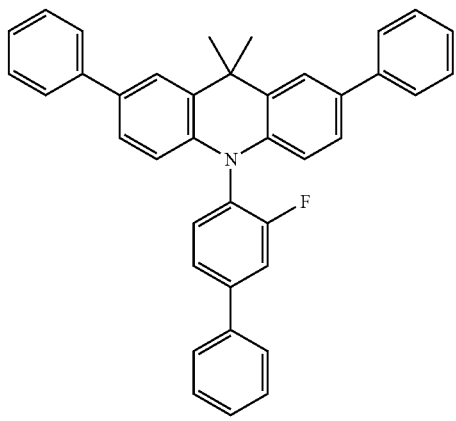 [SMILES: CC1(C)c2cc(-c3ccccc3)ccc2N(c2ccc(-c3ccccc3)cc2F)c2ccc(-c3ccccc3)cc21]
82
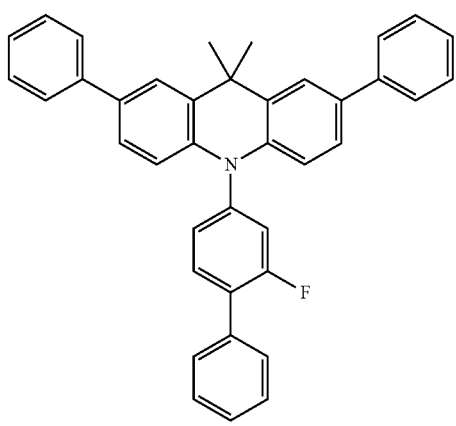 [SMILES: CC1(C)c2cc(-c3ccccc3)ccc2N(c2ccc(-c3ccccc3)c(F)c2)c2ccc(-c3ccccc3)cc21]
83
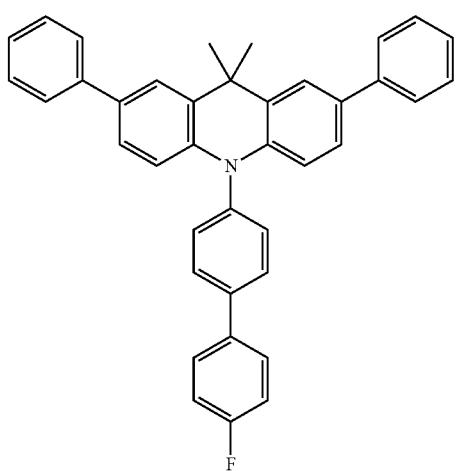 [SMILES: CC1(C)c2cc(-c3ccccc3)ccc2N(c2ccc(-c3ccc(F)cc3)cc2)c2ccc(-c3ccccc3)cc21]
84

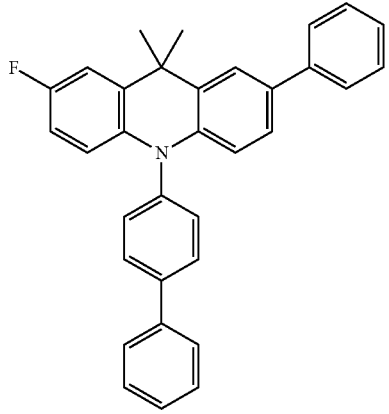 [SMILES: CC1(C)c2cc(F)ccc2N(c2ccc(-c3ccccc3)cc2)c2ccc(-c3ccccc3)cc21]
85
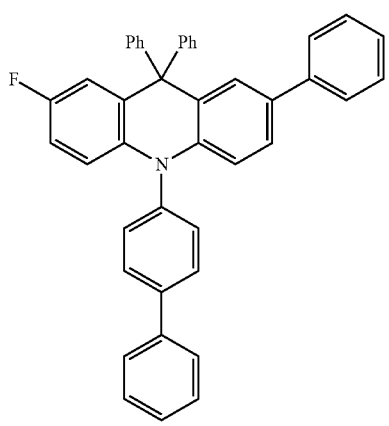 [SMILES: Fc1ccc2c(c1)C(c1ccccc1)(c1ccccc1)c1cc(-c3ccccc3)ccc1N2c1ccc(-c2ccccc2)cc1]
86
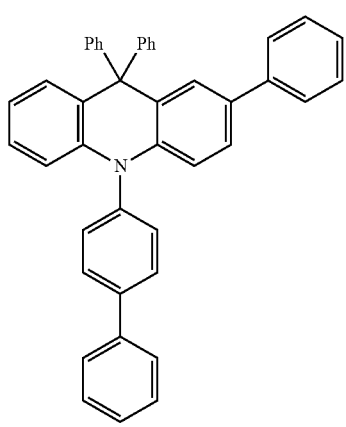 [SMILES: c1ccc(-c2ccc(N3c4ccccc4C(c4ccccc4)(c4ccccc4)c4cc(-c5ccccc5)ccc43)cc2)cc1]
87

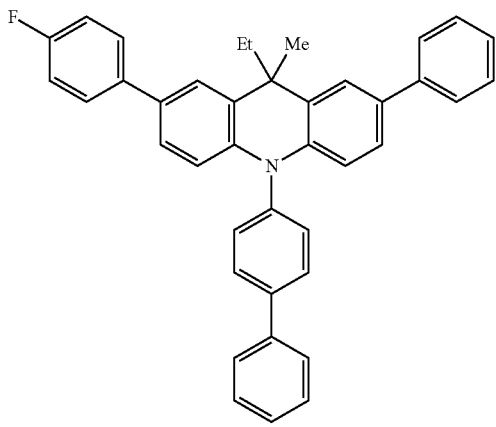 [SMILES: CCC1(C)c2cc(-c3ccccc3)ccc2N(c2ccc(-c3ccccc3)cc2)c2ccc(-c3ccc(F)cc3)cc21]
88
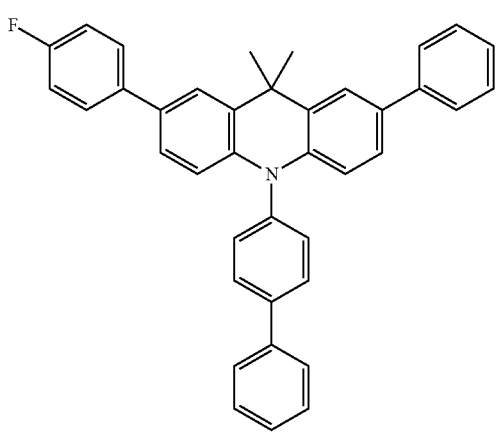 [SMILES: CC1(C)c2cc(-c3ccccc3)ccc2N(c2ccc(-c3ccccc3)cc2)c2ccc(-c3ccc(F)cc3)cc21]
89
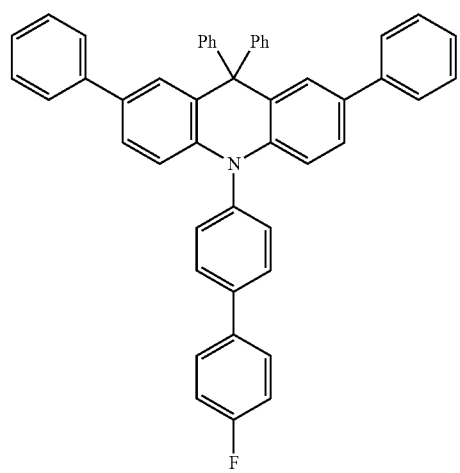 [SMILES: Fc1ccc(-c2ccc(N3c4ccc(-c5ccccc5)cc4C(c4ccccc4)(c4ccccc4)c4cc(-c5ccccc5)ccc43)cc2)cc1]
90

-continued
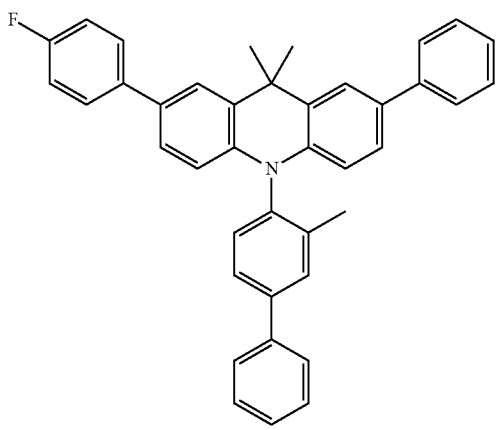 [SMILES: Cc1cc(-c2ccccc2)ccc1N1c2ccc(-c3ccccc3)cc2C(C)(C)c2cc(-c3ccc(F)cc3)ccc21]
91
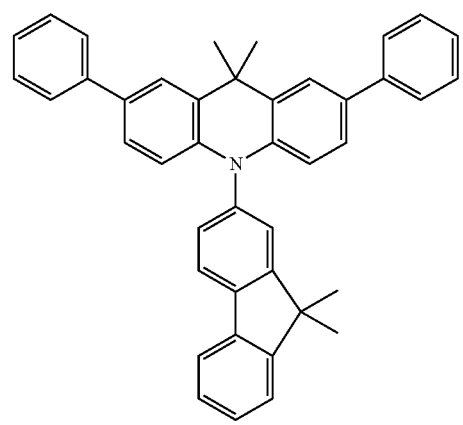 [SMILES: CC1(C)c2ccccc2-c2ccc(N3c4ccc(-c5ccccc5)cc4C(C)(C)c4cc(-c5ccccc5)ccc43)cc21]
92
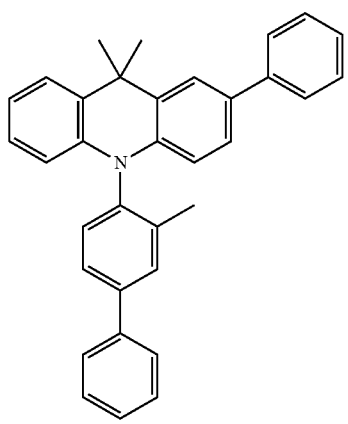 [SMILES: Cc1cc(-c2ccccc2)ccc1N1c2ccccc2C(C)(C)c2cc(-c3ccccc3)ccc21]
93

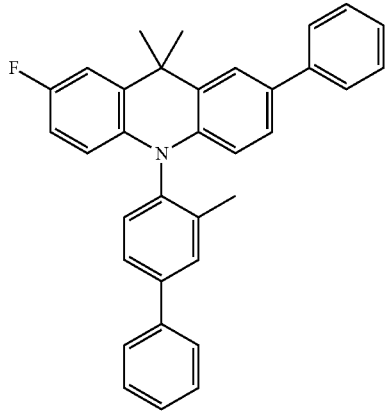 [SMILES: Cc1cc(-c2ccccc2)ccc1N1c2ccc(F)cc2C(C)(C)c2cc(-c3ccccc3)ccc21]
94
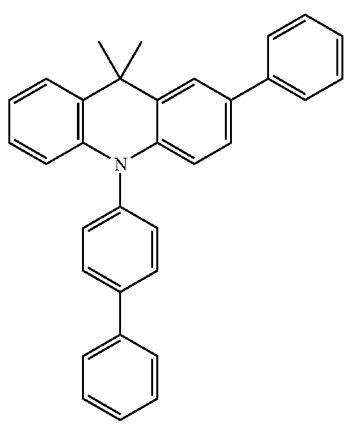 [SMILES: CC1(C)c2ccccc2N(c2ccc(-c3ccccc3)cc2)c2ccc(-c3ccccc3)cc21]
95
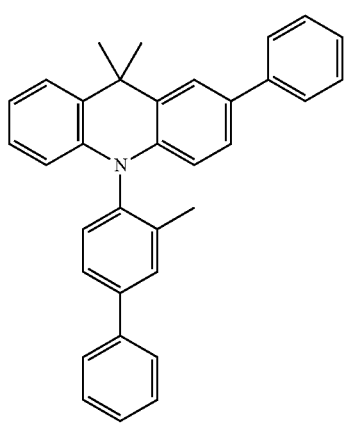 [SMILES: Cc1cc(-c2ccccc2)ccc1N1c2ccccc2C(C)(C)c2cc(-c3ccccc3)ccc21]
96

-continued
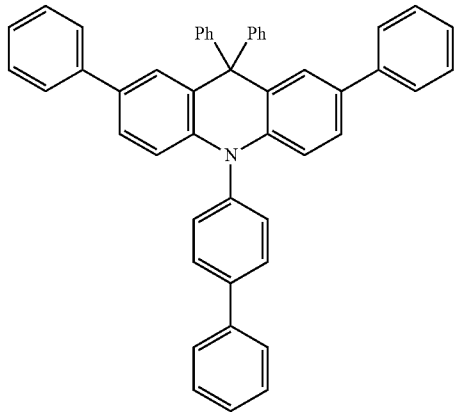
97
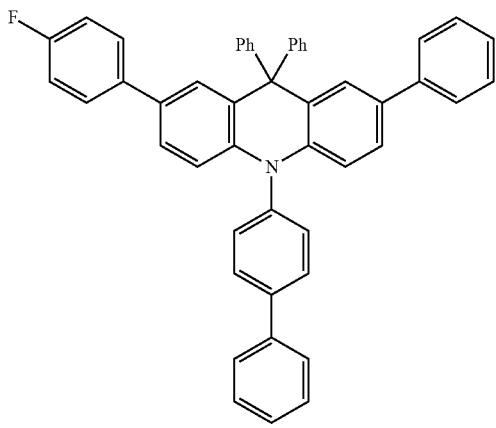
98
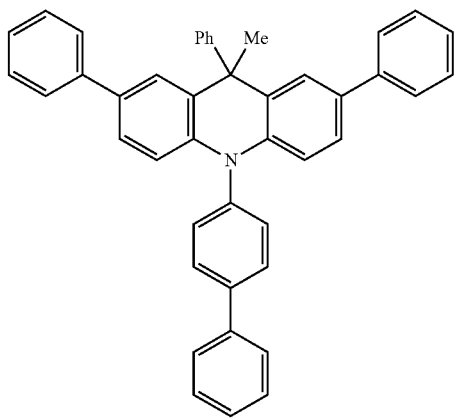
99

-continued
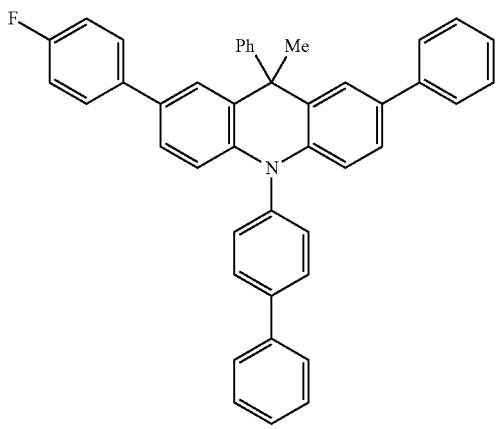 [SMILES: Fc1ccc(-c2ccc3c(c2)C(c2ccccc2)(c2ccccc2)c2cc(-c4ccccc4)ccc2N3c2ccc(-c3ccccc3)cc2)cc1]
100
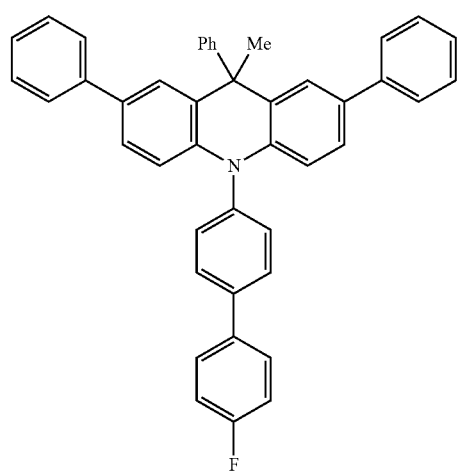 [SMILES: CC1(c2ccccc2)c2cc(-c3ccccc3)ccc2N(c2ccc(-c3ccc(F)cc3)cc2)c2ccc(-c3ccccc3)cc21]
101
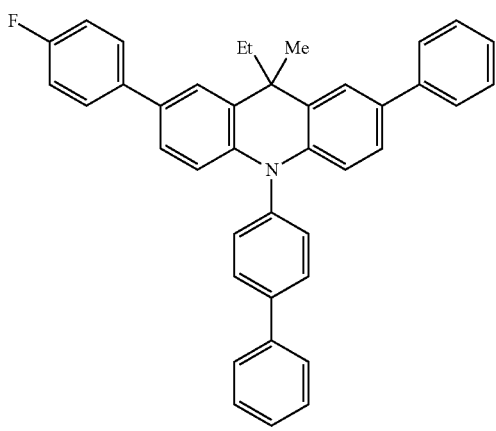 [SMILES: CCC1(C)c2cc(-c3ccccc3)ccc2N(c2ccc(-c3ccccc3)cc2)c2ccc(-c3ccc(F)cc3)cc21]
102

-continued
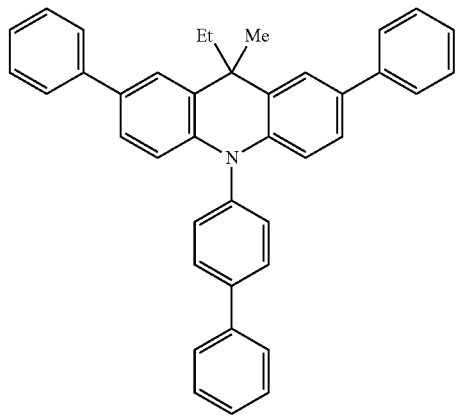 [SMILES: CCC1(C)c2cc(-c3ccccc3)ccc2N(c2ccc(-c3ccccc3)cc2)c2ccc(-c3ccccc3)cc21]
103
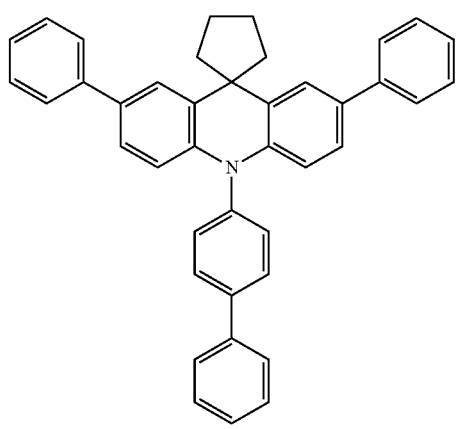 [SMILES: c1ccc(-c2ccc(N3c4ccc(-c5ccccc5)cc4C4(CCCC4)c4cc(-c5ccccc5)ccc43)cc2)cc1]
104
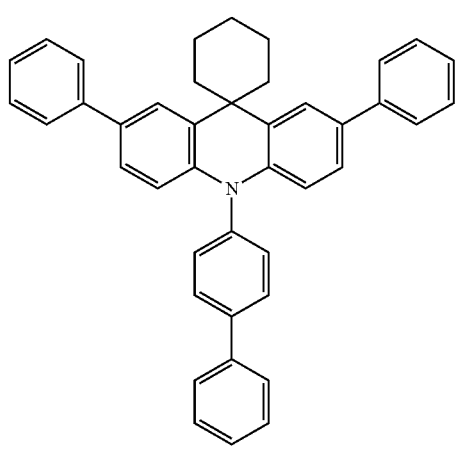 [SMILES: c1ccc(-c2ccc(N3c4ccc(-c5ccccc5)cc4C4(CCCCC4)c4cc(-c5ccccc5)ccc43)cc2)cc1]
105

-continued
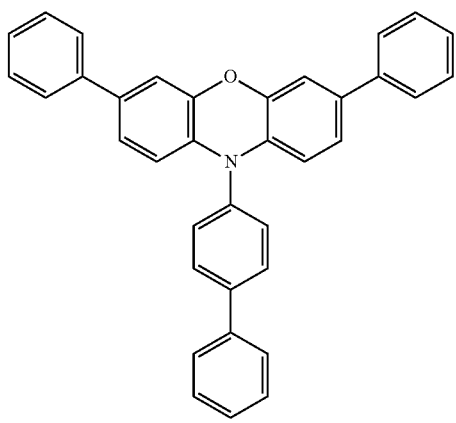 [SMILES: c1ccc(-c2ccc(N3c4ccc(-c5ccccc5)cc4Oc4cc(-c5ccccc5)ccc43)cc2)cc1]
106
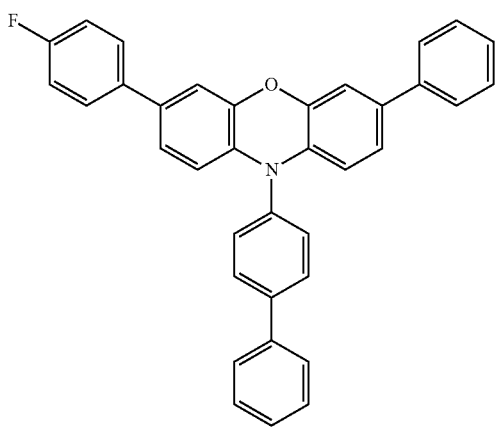
107
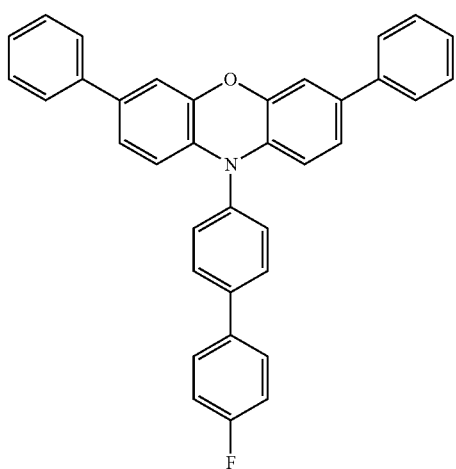 [SMILES: Fc1ccc(-c2ccc(N3c4ccc(-c5ccccc5)cc4Oc4cc(-c5ccccc5)ccc43)cc2)cc1]
108

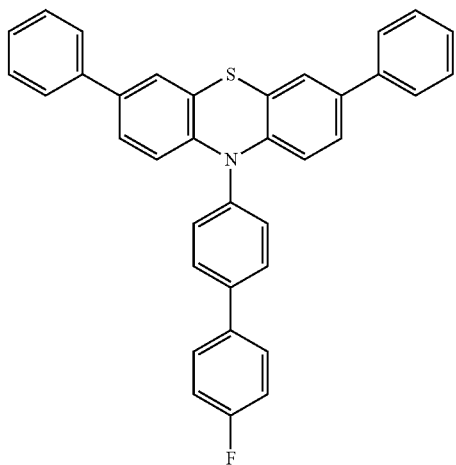 [SMILES: Fc1ccc(-c2ccc(N3c4ccc(-c5ccccc5)cc4Sc4cc(-c5ccccc5)ccc43)cc2)cc1]
109
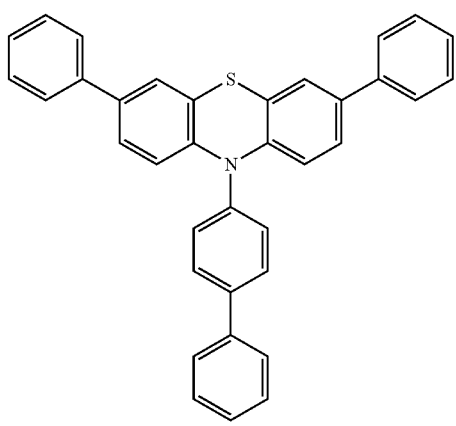 [SMILES: c1ccc(-c2ccc(N3c4ccc(-c5ccccc5)cc4Sc4cc(-c5ccccc5)ccc43)cc2)cc1]
110
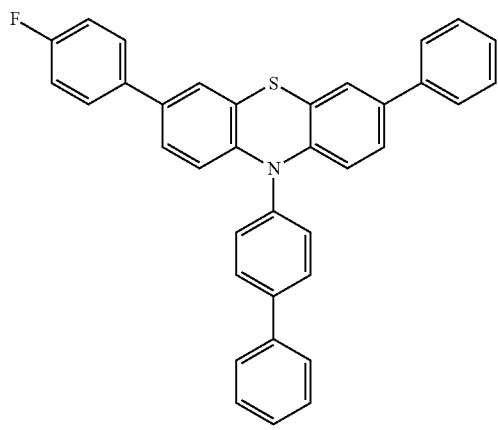
111

-continued
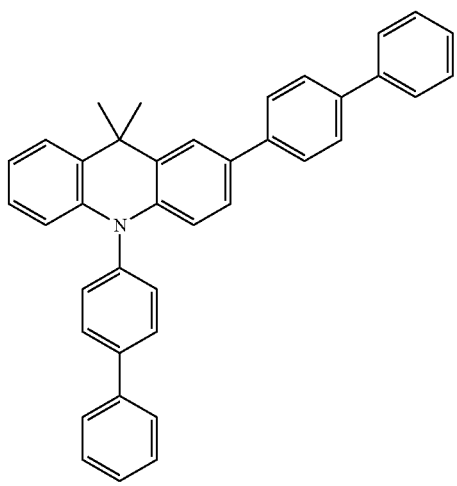 [SMILES: CC1(C)c2ccccc2N(c2ccc(-c3ccccc3)cc2)c2ccc(-c3ccc(-c4ccccc4)cc3)cc21]
112
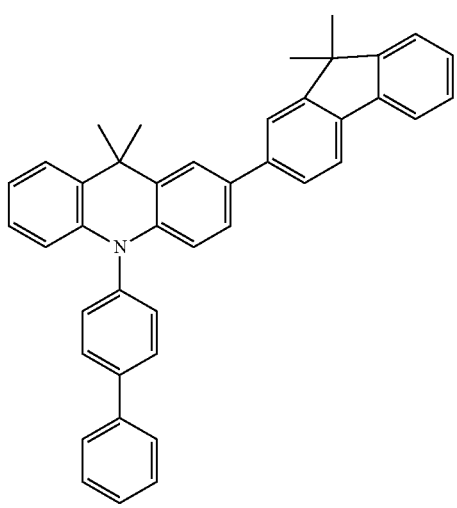 [SMILES: CC1(C)c2ccccc2-c2ccc(-c3ccc4c(c3)C(C)(C)c3ccccc3N4c3ccc(-c4ccccc4)cc3)cc21]
113
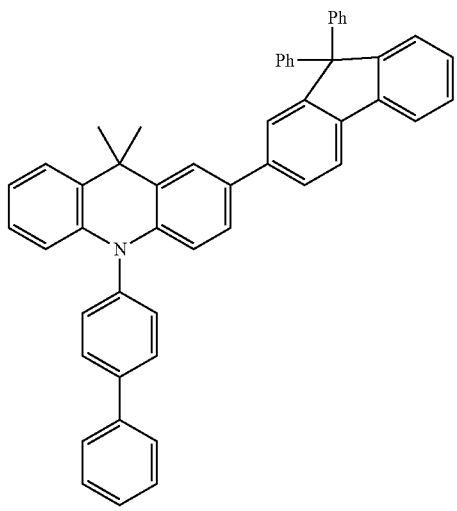 [SMILES: CC1(C)c2ccccc2N(c2ccc(-c3ccccc3)cc2)c2ccc(-c3ccc4c(c3)C(c3ccccc3)(c3ccccc3)c3ccccc3-4)cc21]
114

-continued
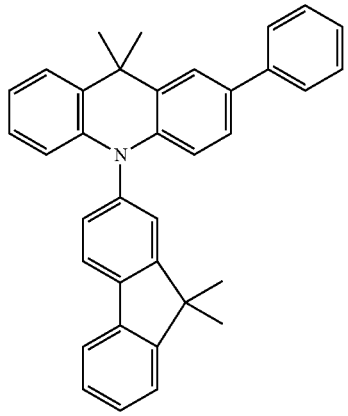 [SMILES: CC1(C)c2ccccc2-c2ccc(N3c4ccccc4C(C)(C)c4cc(-c5ccccc5)ccc43)cc21]
115
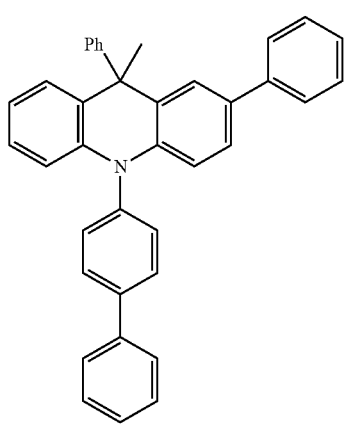 [SMILES: CC1(c2ccccc2)c2ccccc2N(c2ccc(-c3ccccc3)cc2)c2ccc(-c3ccccc3)cc21]
116
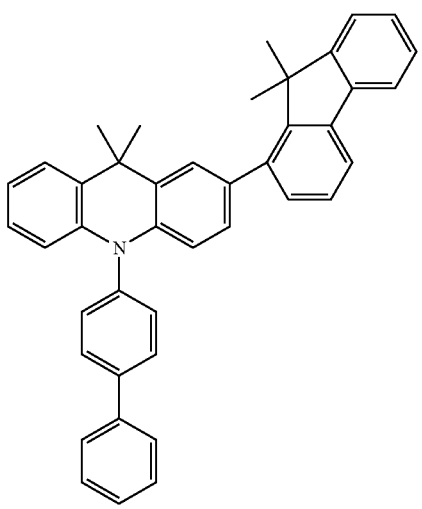 [SMILES: CC1(C)c2ccccc2N(c2ccc(-c3ccccc3)cc2)c2ccc(-c3cccc4c3C(C)(C)c3ccccc3-4)cc21]
117

118
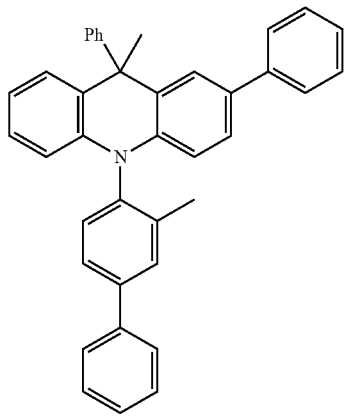 [SMILES: Cc1cc(-c2ccccc2)ccc1N1c2ccccc2C(C)(c2ccccc2)c2cc(-c3ccccc3)ccc21]
119
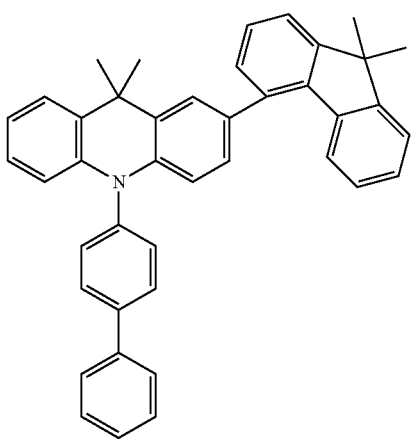 [SMILES: CC1(C)c2ccccc2N(c2ccc(-c3ccccc3)cc2)c2ccc(-c3cccc4c3-c3ccccc3C4(C)C)cc21]
120
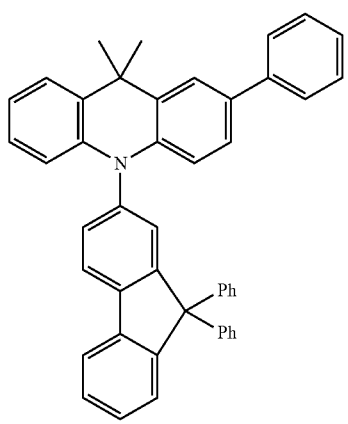 [SMILES: CC1(C)c2ccccc2N(c2ccc3c(c2)C(c2ccccc2)(c2ccccc2)c2ccccc2-3)c2ccc(-c3ccccc3)cc21]

-continued
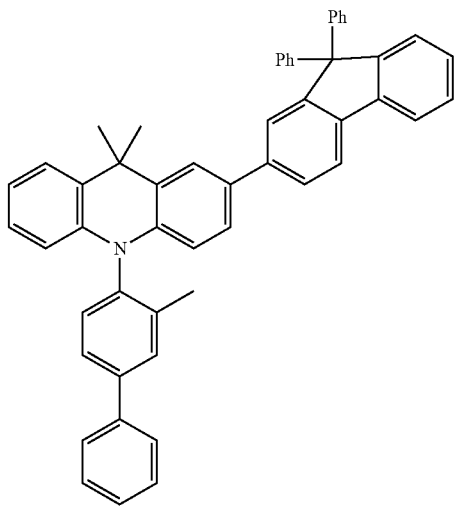 [SMILES: Cc1cc(-c2ccccc2)ccc1N1c2ccccc2C(C)(C)c2cc(-c3ccc4c(c3)C(c3ccccc3)(c3ccccc3)c3ccccc3-4)ccc21]
121
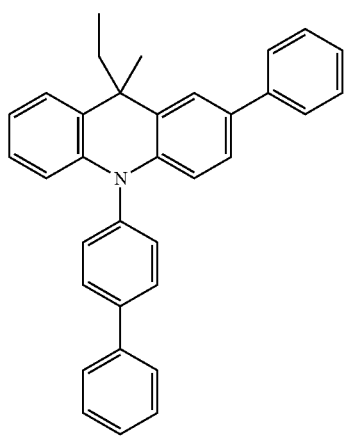 [SMILES: CCC1(C)c2ccccc2N(c2ccc(-c3ccccc3)cc2)c2ccc(-c3ccccc3)cc21]
122
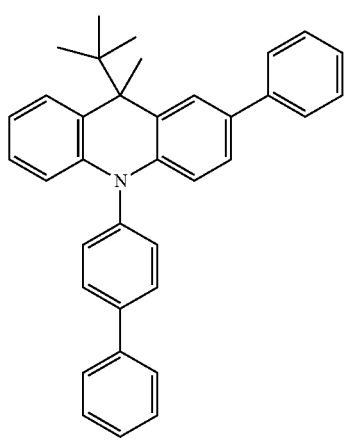 [SMILES: CC(C)(C)C1(C)c2ccccc2N(c2ccc(-c3ccccc3)cc2)c2ccc(-c3ccccc3)cc21]
123

-continued
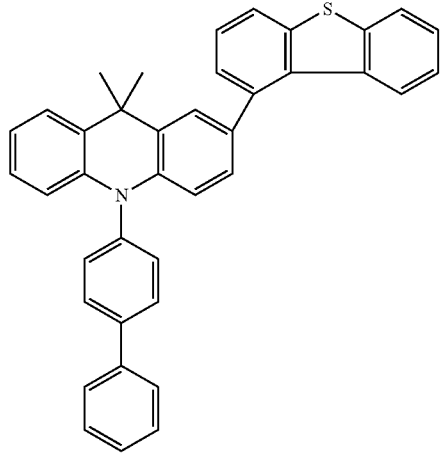 [SMILES: CC1(C)c2ccccc2N(c2ccc(-c3ccccc3)cc2)c2ccc(-c3cccc4sc5ccccc5c34)cc21]
124
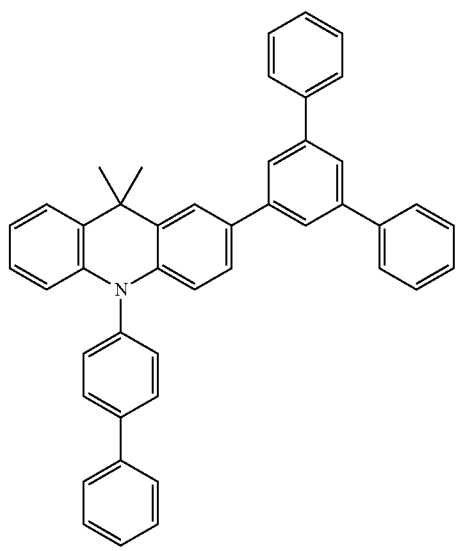 [SMILES: CC1(C)c2ccccc2N(c2ccc(-c3ccccc3)cc2)c2ccc(-c3cc(-c4ccccc4)cc(-c4ccccc4)c3)cc21]
125
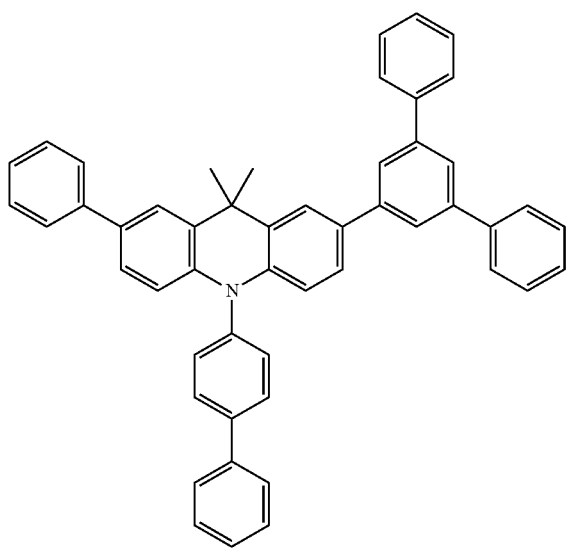 [SMILES: CC1(C)c2cc(-c3ccccc3)ccc2N(c2ccc(-c3ccccc3)cc2)c2ccc(-c3cc(-c4ccccc4)cc(-c4ccccc4)c3)cc21]
126

-continued
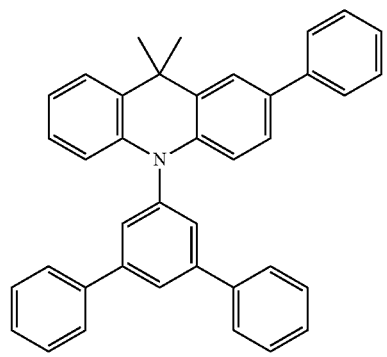 [SMILES: CC1(C)c2ccccc2N(c2cc(-c3ccccc3)cc(-c3ccccc3)c2)c2ccc(-c3ccccc3)cc21]
127
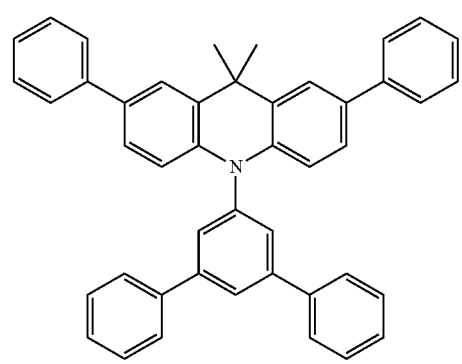 [SMILES: CC1(C)c2cc(-c3ccccc3)ccc2N(c2cc(-c3ccccc3)cc(-c3ccccc3)c2)c2ccc(-c3ccccc3)cc21]
128
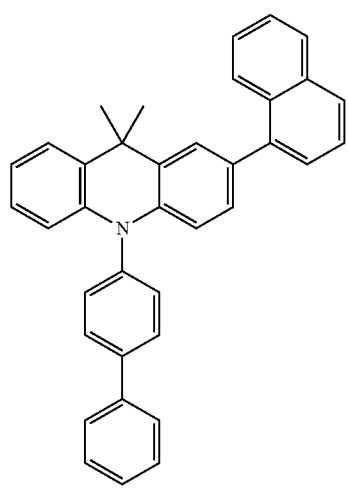 [SMILES: CC1(C)c2ccccc2N(c2ccc(-c3ccccc3)cc2)c2ccc(-c3cccc4ccccc34)cc21]
129

-continued
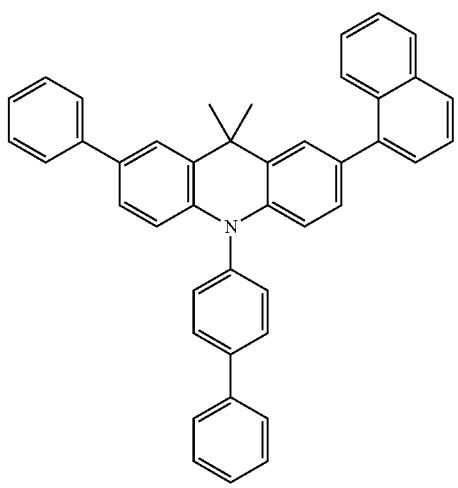 [SMILES: CC1(C)c2cc(-c3ccccc3)ccc2N(c2ccc(-c3ccccc3)cc2)c2ccc(-c3cccc4ccccc34)cc21]
130
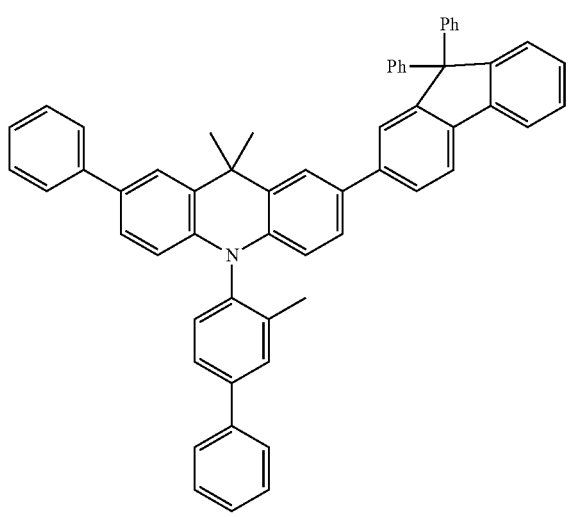 [SMILES: Cc1cc(-c2ccccc2)ccc1N1c2ccc(-c3ccccc3)cc2C(C)(C)c2cc(-c3ccc4c(c3)C(c3ccccc3)(c3ccccc3)c3ccccc3-4)ccc21]
131
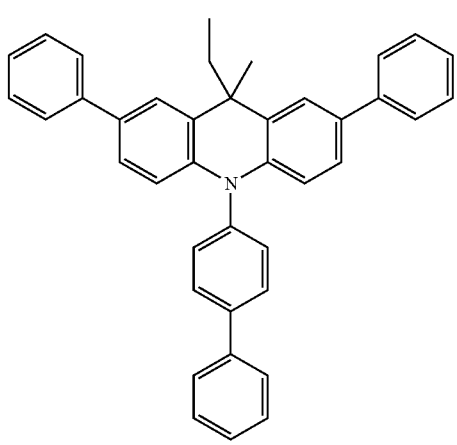 [SMILES: CCC1(C)c2cc(-c3ccccc3)ccc2N(c2ccc(-c3ccccc3)cc2)c2ccc(-c3ccccc3)cc21]
132

-continued
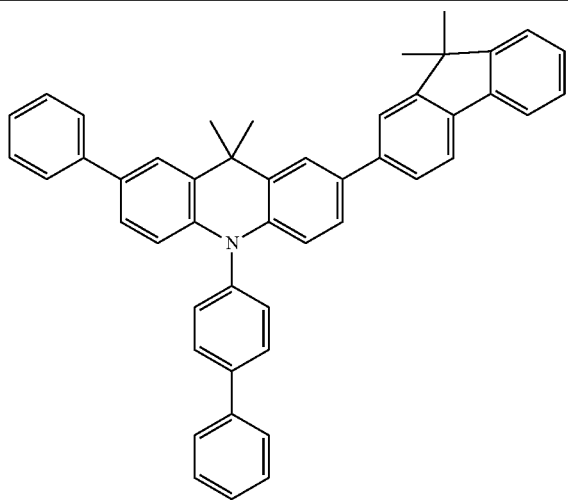
133
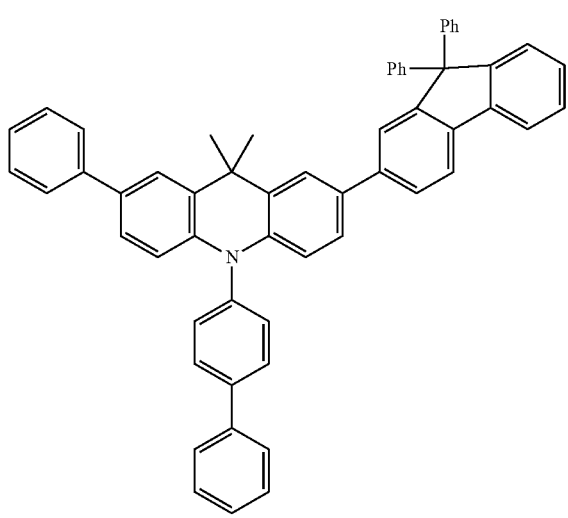 [SMILES: CC1(C)c2cc(-c3ccccc3)ccc2N(c2ccc(-c3ccccc3)cc2)c2ccc(-c3ccc4c(c3)C(c3ccccc3)(c3ccccc3)c3ccccc3-4)cc21]
134
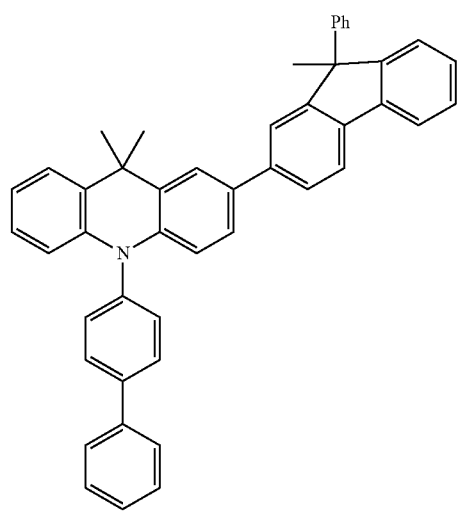 [SMILES: CC1(C)c2ccccc2N(c2ccc(-c3ccccc3)cc2)c2ccc(-c3ccc4c(c3)C(C)(c3ccccc3)c3ccccc3-4)cc21]
135

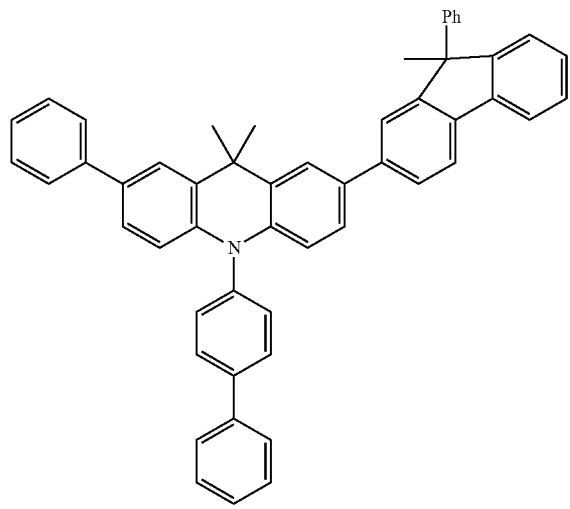 [SMILES: CC1(C)c2cc(-c3ccccc3)ccc2N(c2ccc(-c3ccccc3)cc2)c2ccc(-c3ccc4c(c3)C(C)(c3ccccc3)c3ccccc3-4)cc21]
136
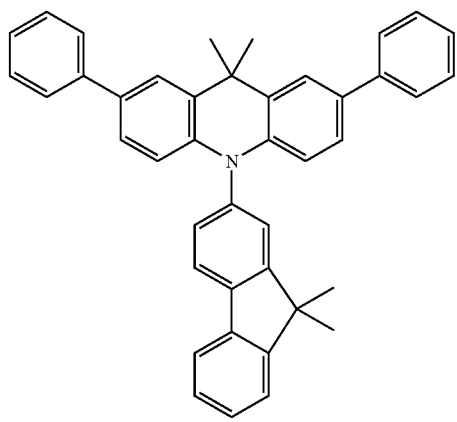 [SMILES: CC1(C)c2ccccc2-c2ccc(N3c4ccc(-c5ccccc5)cc4C(C)(C)c4cc(-c5ccccc5)ccc43)cc21]
137
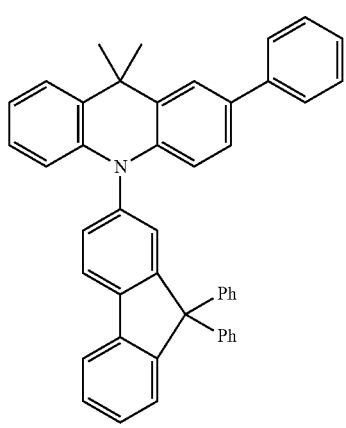 [SMILES: CC1(C)c2ccccc2N(c2ccc3c(c2)C(c2ccccc2)(c2ccccc2)c2ccccc2-3)c2ccc(-c3ccccc3)cc21]
138

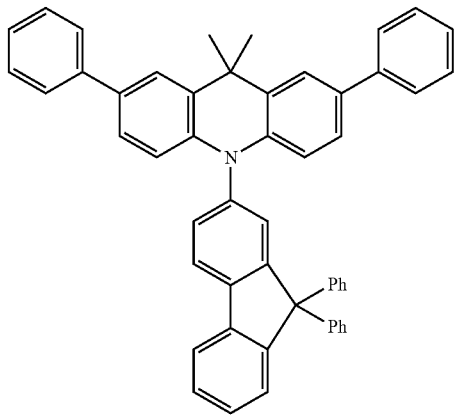 [SMILES: CC1(C)c2cc(-c3ccccc3)ccc2N(c2ccc3c(c2)C(c2ccccc2)(c2ccccc2)c2ccccc2-3)c2ccc(-c3ccccc3)cc21]
139
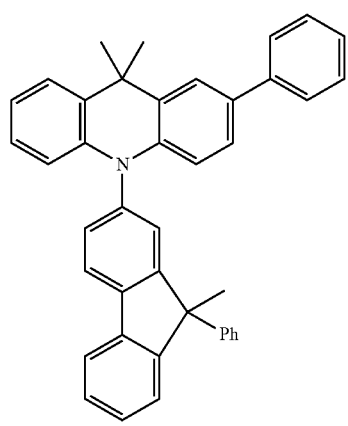 [SMILES: CC1(C)c2ccccc2N(c2ccc3c(c2)C(C)(c2ccccc2)c2ccccc2-3)c2ccc(-c3ccccc3)cc21]
140
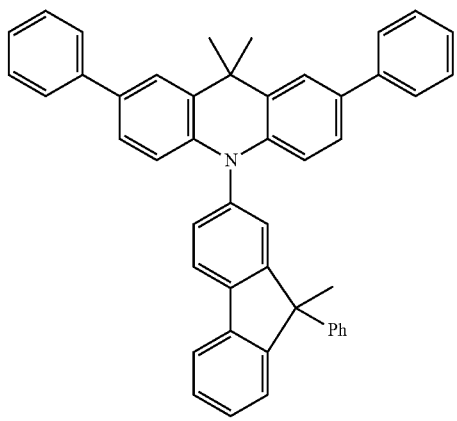 [SMILES: CC1(C)c2cc(-c3ccccc3)ccc2N(c2ccc3c(c2)C(C)(c2ccccc2)c2ccccc2-3)c2ccc(-c3ccccc3)cc21]
141

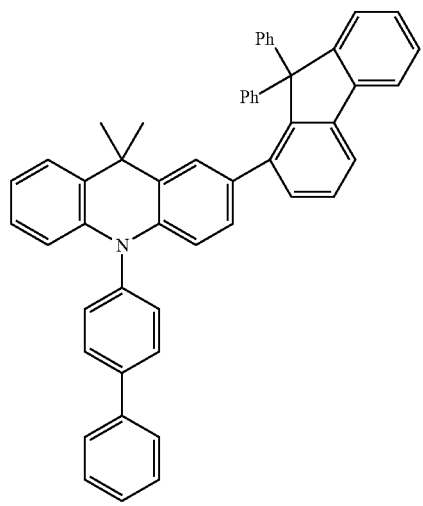 [SMILES: CC1(C)c2ccccc2N(c2ccc(-c3ccccc3)cc2)c2ccc(-c3cccc4c3C(c3ccccc3)(c3ccccc3)c3ccccc3-4)cc21]
142
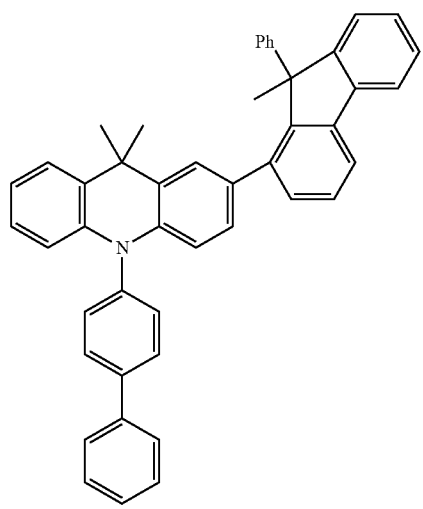 [SMILES: CC1(C)c2ccccc2N(c2ccc(-c3ccccc3)cc2)c2ccc(-c3cccc4c3C(C)(c3ccccc3)c3ccccc3-4)cc21]
143
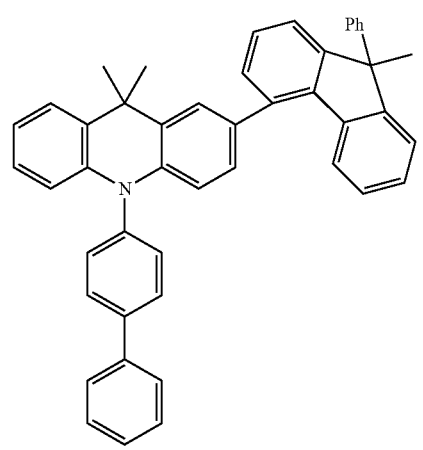 [SMILES: CC1(C)c2ccccc2N(c2ccc(-c3ccccc3)cc2)c2ccc(-c3cccc4c3-c3ccccc3C4(C)c3ccccc3)cc21]
144

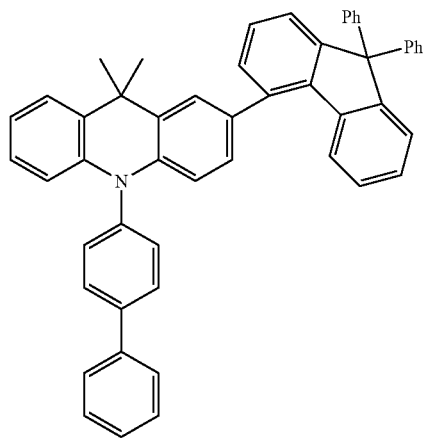 [SMILES: CC1(C)c2ccccc2N(c2ccc(-c3ccccc3)cc2)c2ccc(-c3cccc4c3-c3ccccc3C4(c3ccccc3)c3ccccc3)cc21]

145

The synthesis of the compounds according to the invention can be carried out by processes of preparative organic chemistry which are generally known to the person skilled in the art. Examples of reactions which are preferably employed are halogenations and transition metal-catalysed coupling reactions, preferably Suzuki couplings and Buchwald couplings.

A preferred process for the preparation of the compounds according to the invention starts from the basic structures depicted as starting materials in Scheme 1. These are in some cases commercially available, in other cases they can be prepared from simple, commercially available compounds in a few synthesis steps.

Scheme 1

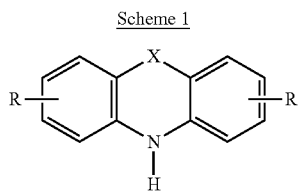

R = organic radical
X = CR$_2$, SiR$_2$, NR. PR, O, S

The compounds in accordance with Scheme 1 may already contain a halogen group or another reactive leaving group.

The compounds are firstly reacted with an aryl or heteroaryl compound ArY in a Buchwald coupling, which introduces the substituent on the nitrogen atom (Scheme 2).

Scheme 2

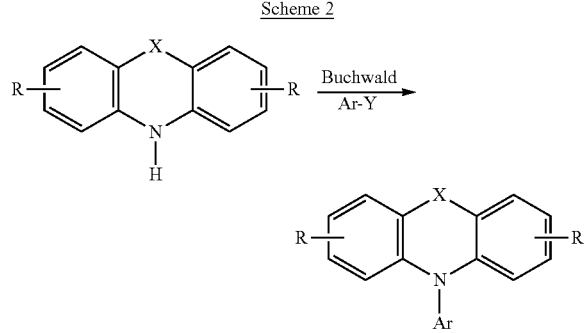

-continued

R = organic radical
X = CR$_2$, SiR$_2$, NR. PR, O, S
Ar = aryl, heteroaryl
Y = Hal or another reactive leaving group This is followed by a halogenation reaction on the dihydroacridine unit, so long as a halogen or other reactive group is not already present on this unit in the compound (Scheme 3).

Scheme 3

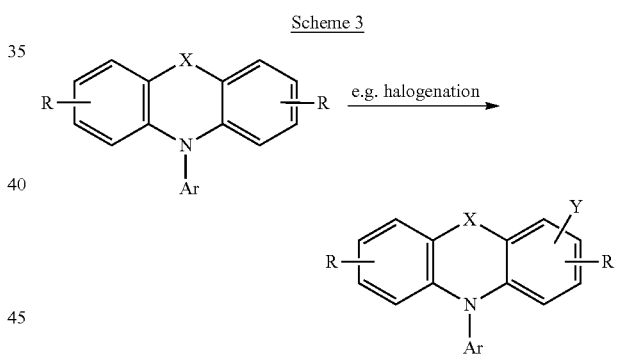

R = organic radical
X = CR$_2$, SiR$_2$, NR. PR, O, S
Ar = aryl, heteroaryl
Y = Hal or another reactive leaving group Instead of a single halogen or other leaving group, two or more such groups may also be introduced.

Finally, a further aryl or heteroaryl group is introduced into the compound at the position of the halogen or other leaving group via a Suzuki coupling (Scheme 4).

Scheme 4

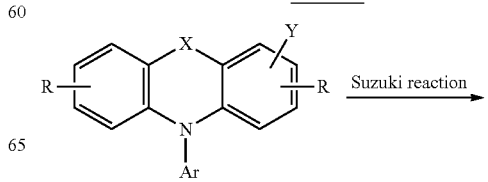

-continued

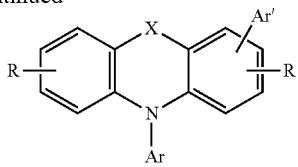

R = organic radical
X = CR$_2$, SiR$_2$, NR. PR, O, S
Ar, Ar' = aryl, heteroaryl
Y = Hal or another reactive leaving group The synthetic process shown above has an illustrative character and may be modified in a suitable manner by the person skilled in the art in the area of organic synthesis if this is advantageous for the synthesis of certain embodiments of compounds according to the invention.

The present invention thus furthermore relates to a process for the preparation of compounds of the formula (I) which is characterised in that one or more transition metal-catalysed coupling reactions by means of which aryl or heteroaryl groups are introduced as substituents are carried out starting from a dihydroacridine derivative. The transition metal-catalysed coupling reactions are preferably selected from Hartwig-Buchwald couplings and Suzuki couplings.

The compounds according to the invention described above, in particular compounds which are substituted by reactive leaving groups, such as bromine, iodine, chlorine, boronic acid or boronic acid ester, can be used as monomers for the preparation of corresponding oligomers, dendrimers or polymers. Suitable reactive leaving groups are, for example, bromine, iodine, chlorine, boronic acids, boronic acid esters, amines, alkenyl or alkynyl groups having a terminal C—C double bond or C—C triple bond, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formula (I), where the bond(s) to the polymer, oligomer or dendrimer can be localised at any desired positions in formula (I) which are substituted by R$^1$ or R$^2$. Depending on the linking of the compound of the formula (I), the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (I) may be linked via a trivalent or polyvalent group, for example via a trivalent or polyvalent aromatic or heteroaromatic group, to form a branched or dendritic oligomer or polymer.

The same preferences as described above for compounds of the formula (I) apply to the recurring units of the formula (I) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, of which at least one monomer results in recurring units of the formula (I) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the compounds according to the invention from liquid phase, for example by spin coating or by printing processes, formulations of the compounds according to the invention are necessary. These formulations can be, for example, solutions, dispersions or mini-emulsions. It may be preferred to use mixtures of two or more solvents for this purpose. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents.

The invention therefore furthermore relates to a formulation, in particular a solution, dispersion or mini-emulsion, comprising at least one compound of the formula (I) or at least one polymer, oligomer or dendrimer containing at least one unit of the formula (I) and at least one solvent, preferably an organic solvent. The way in which solutions of this type can be prepared is known to the person skilled in the art and is described, for example, in WO 2002/072714, WO 2003/019694 and the literature cited therein.

The compounds according to the invention are suitable for use in electronic devices, in particular in organic electroluminescent devices (OLEDs).

Depending on the substitution, the compounds are employed in different functions and layers.

The invention therefore furthermore relates to the use of the compounds of the formula (I) in electronic devices and to electronic devices themselves which comprise one or more compounds of the formula (I). The electronic devices here are preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (LECs), organic laser diodes (O-lasers) and particularly preferably organic electroluminescent devices (OLEDs).

The invention relates, as already stated, to electronic devices comprising at least one compound of the formula (I). The electronic devices are preferably selected from the devices mentioned above. Particular preference is given to organic electroluminescent devices (OLEDs) comprising anode, cathode and at least one emitting layer, characterised in that at least one organic layer, which may be an emitting layer, a hole-transport layer or another layer, comprises at least one compound of the formula (I).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where the three layers exhibit blue, green and orange or red emission (for the basic structure see, for example, WO 2005/011013). The compounds according to the invention may be present in a hole-transport layer, an emitting layer and/or in another layer in such devices. It should be noted that, for the generation of white light, one emitter compound used individually which emits in a broad wavelength range may also be suitable instead of a plurality of emitter compounds emitting in a colour.

It is preferred in accordance with the invention for the compound of the formula (I) to be employed in an electronic device comprising one or more phosphorescent dopants. The compound can be used in various layers here, preferably in an hole-transport layer, a hole-injection layer or in an emitting layer. However, the compound of the formula (I) can also be employed in accordance with the invention in an electronic device comprising one or more fluorescent dopants.

The term phosphorescent dopants typically encompasses compounds in which the light emission takes place by a spin-forbidden transition, for example a transition from an excited triplet state or a state having a relatively high spin quantum number, for example a quintet state.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art will also be able to employ further phosphorescent complexes without inventive step in combination with the compounds of the formula (I) in organic electroluminescent devices.

Explicit examples of suitable phosphorescent emitter compounds are furthermore revealed by the following table.

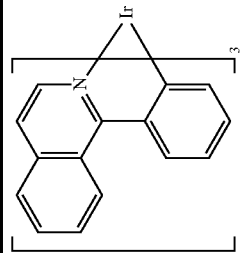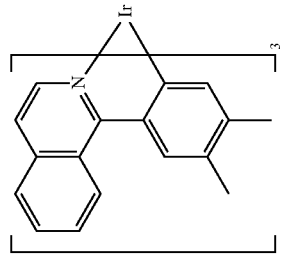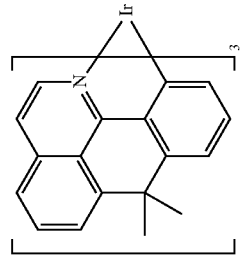
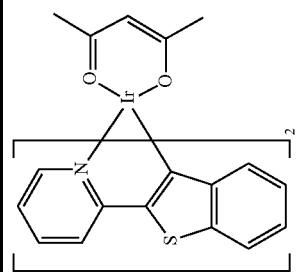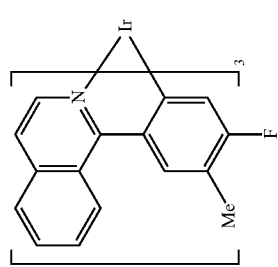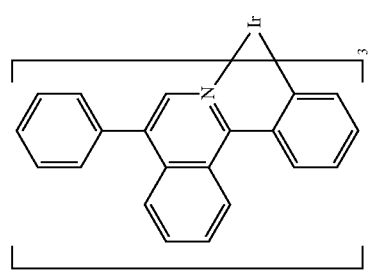
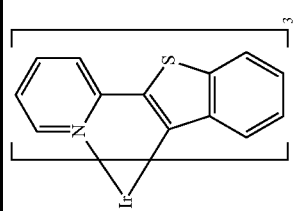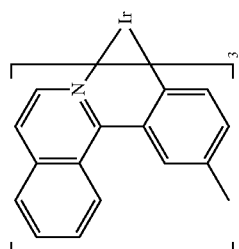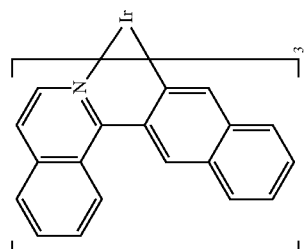

-continued
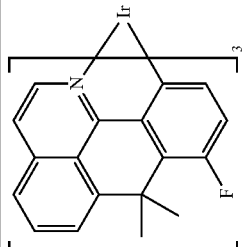 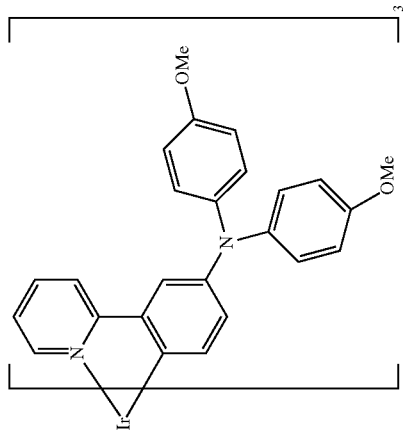 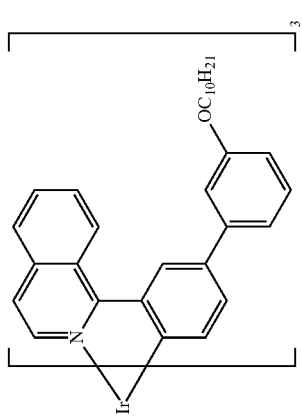
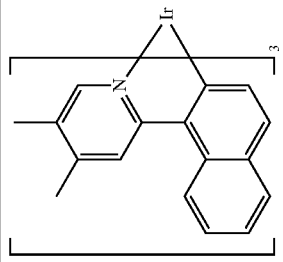 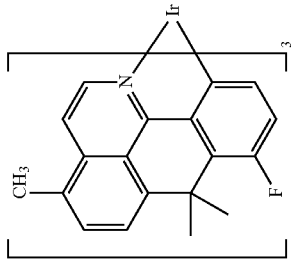 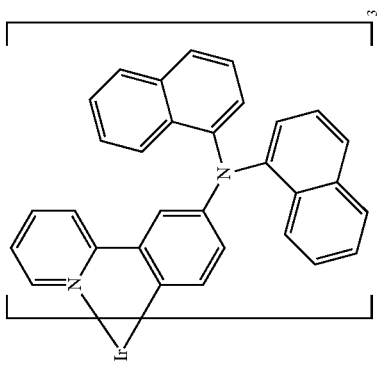
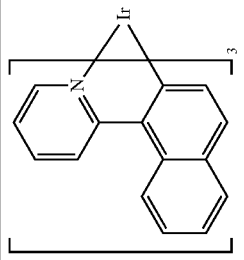 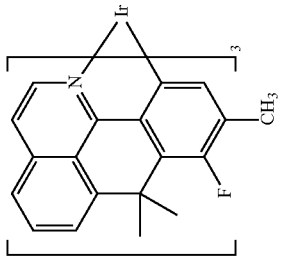 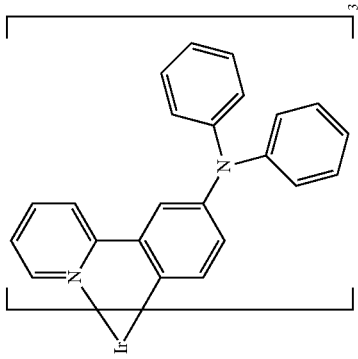

-continued
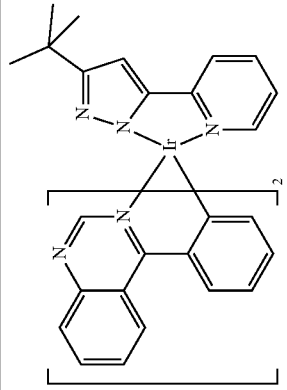
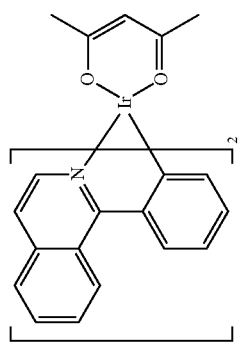
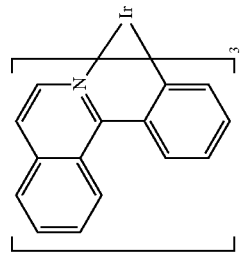
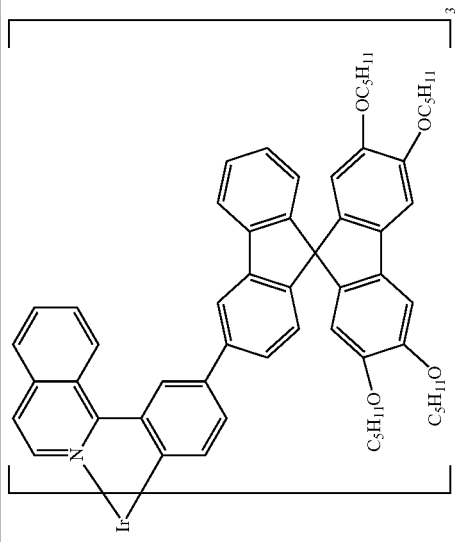
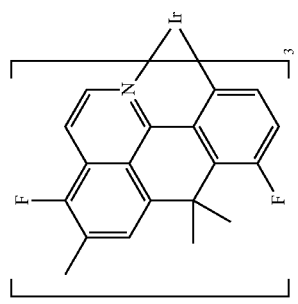
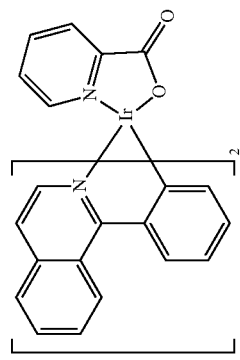
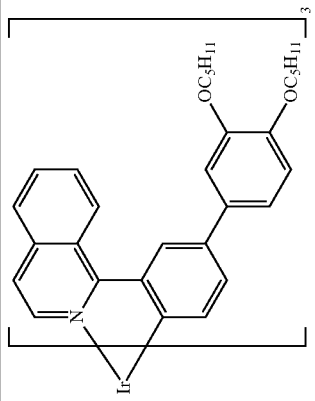
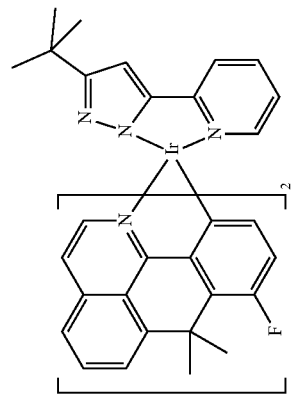
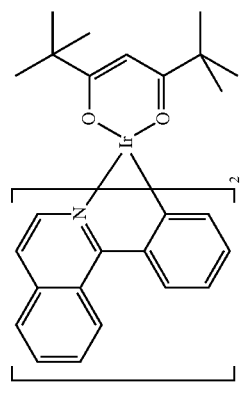

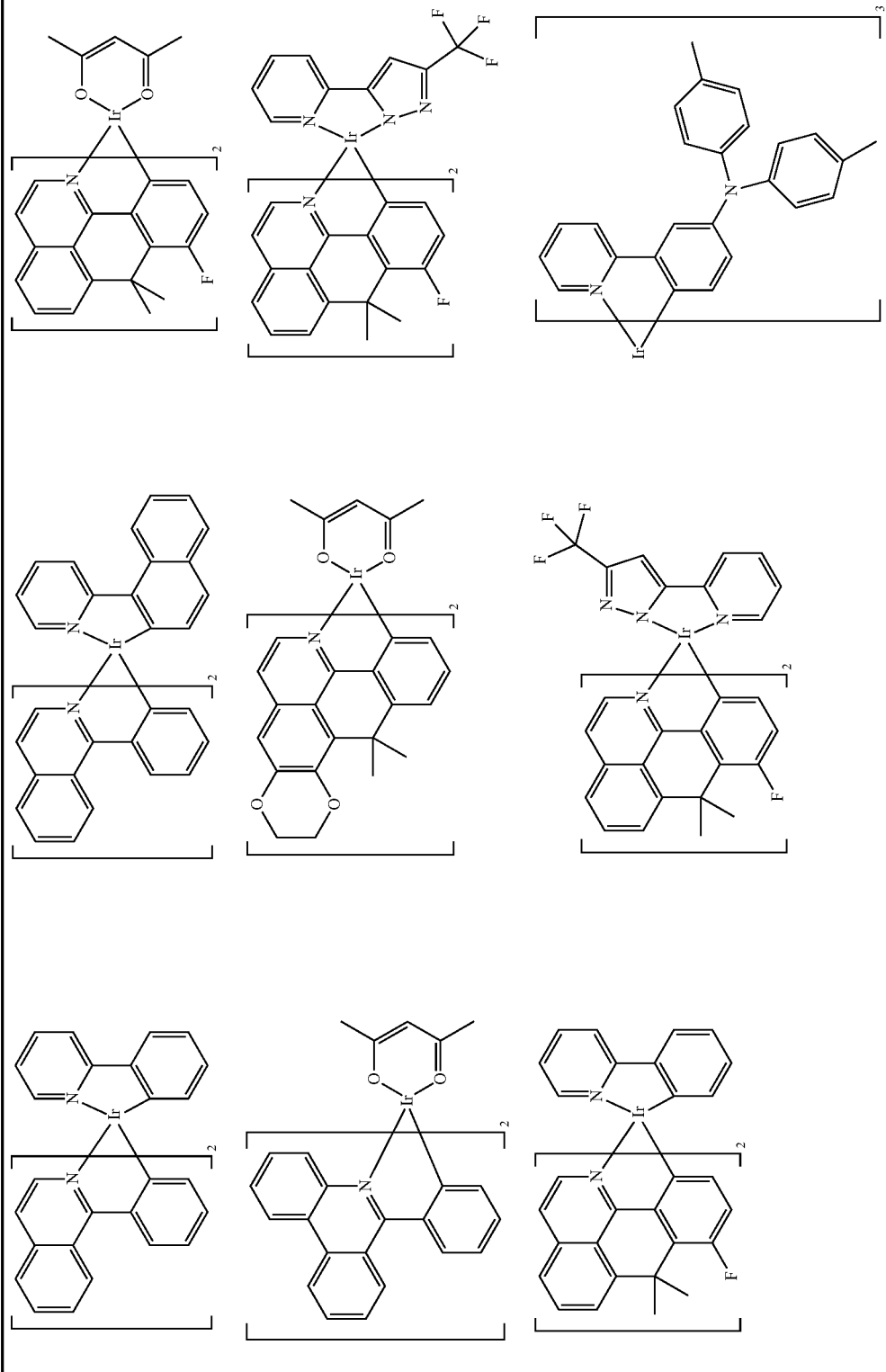

-continued
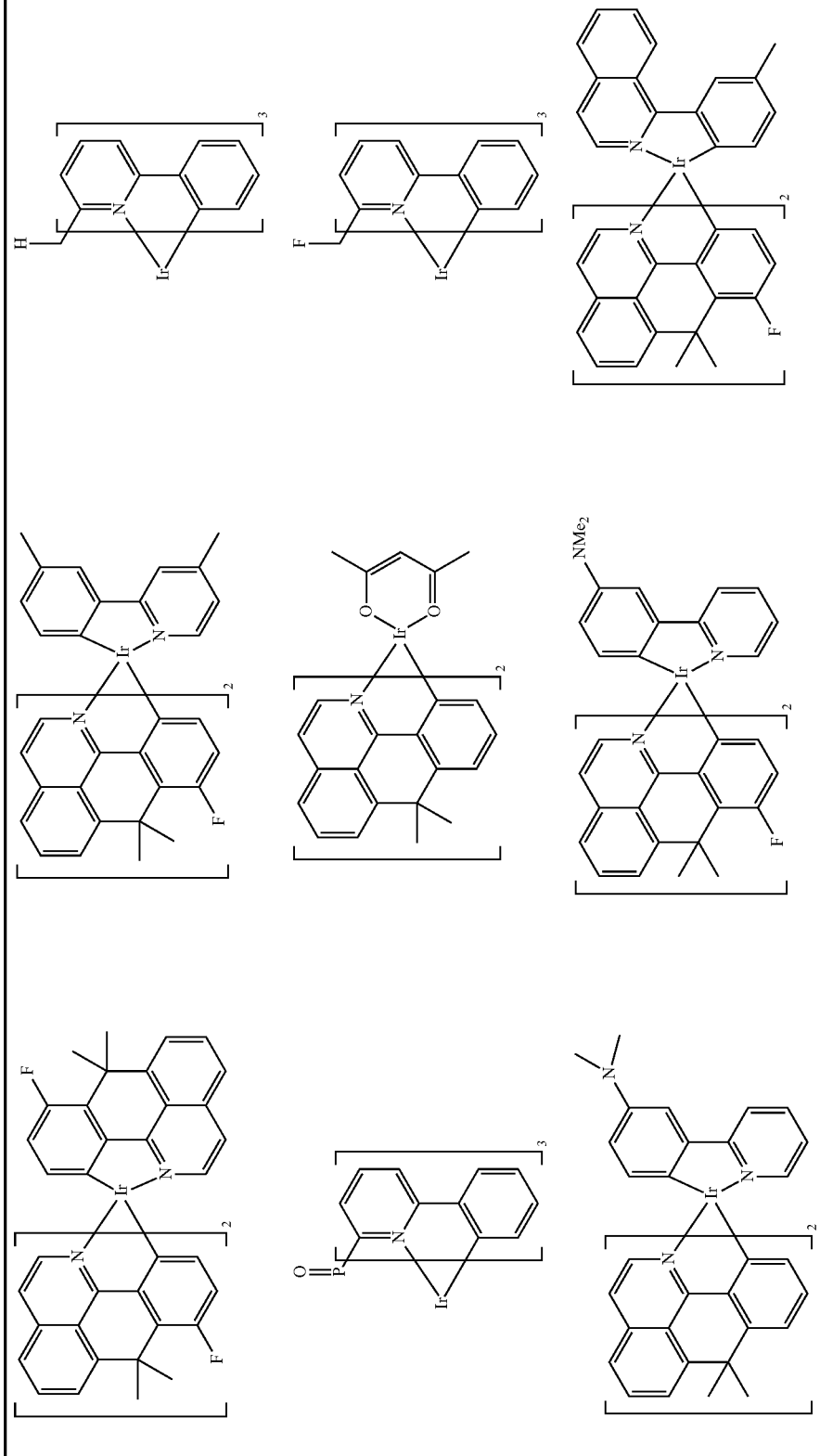

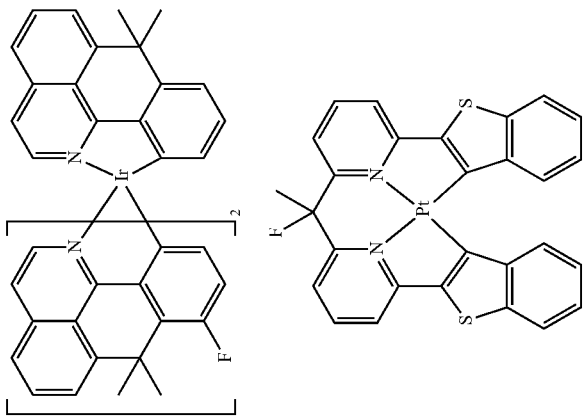
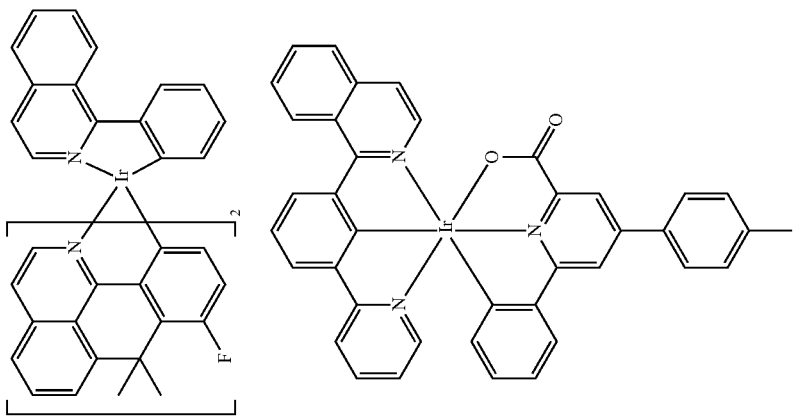
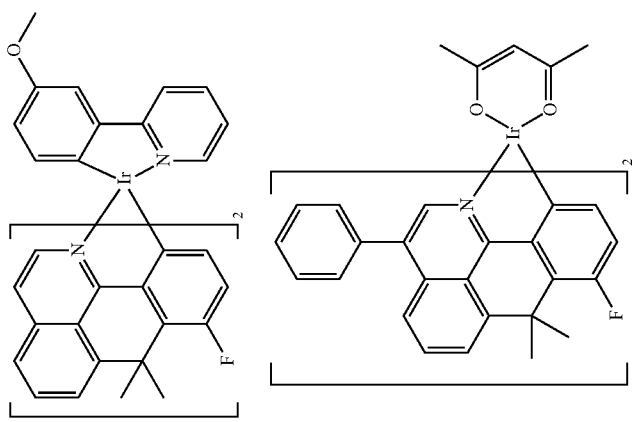

-continued
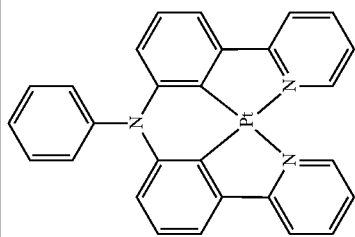
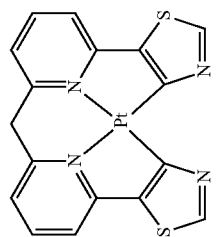
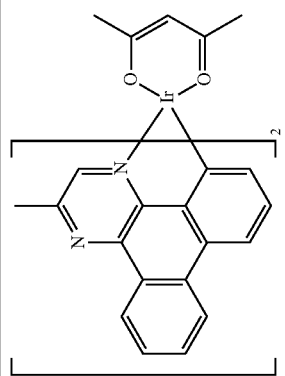
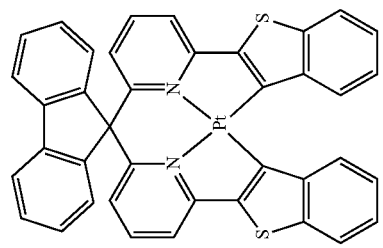
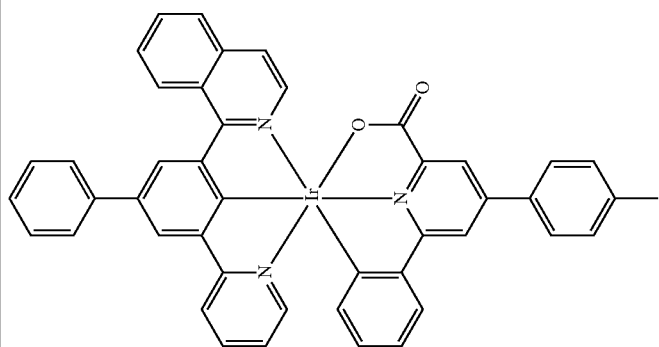
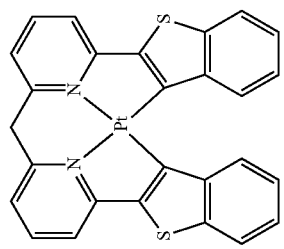

-continued
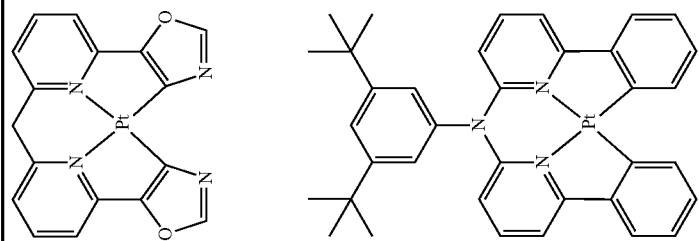
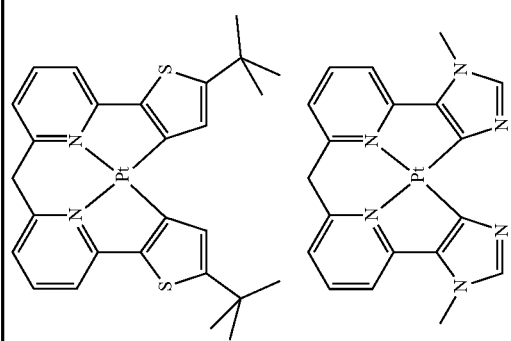
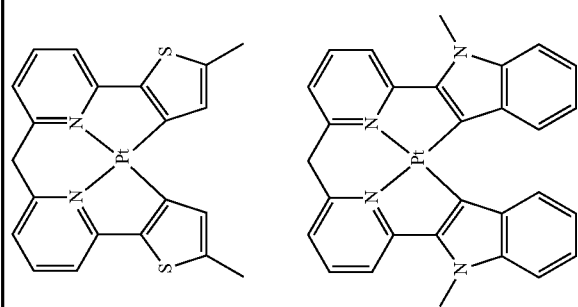

-continued
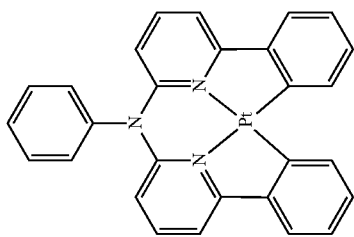 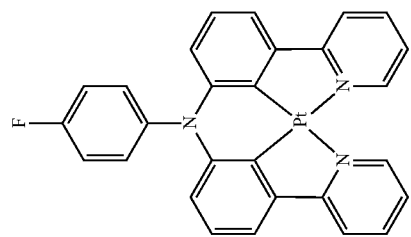
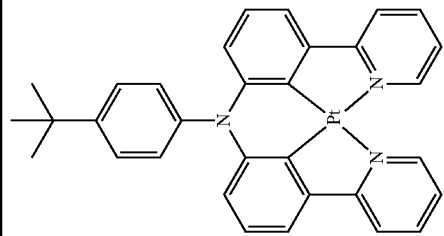 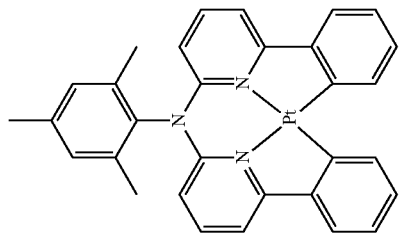
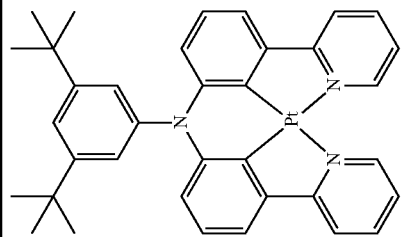 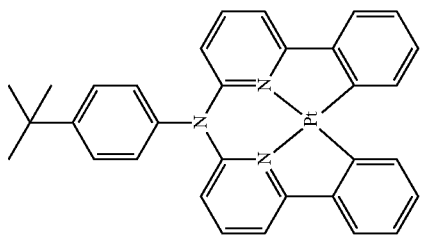

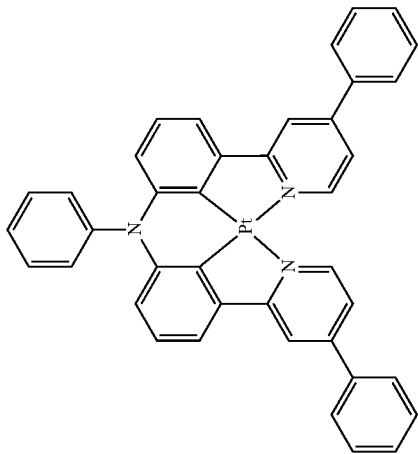
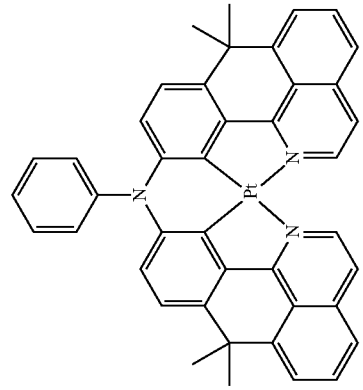
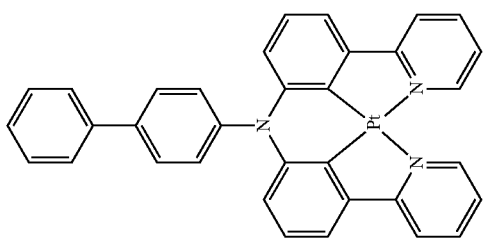
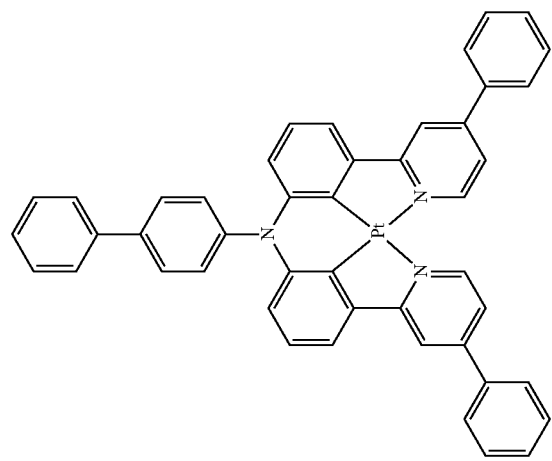
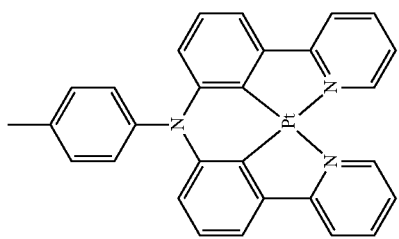
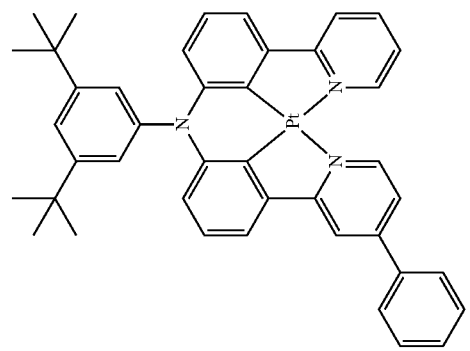

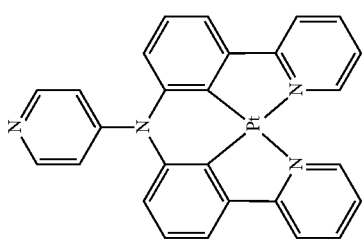
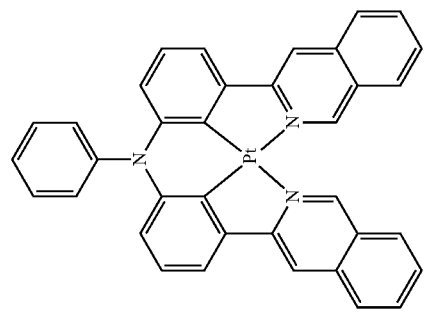
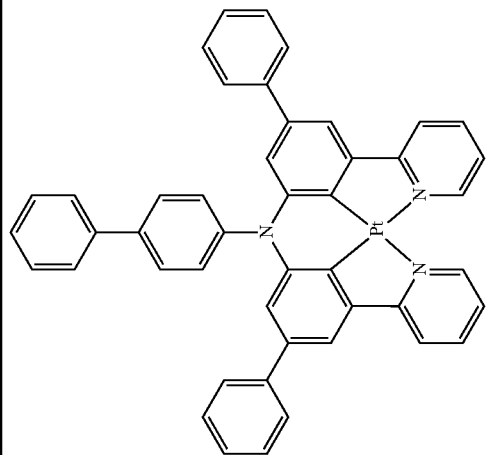
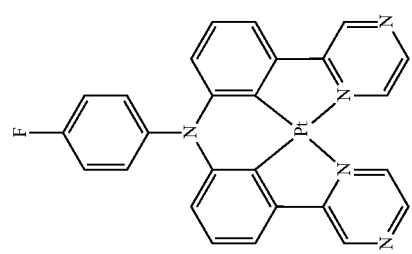
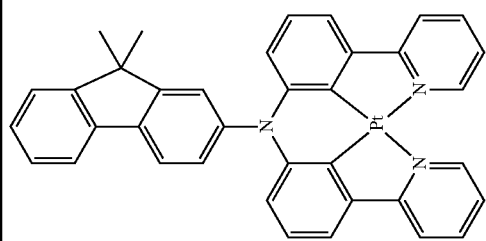
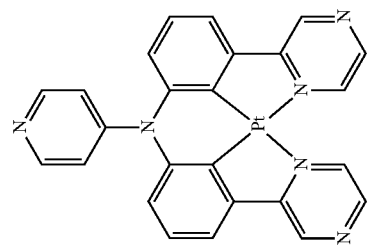

-continued
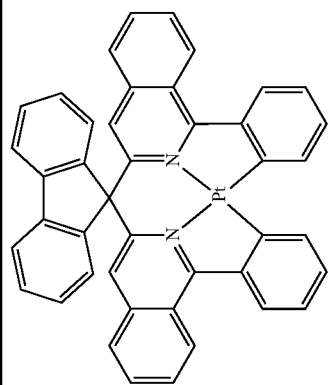 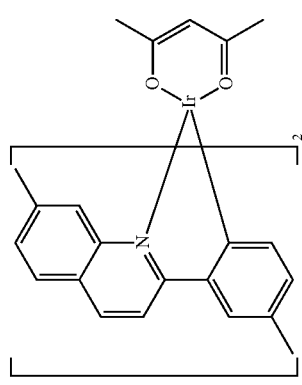 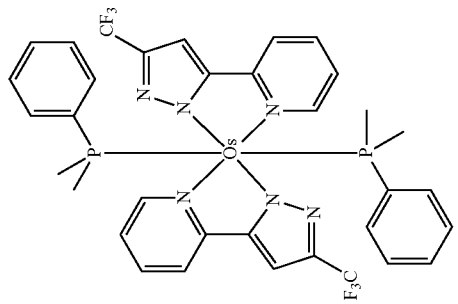
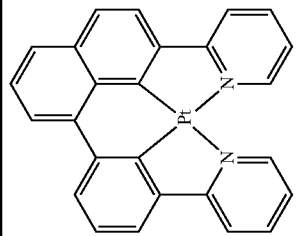 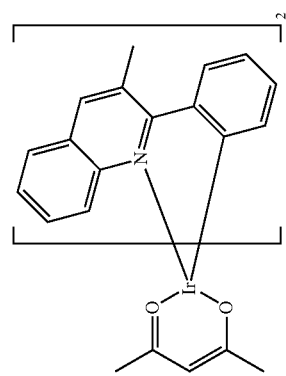 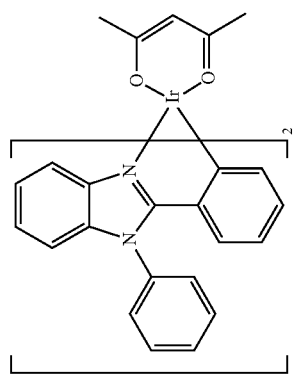
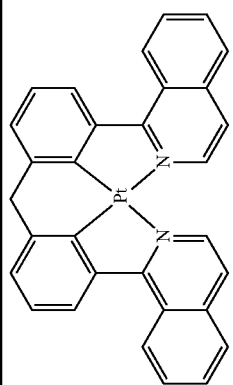 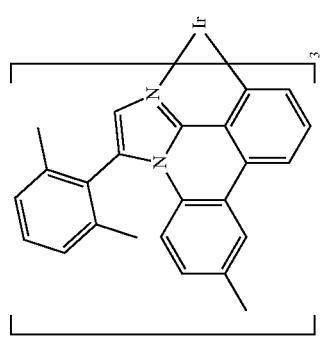 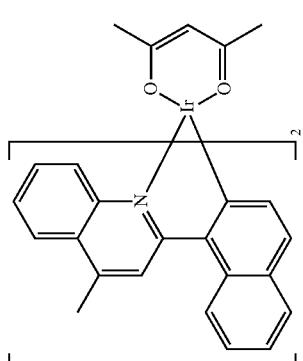

-continued
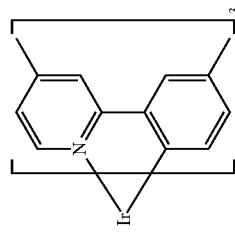 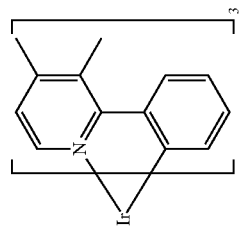 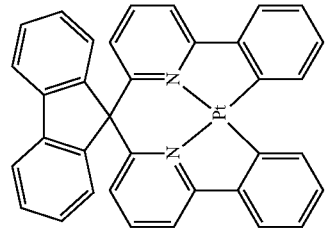
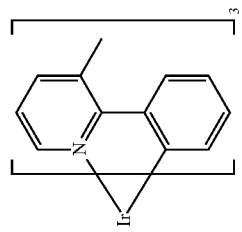 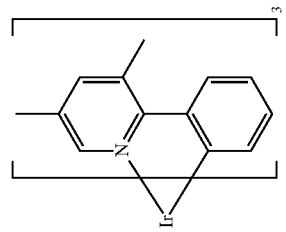 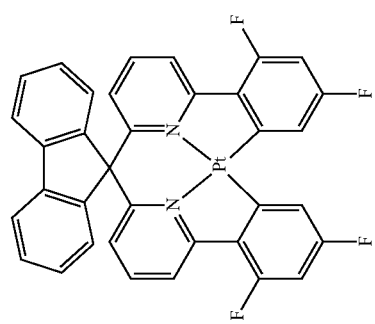
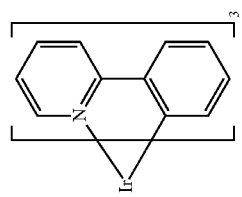 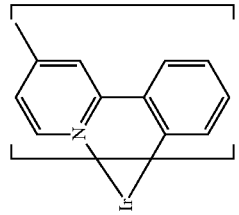 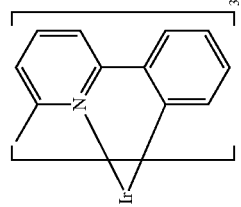

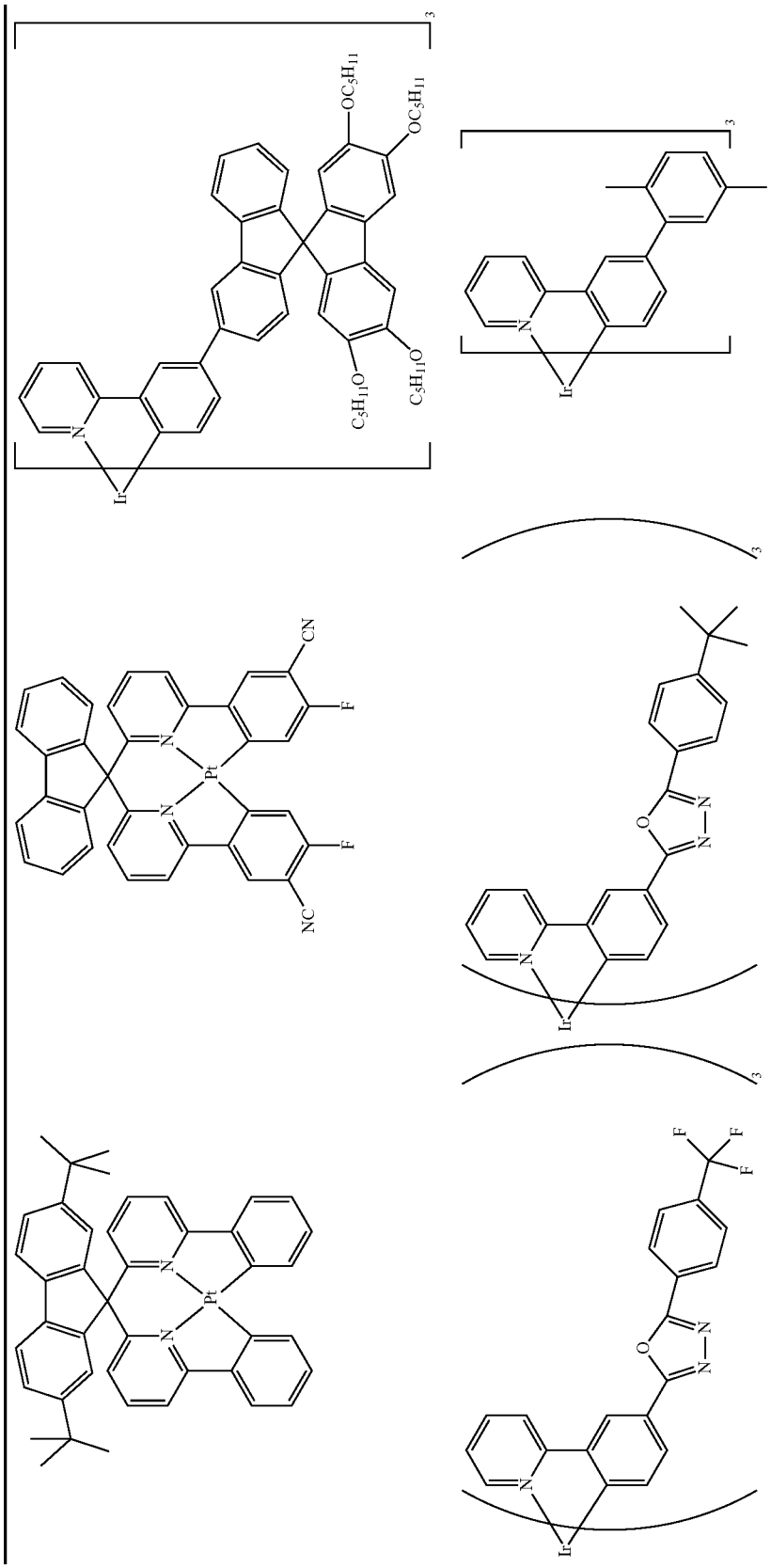

-continued
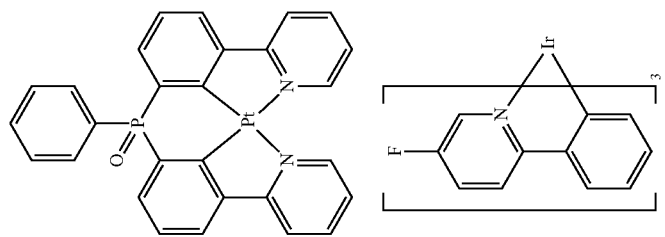
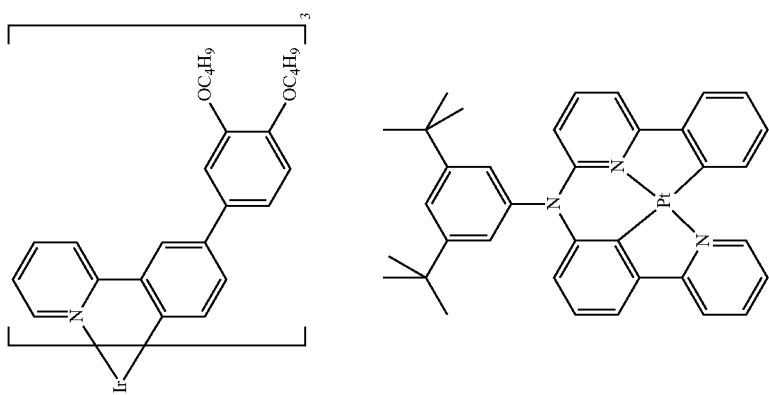
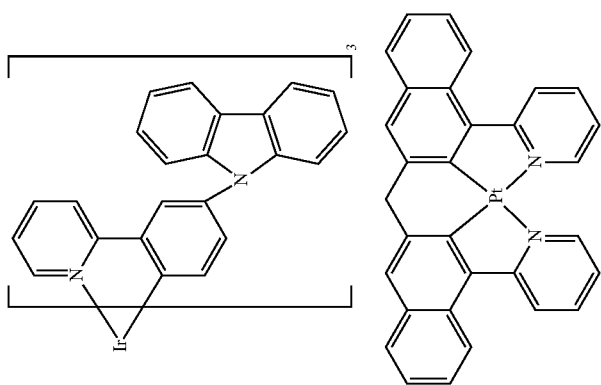

-continued
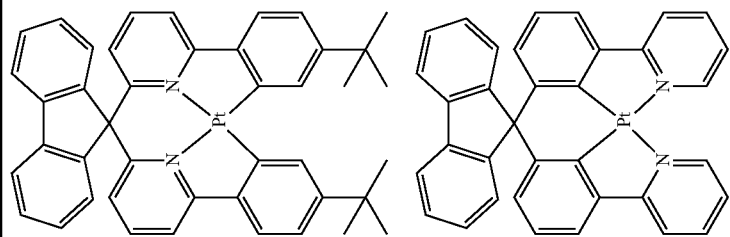
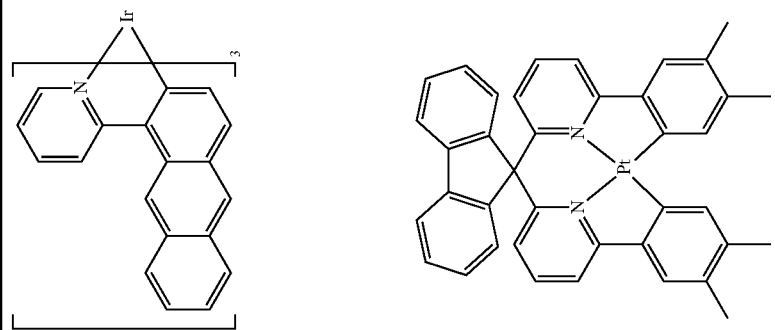
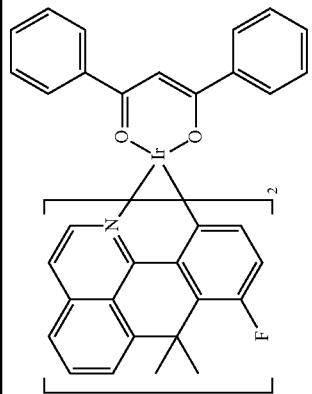
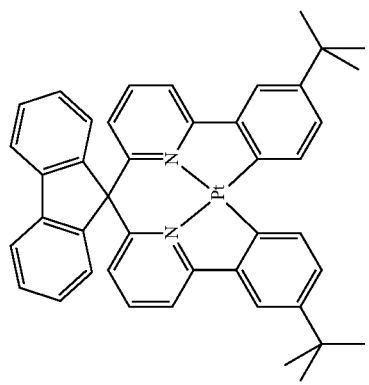

-continued
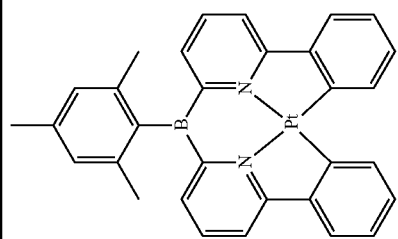
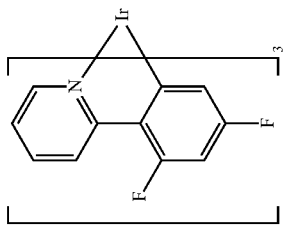
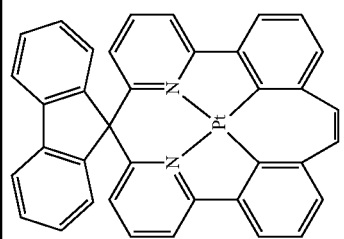
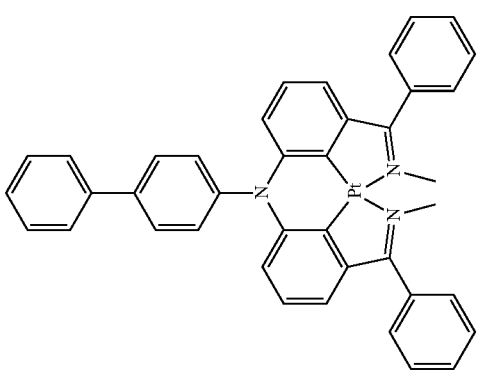
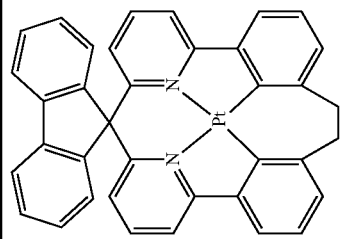
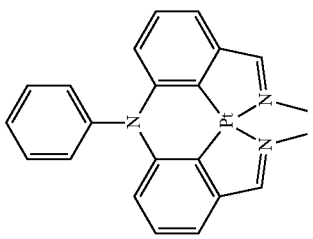

-continued
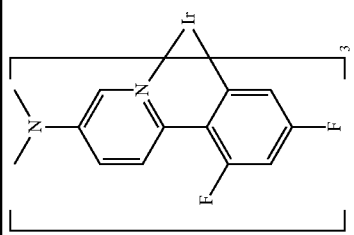 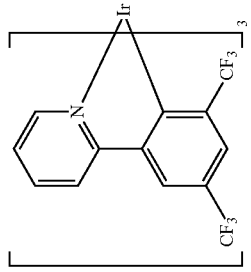 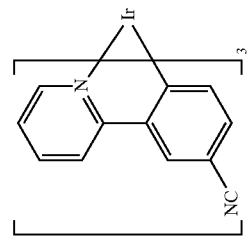
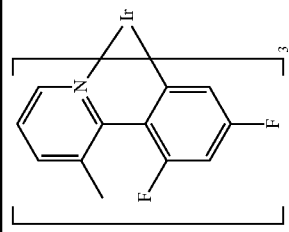 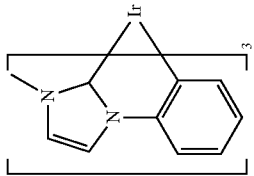 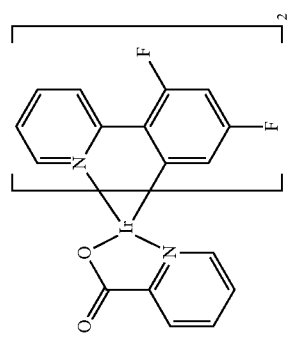
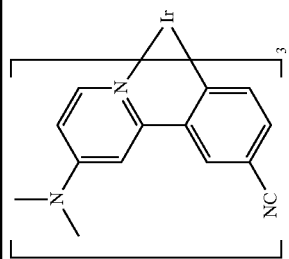 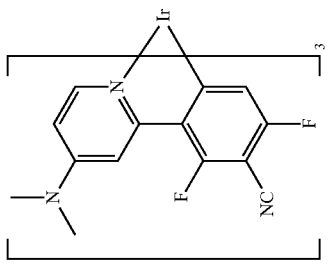 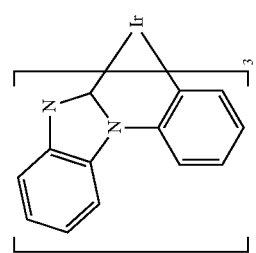

-continued
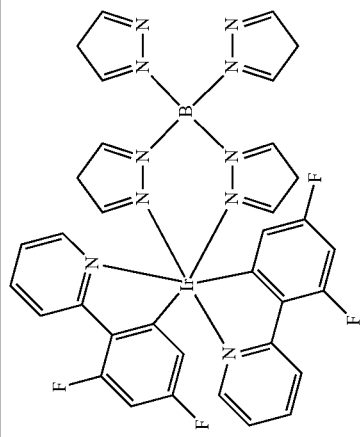 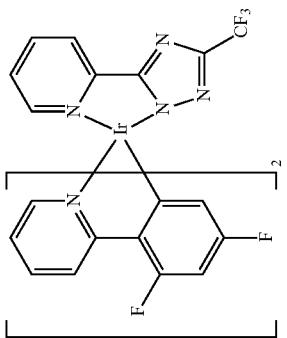 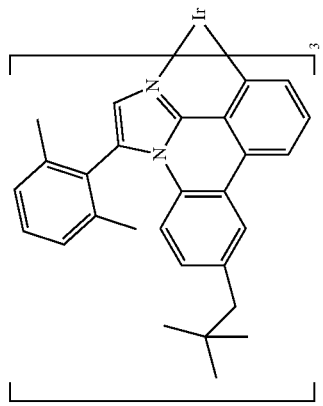
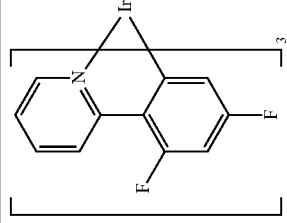 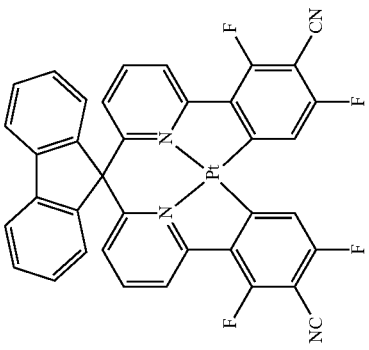 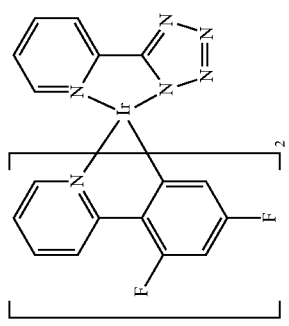
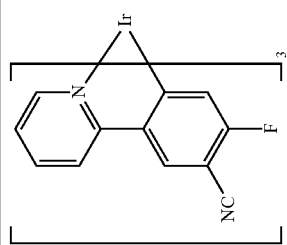 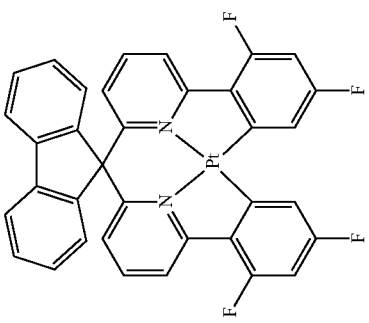 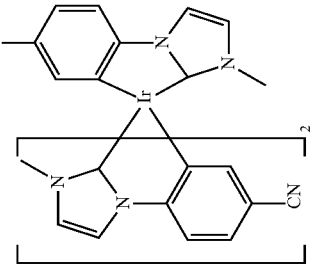

-continued
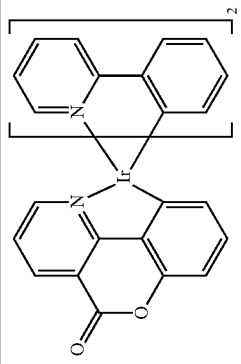 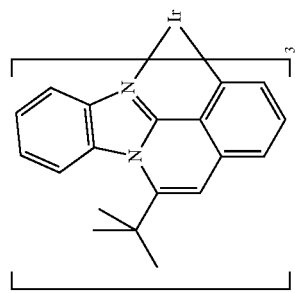 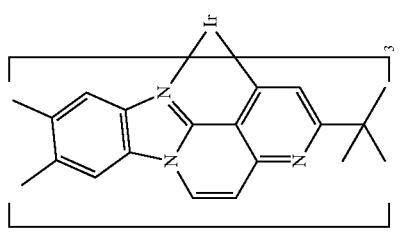
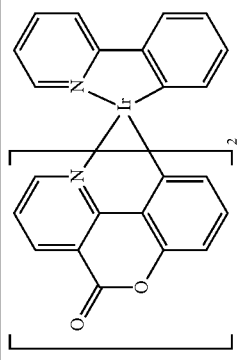 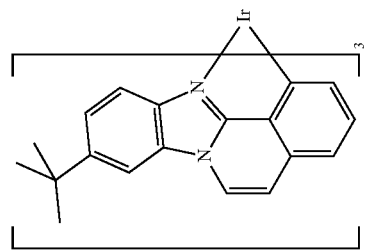 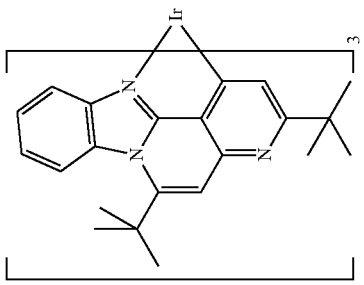
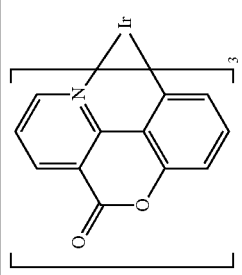 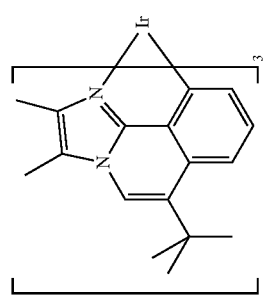 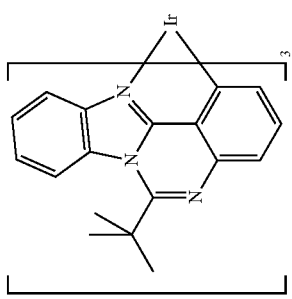

In a preferred embodiment of the invention, the compounds of the formula (I) are employed as hole-transport material. The compounds are then preferably employed in a hole-transport layer and/or in a hole-injection layer. A hole-injection layer in the sense of this invention is a layer which is directly adjacent to the anode. A hole-transport layer in the sense of this invention is a layer which is located between the hole-injection layer and the emission layer. The hole-transport layer may be directly adjacent to the emission layer. If the compounds of the formula (I) are used as hole-transport material or as hole-injection material, it may be preferred for them to be doped with electron-acceptor compounds, for example with $F_4$-TCNQ or with compounds as described in EP 1476881 or EP 1596445. In a further preferred embodiment of the invention, a compound of the formula (I) is used as hole-transport material in combination with a hexaazatriphenylene derivative, as described in US 2007/0092755. The hexaazatriphenylene derivative here is particularly preferably employed in a separate layer.

If the compound of the formula (I) is employed as hole-transport material in a hole-transport layer, the compound may be employed as pure material, i.e. in a proportion of 100%, in the hole-transport layer, or it may be employed in combination with one or more further compounds in the hole-transport layer.

In a further embodiment of the present invention, the compounds of the formula (I) are employed as matrix material in combination with one or more dopants, preferably phosphorescent dopants.

A dopant in a system comprising a matrix material and a dopant is taken to mean the component whose proportion in the mixture is the smaller. Correspondingly, a matrix material is taken to mean the component whose proportion in the mixture is the greater in a system comprising a matrix material and a dopant.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a further preferred embodiment of the invention, the compounds of the formula (I) are used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. However, the desired electron-transporting and hole-transporting properties of the mixed-matrix components may also be combined principally or completely in a single mixed-matrix components, where the further mixed-matrix component(s) fulfil other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More precise information on mixed-matrix systems is given, inter alia, in the application WO 2010/108579.

The mixed-matrix systems may comprise one or more dopants, preferably one or more phosphorescent dopants. In general, mixed-matrix systems are preferably employed in phosphorescent organic electroluminescent devices.

Particularly suitable matrix materials which can be used as matrix components of a mixed-matrix system in combination with the compounds according to the invention are selected from the preferred matrix materials for phosphorescent dopants indicated below or the preferred matrix materials for fluorescent dopants, depending on what type of dopant is employed in the mixed-matrix system.

Preferred phosphorescent dopants for use in mixed-matrix systems are the phosphorescent dopants shown in the above table.

The materials preferably employed in the relevant functions in the devices according to the invention are indicated below.

Preferred fluorescent dopants are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position.

Suitable matrix materials, preferably for fluorescent dopants, besides the compounds according to the invention, are materials from various classes of substance. Preferred matrix materials are selected from the classes of the oligoarylenes (for example 2,2',7,7-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Preferred matrix materials for phosphorescent dopants, besides the compounds according to the invention, are aromatic amines, in particular triarylamines, for example in accordance with US 2005/0069729, carbazole derivatives (for example CBP, N,N-biscarbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, diazaphosphole derivatives, for example in accordance with WO 2010/054730, and aluminium complexes, for example BAlq.

Suitable charge-transport materials, as can be used in the hole-injection or hole-transport layer or in the electron-transport layer of the organic electroluminescent device according to the invention, are, for example, the compounds disclosed in Y. Shirota et al., *Chem. Rev.* 2007, 107(4), 953-1010, or other materials as are employed in these layers in accordance with the prior art.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds of the formula (I) can be employed in displays, as light sources in lighting applications and as light sources in medical and/or cosmetic applications (for example light therapy).

The compounds according to the invention and the organic electroluminescent devices according to the invention are distinguished by the following surprising advantages over the prior art:

1. The compounds according to the invention are very highly suitable for use in a hole-transport layer or a hole-injection layer of an organic electroluminescent devices, in particular owing to their high hole mobility.
2. The compounds according to the invention have a relatively low sublimation temperature, high temperature stability and high oxidation stability in solution and are thus readily processible.
3. The compounds according to the invention, in particular employed as hole-transport or hole-injection material, result in high efficiencies and long lifetimes of the organic electroluminescent devices.

The invention is explained in greater detail by the following use examples, where the invention is not restricted to the scope of the examples.

WORKING EXAMPLES

A) Synthesis Examples

Synthesis of Precursor V1

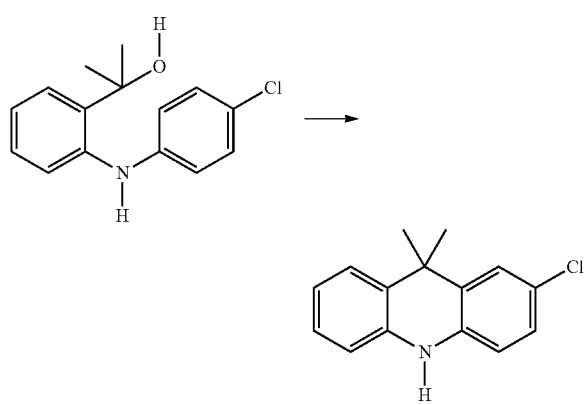

CAS Number: 918163-16-3

1st step: 2-chloro-9,9-dimethyl-9,10-dihydroacridine 30.3 g (116 mmol) of 2-[2-(4-chlorophenylamino)phenyl] propan-2-ol were dissolved in 700 ml of degassed toluene, and a suspension of 93 g of polyphosphoric acid and 61.7 g of methanesulfonic acid was added, and the mixture was stirred at room temperature for 1 h and heated at 50° C. for 1 h. The batch was cooled and added to ice and extracted three times with ethyl acetate. The combined org. phases were washed with sat. sodium chloride solution, dried over magnesium sulfate and evaporated. Filtration of the crude product through silica gel with heptane/ethyl acetate (20:1) gave 25.1 g (89%) of 2-chloro-9,9-dimethyl-9,10-dihydroacridine as pale-yellow crystals.

2nd step: 10-biphenyl-4-yl-2-chloro-9,9-dimethyl-9, 10-dihydroacridine

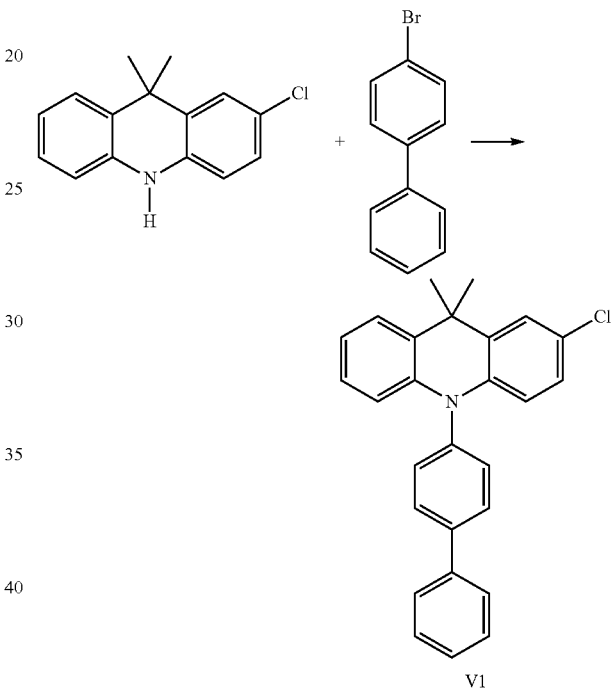

A degassed solution of 57.9 g (243.7 mmol) of 4-bromobiphenyl and 50 g (203.1 mmol) of 2-chloro-9,9-dimethyl-9,10-dihydroacridine in 1000 ml of toluene was saturated with $N_2$ for 1 h. Then, firstly 5.6 g (10.1 mmol) of DPPF, then 2.28 g (10.1 mmol) of palladium(II) acetate were added to the solution, and subsequently 52.3 g (528 mmol) of NaOtBu in the solid state were added. The reaction mixture was heated under reflux overnight. After cooling to room temperature, 500 ml of water were carefully added. The aqueous phase was washed with 3×50 ml of toluene, dried over $MgSO_4$, and the solvent was removed in vacuo. Filtration of the crude product through silica gel with heptane/ethyl acetate (20:1) gave 60 g (75%) of 10-biphenyl-4-yl-2-chloro-9,9-dimethyl-9,10-dihydroacridine as pale-yellow crystals.

Furthermore, the following compounds can be prepared in accordance with similar conditions as for the 2nd step of compound V1:

| Starting material 1 | Starting material 2 | Product | Yield |
|---|---|---|---|
| V2 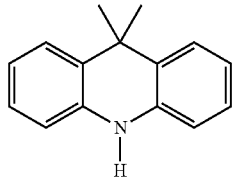 [SMILES: CC1(C)c2ccccc2Nc2ccccc21] 6267-02-3 | 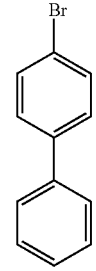 [SMILES: Brc1ccc(-c2ccccc2)cc1] | 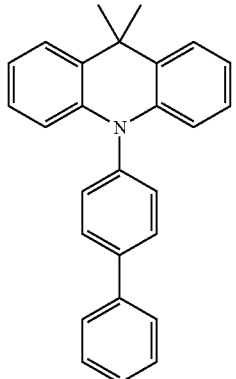 | 78% |
| V3 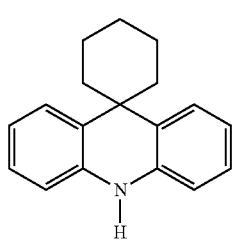 [SMILES: c1ccc2c(c1)Nc1ccccc1C21CCCCC1] 14458-75-4 | 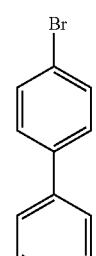 | 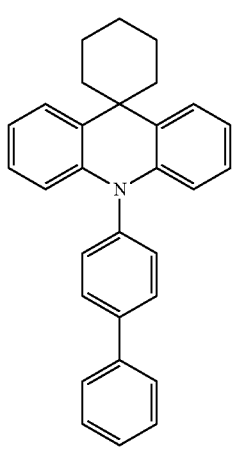 [SMILES: c1ccc(-c2ccc(N3c4ccccc4C4(CCCCC4)c4ccccc43)cc2)cc1] | 92% |
| V4 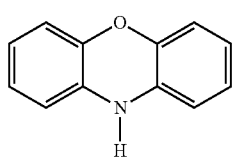 [SMILES: c1ccc2c(c1)Nc1ccccc1O2] | 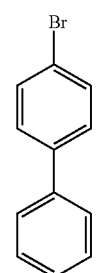 | 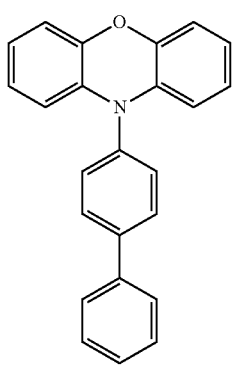 [SMILES: c1ccc(-c2ccc(N3c4ccccc4Oc4ccccc43)cc2)cc1] | 88% |
| V5 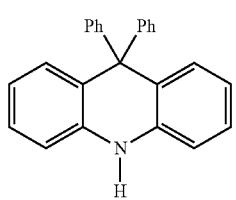 [SMILES: c1ccc(C2(c3ccccc3)c3ccccc3Nc3ccccc32)cc1] 20474-15-1 | 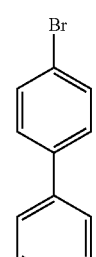 | 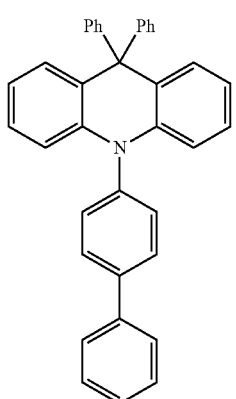 [SMILES: c1ccc(-c2ccc(N3c4ccccc4C(c4ccccc4)(c4ccccc4)c4ccccc43)cc2)cc1] | 85% |

-continued

| | Starting material 1 | Starting material 2 | Product | Yield |
|---|---|---|---|---|
| V6 | 25812-87-7 | | | 80% |
| V7 | 22493-89-6 | | | 88% |
| V8 | 34531-15-2 | | | 81% |
| V9 | 70626-31-2 | | | 75% |

Compounds V2a to V9a can be prepared from compounds V2-V9 by halogenation:

10-Biphenyl-4-yl-2,7-dibromo-9,9-dimethyl-9,10-dihydroacridine

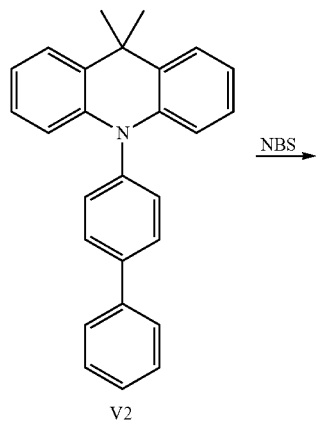

V2

NBS →

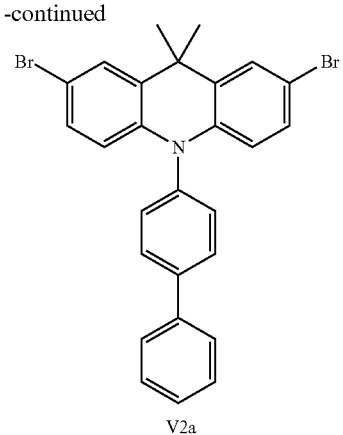

V2a

N-Bromosuccinimide (9.8 g, 55.3 mmol) was added in portions to a solution of the dihydroacridine (9.8 g, 55.3 mmol) in dichloromethane (140 ml) at 0° C. with exclusion of light, and the mixture was stirred at this temperature for 2 h. The reaction was terminated by addition of sodium sulfite solution and stirred at room temperature for a further 30 min. After phase separation, the organic phase was washed with water and the aqueous phase was extracted with dichloromethane. The combined organic phases were dried over sodium sulfate and evaporated in vacuo. The residue was dissolved in ethyl acetate and filtered through silica gel. The crude product was subsequently recrystallised from heptane. Yield: 14 g, 97% of theory, colourless solid.

| | Starting material 1 | Starting material 2 | Product | Yield |
|---|---|---|---|---|
| V3a | (V3 structure) | 1 eq. of NBS | (brominated V3 structure) | 92% |
| V4a | (V4 structure) | 1 eq. of NBS | (brominated V4 structure) | 97% |

-continued
| Starting material 1 | Starting material 2 | Product | Yield |
|---|---|---|---|
| V5a 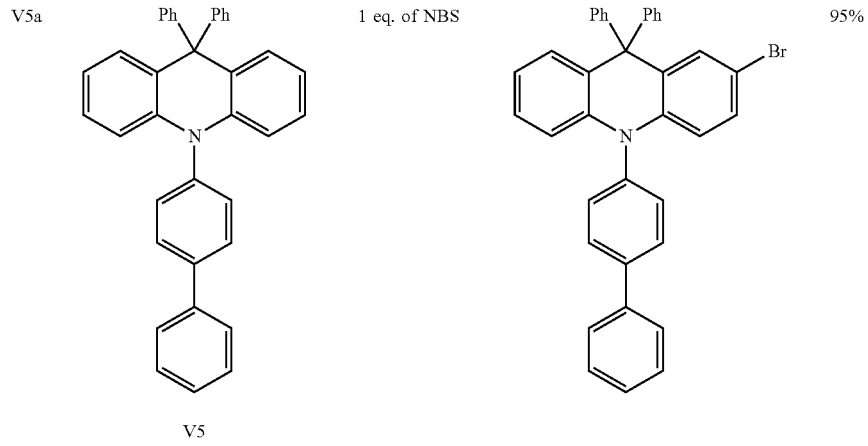 | 1 eq. of NBS | | 95% |
| V5b 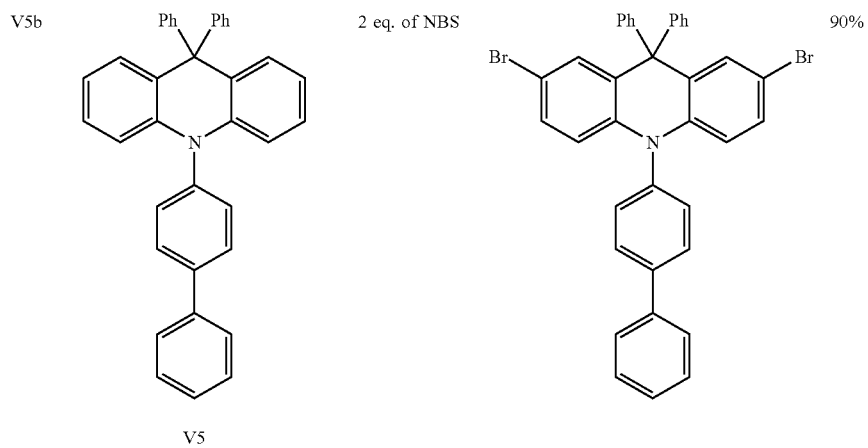 | 2 eq. of NBS | | 90% |
| V6a 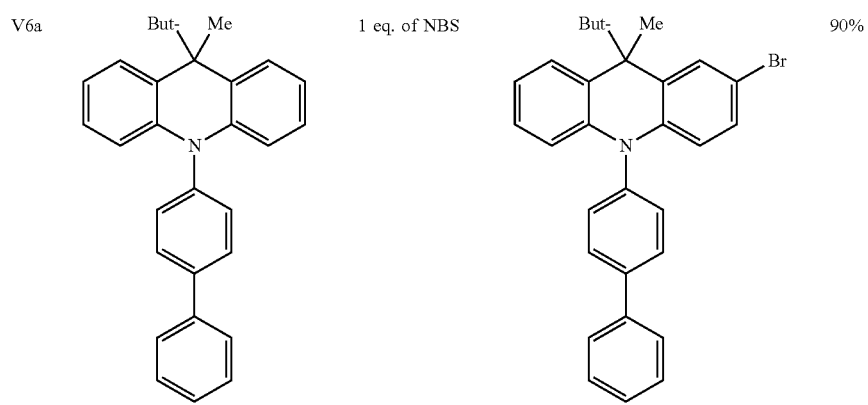 | 1 eq. of NBS | | 90% |

-continued

| | Starting material 1 | Starting material 2 | Product | Yield |
|---|---|---|---|---|
| V7a | V7 | 1 eq. of NBS | | 90% |
| V8a | V8 | 1 eq. of NBS | | 90% |

| Starting material 1 | Starting material 2 | Product | Yield |
|---|---|---|---|
| V9a | 1 eq. of NBS | V9 | 90% |

Compounds 1-14 according to the invention can be obtained from intermediates V1, V2a, V3a, V4a, V5a and V5b by Suzuki coupling.

10-Biphenyl-4-yl-9,9-dimethyl-2-phenyl-9,10-dihydroacridine

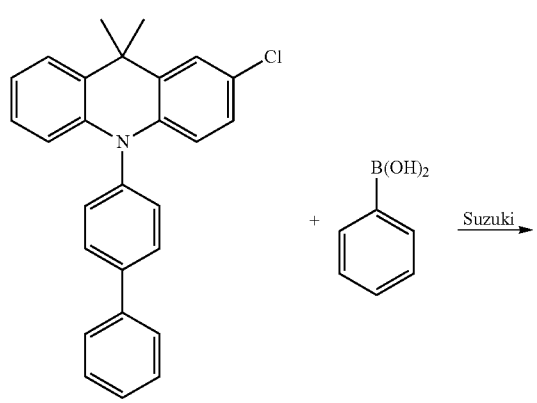

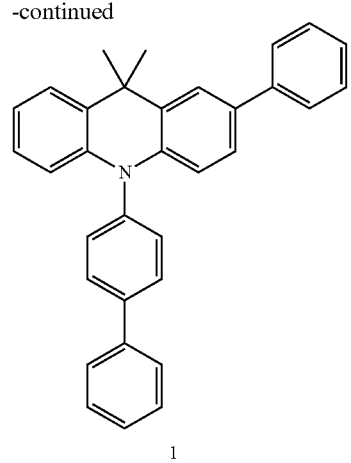

6.8 g (55.5 mmol) of benzeneboronic acid, 20 g (50.5 mmol) of 10-biphenyl-4-yl-2-chloro-9,9-dimethyl-9,10-dihydroacridine and 15.3 g (101 mmol) of CsF were suspended in 160 ml of dioxane. 1.8 g (2.5 mmol) of $PdCl_2(PCy_3)_2$ were added to this suspension, and the reaction mixture was heated under reflux for 16 h. After cooling, the organic phase was separated off, filtered through silica gel, washed three times with 200 ml of water and subsequently evaporated to dryness. The residue was recrystallised from toluene and finally sublimed in a high vacuum. The purity was 99.9%. The yield was 6.5 g, corresponding to 30% of theory.

Compounds 2 to 14 according to the invention can be obtained analogously:

| | Starting material 1 | Starting material 2 | Product | Yield |
|---|---|---|---|---|
| 2 | 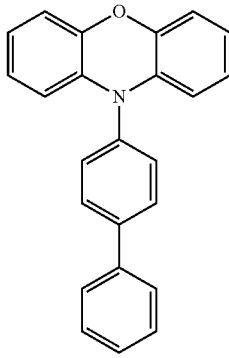<br>V4a | 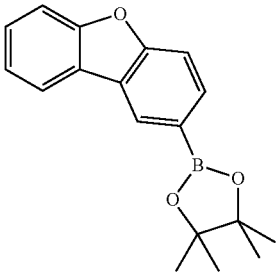 [SMILES: CC1(C)OB(c2ccc3oc4ccccc4c3c2)OC1(C)C]<br>947770-80-1 | 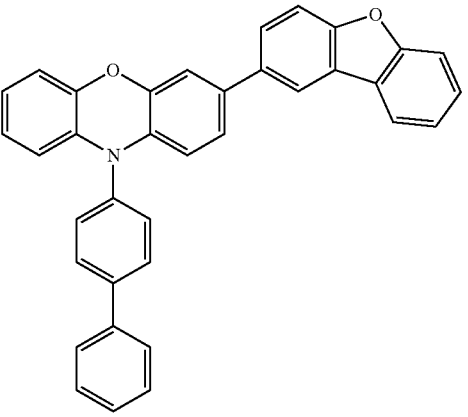 [SMILES: c1ccc(-c2ccc(N3c4ccccc4Oc4cc(-c5ccc6oc7ccccc7c6c5)ccc43)cc2)cc1] | 72% |
| 3 | 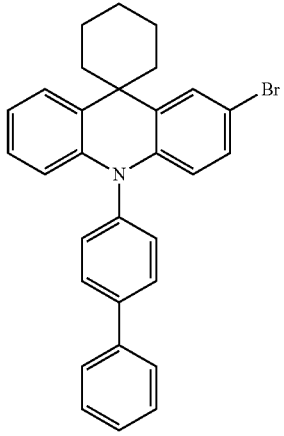 [SMILES: Brc1ccc2c(c1)C1(CCCCC1)c1ccccc1N2c1ccc(-c2ccccc2)cc1]<br>V3a | 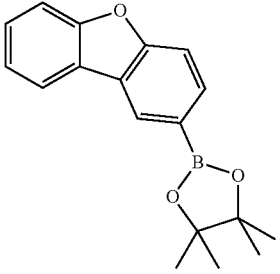 [SMILES: CC1(C)OB(c2ccc3oc4ccccc4c3c2)OC1(C)C]<br>947770-80-1 | 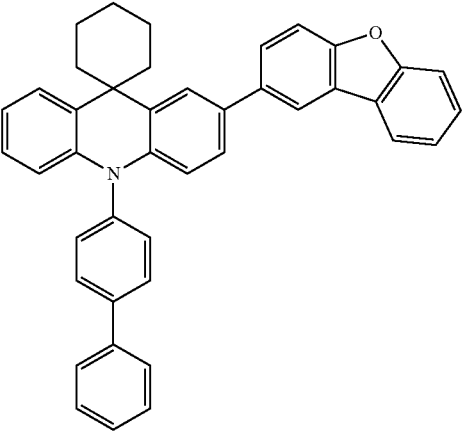 [SMILES: c1ccc(-c2ccc(N3c4ccccc4C4(CCCCC4)c4cc(-c5ccc6oc7ccccc7c6c5)ccc43)cc2)cc1] | 65% |
| 4 | 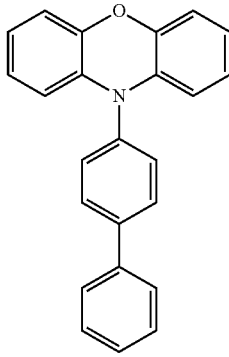<br>V4a | 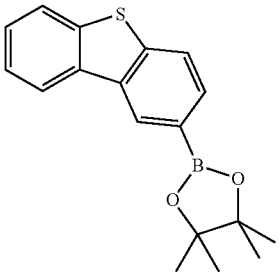 [SMILES: CC1(C)OB(c2ccc3sc4ccccc4c3c2)OC1(C)C]<br>890042-21-4 | 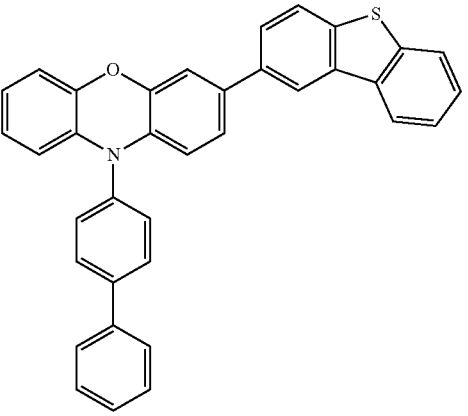 [SMILES: c1ccc(-c2ccc(N3c4ccccc4Oc4cc(-c5ccc6sc7ccccc7c6c5)ccc43)cc2)cc1] | 54% |

-continued

| | Starting material 1 | Starting material 2 | Product | Yield |
|---|---|---|---|---|
| 5 | V3a | 890042-21-4 | | 60% |
| 6 | V2a | 2 eq. of benzene-boronic acid | | 50% |
| 7 | V1 | 947770-80-1 | | 52% |

-continued

| Starting material 1 | Starting material 2 | Product | Yield |
|---|---|---|---|
| 8 V1 | 890042-21-4 | | 47% |
| 9 V5a | 1 eq. of benzene-boronic acid | | 55% |
| 10 V5b | 2.eq. of benzene-boronic acid | | 60% |

-continued

| | Starting material 1 | Starting material 2 | Product | Yield |
|---|---|---|---|---|
| 11 | V1 | 569343-09-5 | | 63% |
| 12 | V1 | 461128-39-8 | | 57% |
| 13 | V1 | 1259280-37-9 | | 67% |

-continued
| Starting material 1 | Starting material 2 | Product | Yield |
|---|---|---|---|
| 14 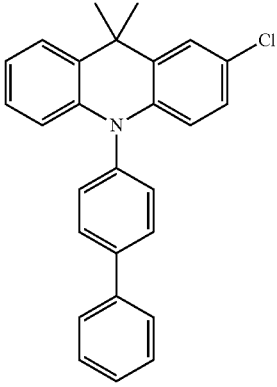 [SMILES: CC1(C)c2ccccc2N(c2ccc(-c3ccccc3)cc2)c2ccc(Cl)cc21] V1 | 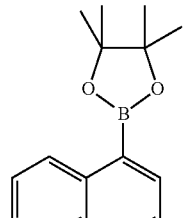 68716-52-9 | 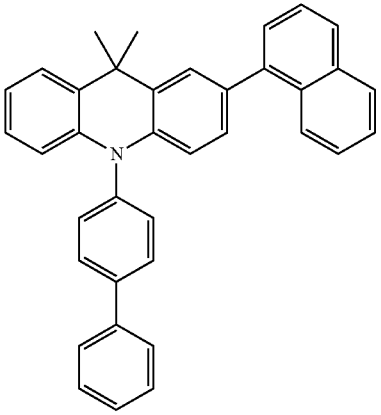 | 70% |
Furthermore, compounds 15 to 18 were obtained from precursors V6a to V9a by Suzuki coupling to phenylboronic acid under analogous conditions:
15
V6a
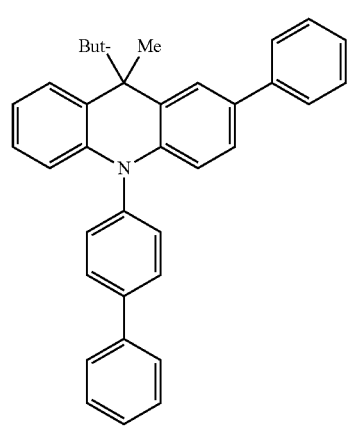 [SMILES: c1ccc(-c2ccc(N3c4ccccc4C(c4ccccc4)(c4ccccc4)c4cc(-c5ccccc5)ccc43)cc2)cc1]
16
V7a
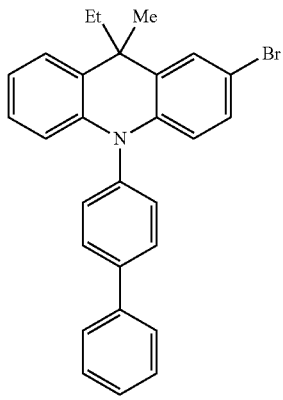
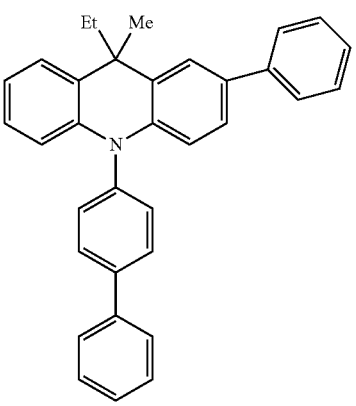

17

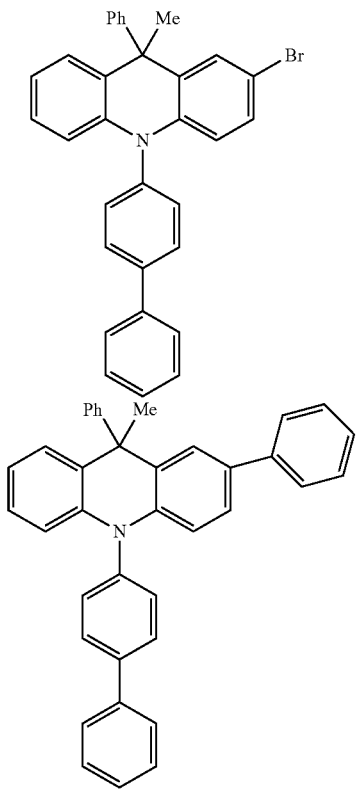
V8a

18

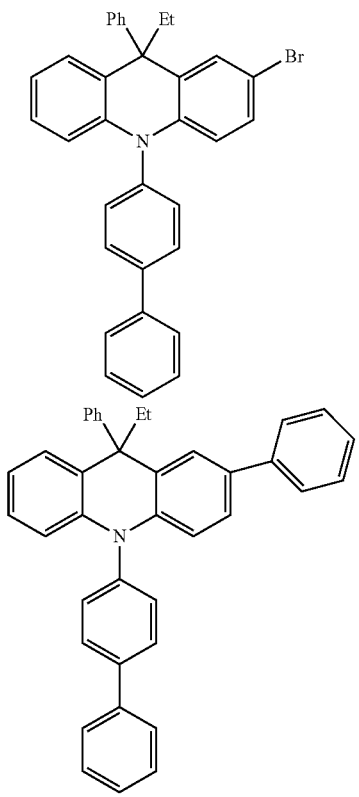
V9a

B) Device Examples

Production of OLEDs

OLEDs according to the invention and OLEDs in accordance with the prior art are produced by a general process in accordance with WO 04/058911, which is adapted to the circumstances described here (layer-thickness variation, materials).

The structure and data for various OLEDs are presented in Examples V1 to V8 and E1 to E6 below (see Tables 1 to 5). Glass plates coated with structured ITO (indium tin oxide) in a thickness of 150 nm are coated with 20 nm of PEDOT (poly(3,4-ethylenedioxy-2,5-thiophene), applied by spin coating from water; purchased from H. C. Starck, Goslar, Germany) for improved processing. These coated glass plates form the substrates to which the OLEDs are applied. The OLEDs basically have the following layer structure: substrate/optional hole-injection layer (HIL)/hole-transport layers (HTL)/optional interlayer (IL)/electron-blocking layer (EBL)/emission layer (EML)/electron-transport layer (ETL)/optional electron-injection layer (EIL) and finally a cathode. The cathode is formed by an aluminium layer with a thickness of 100 nm. The precise structure of the OLEDs is shown in Tables 1 and 3. The materials required for the production of the OLEDs are shown in Table 5.

All materials are applied by thermal vapour deposition in a vacuum chamber. The emission layer here always consists of at least one matrix material (host material) and an emitting dopant (emitter), to which the matrix material or matrix materials is admixed in a certain proportion by volume by co-evaporation. An expression such as H1:SEB1 (95%:5%) here means that material H1 is present in the layer in a proportion by volume of 95% and SEB1 is present in the layer in a proportion of 5%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The expression U @ 1000 cd/m$^2$ in Table 2 and 4 denotes the voltage required for a luminous density of 1000 cd/m$^2$. Finally, EQE @ 1000 cd/m$^2$ denotes the external quantum efficiency at an operating luminous density of 1000 cd/m$^2$. LT80 @ 6000 cd/m2 is the lifetime by which the OLED at a luminance of 6000 cd/m$^2$ has dropped to 80% of the initial intensity, i.e. to 4800 cd/m$^2$.

The measured data of the various OLEDs are summarised in Tables 2 and 4.

Use of the Compounds According to the Invention in Fluorescent and Phosphorescent OLEDs The compounds according to the invention are suitable, in particular, as HTM (hole-transport material) or EBM (electron-blocking material) in OLEDs. They are suitable for use in a single layer, but also as a mixed component as HTM, EBM or as constituent of the emitting layer. Compared with comparative devices in accordance with the prior art (V1 to V8), all samples comprising the compounds according to the invention exhibit higher efficiencies together with the same or improved lifetimes (E1 to E6).

Compared with reference material HTMV1 (V2 and V6), the compounds according to the invention exhibit better efficiencies and better lifetimes. Thus, the lifetime of V2 is virtually doubled compared with E1 to E3 in a blue-emitting device, and the lifetime is also virtually doubled in the green-emitting device (V6 compared with E4 to E6).

Compared with reference material HTMV2 (V3 and V7), better or equally good (HTM2) lifetimes are obtained for the compounds according to the invention in blue- or green-emitting devices at the same time as a significant improvement in the efficiency.

Compared with reference material HTMV3 (V4 and V8), significantly better efficiencies and lifetimes are obtained for the compounds according to the invention.

TABLE 1

Structure of the OLEDs

| Ex. | IL Thickness/nm | HTL Thickness/nm | IL Thickness/nm | HTL2 Thickness/nm | EBL Thickness/nm | EML Thickness/nm | ETL Thickness/nm |
|---|---|---|---|---|---|---|---|
| V1 | HIL1 5 nm | HIL2 140 nm | HIL1 5 nm | | NPB 20 nm | H1(95%):SEB1(5%) 20 nm | ETM1(50%):LiQ(50%) 30 nm |
| V2 | HIL1 5 nm | HIL2 140 nm | HIL1 5 nm | | HTMV1 20 nm | H1(95%):SEB1(5%) 20 nm | ETM1(50%):LiQ(50%) 30 nm |
| V3 | HIL1 5 nm | HIL2 140 nm | HIL1 5 nm | | HTMV2 20 nm | H1(95%):SEB1(5%) 20 nm | ETM1(50%):LiQ(50%) 30 nm |
| V4 | HIL1 5 nm | HIL2 130 nm | HIL1 5 nm | NPB 10 nm | HTMV3 20 nm | H1(95%):SEB1(5%) 20 nm | ETM1(50%):LiQ(50%) 30 nm |
| E1 | HIL1 5 nm | HIL2 130 nm | HIL1 5 nm | NPB 10 nm | HTM1 20 nm | H1(95%):SEB1(5%) 20 nm | ETM1(50%):LiQ(50%) 30 nm |
| E2 | HIL1 5 nm | HIL2 130 nm | HIL1 5 nm | NPB 10 nm | HTM2 20 nm | H1(95%):SEB1(5%) 20 nm | ETM1(50%):LiQ(50%) 30 nm |
| E3 | HIL1 5 nm | HIL2 130 nm | HIL1 5 nm | NPB 10 nm | HTM3 20 nm | H1(95%):SEB1(5%) 20 nm | ETM1(50%):LiQ(50%) 30 nm |

TABLE 2

Data of the OLEDs

| Ex. | U @ 1000 cd/m2 V | EQE @ 1000 cd/m2 % | LT80 @ 6000 cd/m$^2$ [h] | CIE x | CIE y |
|---|---|---|---|---|---|
| V1 | 4.7 | 4.8 | 70 | 0.14 | 0.17 |
| V2 | 4.2 | 5.4 | 55 | 0.14 | 0.17 |
| V3 | 4.4 | 6.0 | 90 | 0.14 | 0.16 |
| V4 | 4.5 | 5.7 | 60 | 0.14 | 0.16 |
| E1 | 4.2 | 7.6 | 100 | 0.14 | 0.16 |
| E2 | 4.3 | 8.4 | 90 | 0.14 | 0.16 |
| E3 | 4.3 | 7.3 | 135 | 0.14 | 0.16 |

TABLE 3

Structure of the OLEDs

| Ex. | HTL Thickness/nm | IL Thickness/nm | HTL2 Thickness/nm | EBL Thickness/nm | EML Thickness/nm | ETL Thickness/nm |
|---|---|---|---|---|---|---|
| V5 | HIL2 70 nm | HIL1 5 nm | | NPB 90 nm | H2(88%):Irpy(12%) 30 nm | ETM1(50%):LiQ(50%) 40 nm |
| V6 | HIL2 70 nm | HIL1 5 nm | | HTMV1 90 nm | H2(88%):Irpy(12%) 30 nm | ETM1(50%):LiQ(50%) 40 nm |
| V7 | HIL2 70 nm | HIL1 5 nm | | HTMV2 90 nm | H2(88%):Irpy(12%) 30 nm | ETM1(50%):LiQ(50%) 40 nm |
| V8 | HIL2 70 nm | HIL1 5 nm | NPB 10 nm | HTMV3 80 nm | H2(88%):Irpy(12%) 30 nm | ETM1(50%):LiQ(50%) 40 nm |
| E4 | HIL2 70 nm | HIL1 5 nm | NPB 10 nm | HTM1 80 nm | H2(88%):Irpy(12%) 30 nm | ETM1(50%):LiQ(50%) 40 nm |
| E5 | HIL2 70 nm | HIL1 5 nm | NPB 10 nm | HTM2 80 nm | H2(88%):Irpy(12%) 30 nm | ETM1(50%):LiQ(50%) 40 nm |
| E6 | HIL2 70 nm | HIL1 5 nm | NPB 10 nm | HTM3 80 nm | H2(88%):Irpy(12%) 30 nm | ETM1(50%):LiQ(50%) 40 nm |

TABLE 4

| | Data of the OLEDs | | | | |
|---|---|---|---|---|---|
| | U @ 1000 cd/m2 | Efficiency @ 1000 cd/m2 | LT80 @ 8000 cd/m$^2$ | CIE | |
| Ex. | V | % | [h] | x | y |
| V5 | 3.6 | 14.4 | 85 | 0.32 | 0.63 |
| V6 | 3.1 | 13.1 | 60 | 0.33 | 0.64 |
| V7 | 3.2 | 17.1 | 110 | 0.33 | 0.63 |
| V8 | 3.1 | 15.1 | 85 | 0.32 | 0.63 |
| E4 | 3.2 | 17.6 | 140 | 0.33 | 0.64 |
| E5 | 3.3 | 18.1 | 100 | 0.33 | 0.63 |
| E6 | 3.1 | 17.8 | 140 | 0.33 | 0.64 |

TABLE 5
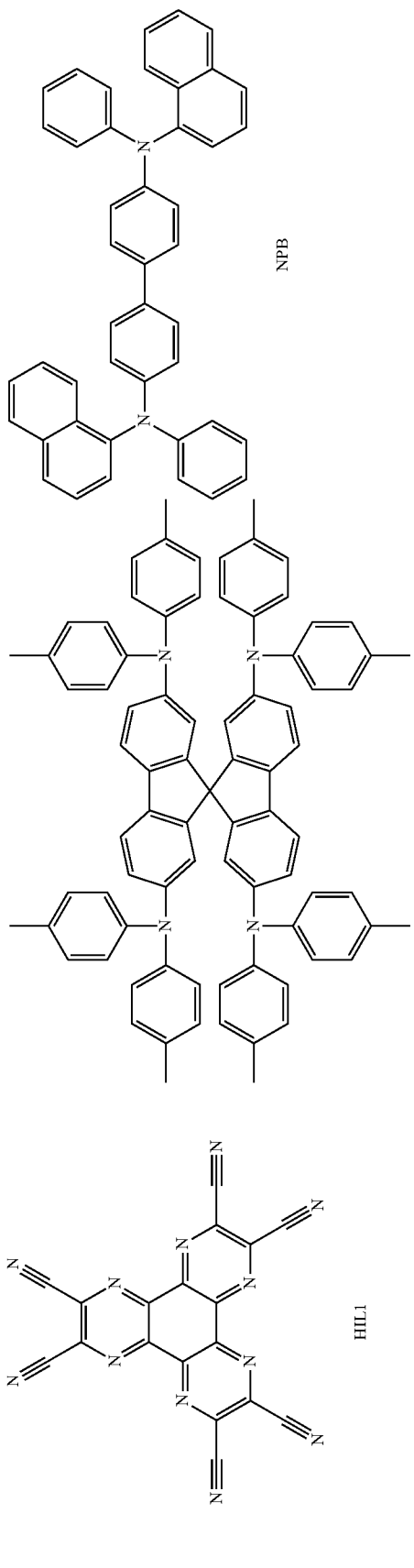
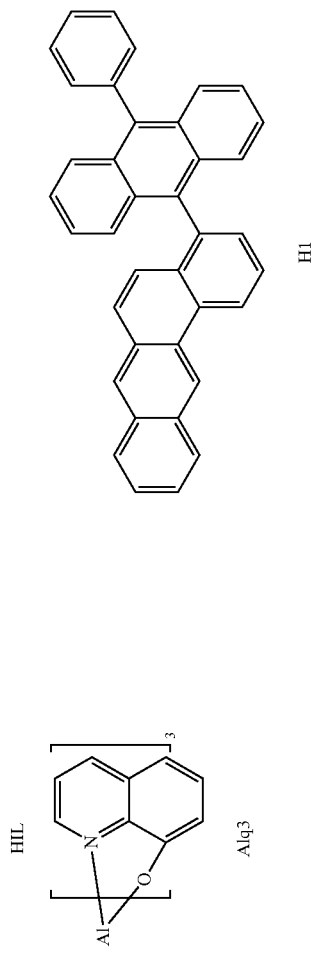
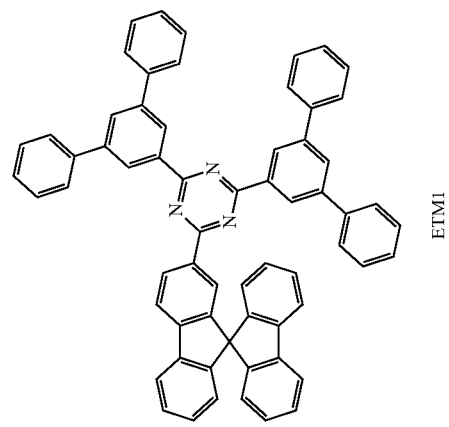

TABLE 5-continued
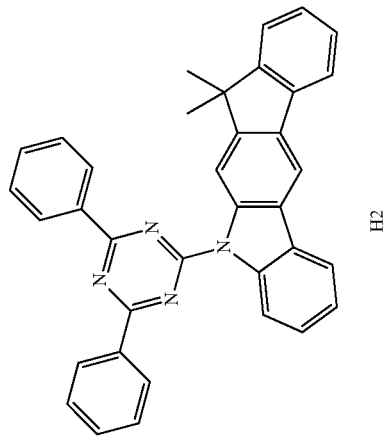
H2
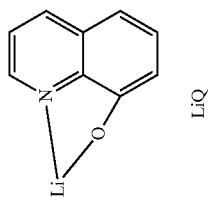
LiQ
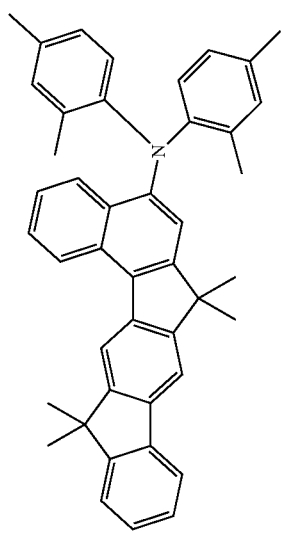
SEB1
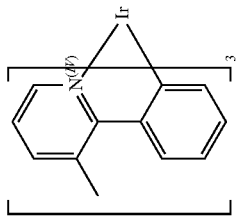
Irpy TABLE 5-continued
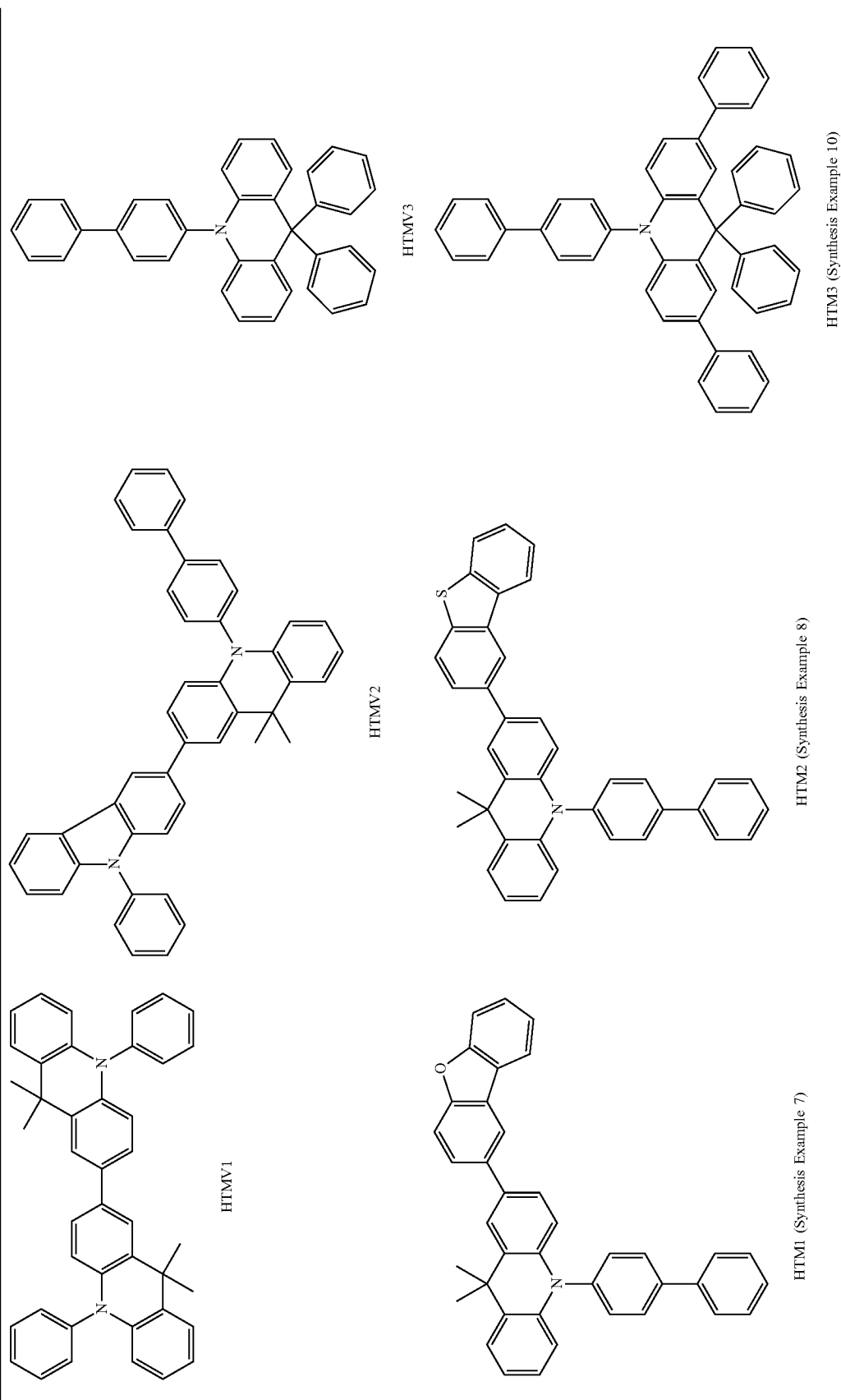

The invention claimed is:

1. A compound of a formula (1-A-1) or formula (1-A-2)

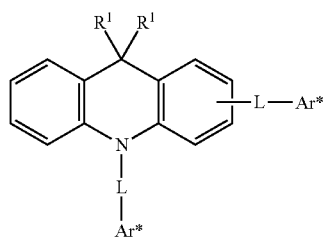

formula (I-A-1)

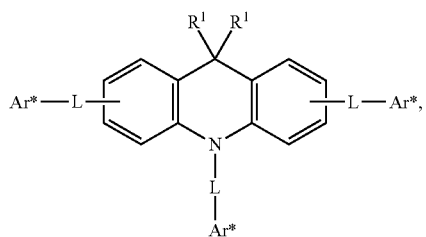

formula (I-A-2)

where the following applies to the symbols and indices occurring:

Ar* is on each occurrence, identically or differently, an aromatic ring system having 6 to 24 aromatic ring atoms selected from the formulae (A-1) to (A-20)

formula (A-1)

formula (A-2)

formula (A-3)

formula (A-4)

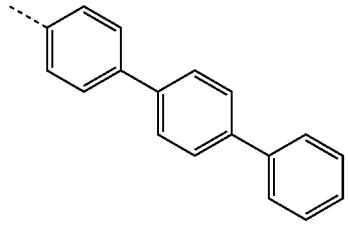

formula (A-5)

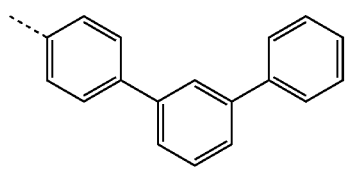

formula (A-6)

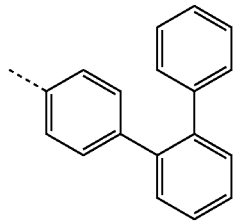

formula (A-7)

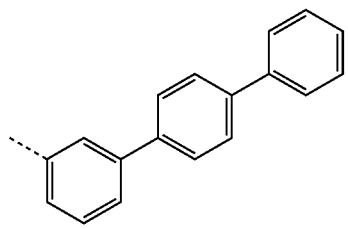

formula (A-8)

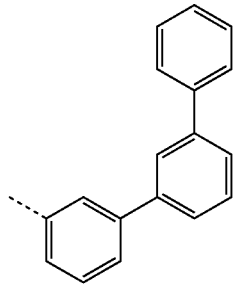

formula (A-9)

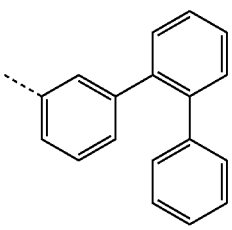

formula (A-10)

formula (A-11)

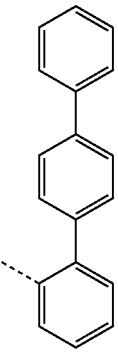

formula (A-12)

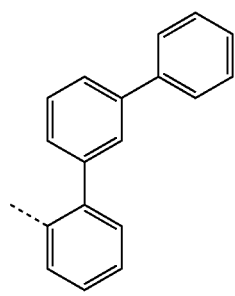

formula (A-13)

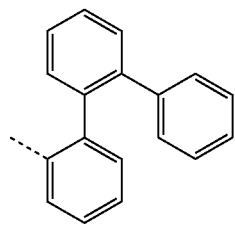

formula (A-14)

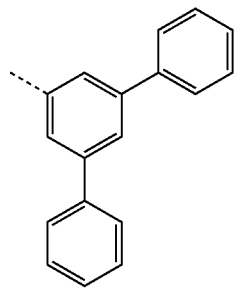

formula (A-15)

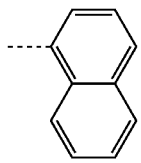

formula (A-16)

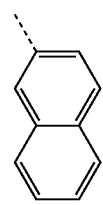

formula (A-17)

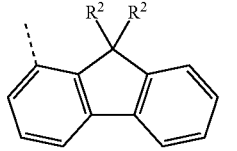

formula (A-18)

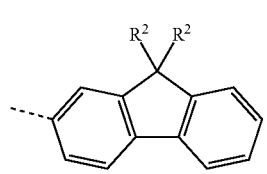

formula (A-19)

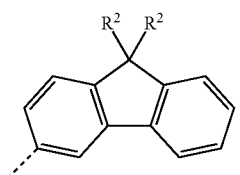

formula (A-20)

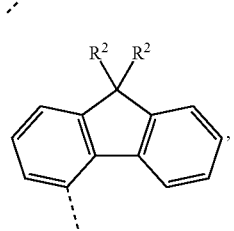

wherein $R^2$ in formulae (A-17) to (A-20), is identically or differently H, alkyl groups having 1 to 20 C atoms, or phenyl; or an electron-rich heteroaryl group having 5 to 18 aromatic ring atoms, each of which is optionally substituted by one or more radicals $R^{2'}$;

L is on each occurrence a single bond;

$R^1$ is on each occurrence, identically or differently, H, D, F, Cl, Br, I, C(=O)$R^3$, CN, Si($R^3$)$_3$, NO$_2$, P(=O)($R^3$)$_2$, S(=O)$R^3$, S(=O)$_2$$R^3$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^3$ and where one or more CH$_2$ groups in the above-mentioned groups is optionally replaced by —$R^3$C=C$R^3$—, —C≡C—, Si($R^3$)$_2$, C=O, C=S, C=N$R^3$, —C(=O)O—, —C(=O)N$R^3$—, N$R^3$, P(=O)($R^3$), —O—, —S—, SO or SO$_2$ and where one or more H atoms in the above-mentioned groups is optionally replaced by D, F, Cl, Br, I, CN or NO$_2$, or an aromatic ring system having 6 to 30 aromatic ring atoms, which may in each case be substituted by one or more radicals $R^3$, where two or more non-aromatic radicals $R^1$ is optionally linked to one another and may form a ring;

$R^{2'}$ is on each occurrence H;

$R^3$ is on each occurrence, identically or differently, H, D, F, Cl, Br, I, C(=O)$R^4$, CN, Si($R^4$)$_3$, NO$_2$, P(=O)($R^4$)$_2$, S(=O)$R^4$, S(=O)$_2$$R^4$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^4$ and where one or more CH$_2$ groups in the above-mentioned groups is optionally replaced by —$R^4$C=C$R^4$—, —C≡C—, Si(R$^4$)$_2$, C=O, C=S, C=NR$^4$, —C(=O)
O—, —C(=O)NR$^4$—, NR$^4$, P(=O)(R$^4$), —O—,
—S—, SO or SO$_2$ and where one or more H atoms in
the above-mentioned groups is optionally replaced by
D, F, Cl, Br, I, CN or NO$_2$, or an aromatic or heteroaromatic ring system having 5 to 30 aromatic ring atoms,
which may in each case be substituted by one or more
radicals R$^4$, or an aryloxy or heteroaryloxy group
having 5 to 30 aromatic ring atoms, which is optionally
substituted by one or more radicals R$^4$, where two or
more radicals R$^3$ is optionally linked to one another and
optionally forms a ring;

R$^4$ is on each occurrence, identically or differently, H, D,
F or an aliphatic, aromatic or heteroaromatic organic
radical having 1 to 20 C atoms, in which, in addition,
one or more H atoms is optionally replaced by D or F;
two or more substituents R$^4$ here is optionally linked to
one another and may form a ring;

where the compound does not contain a carbazole group;
and where at least one group Ar* which represents an electron-rich heteroaryl group having 5 to 18 aromatic ring
atoms or an aromatic ring system having 12 to 24
aromatic ring atoms must be present in the compound.

2. The compound according to claim 1, wherein
a) the group Ar* conforms to the following formula (H)

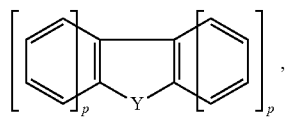

formula (H)

where
Y is NR$^2$, PR$^2$, O or S; and
p is on each occurrence equal to 0 or 1, where, for p=0,
radicals R$^2$ are bonded at the relevant positions, and
where, for Y=NR$^2$, the two indices p cannot both be
equal to 1;

the group is substituted by radicals R$^2$ at all free positions,
and the group R$^2$ is as defined in claim 1, and the group is optionally connected to the group L at any
position, where the bonding may also occur at the site
of the bond NR$^2$ or PR$^2$; or b) the group Ar* is selected from the formulae (A-1) to
(A-20)

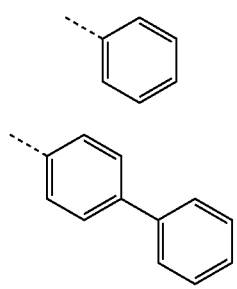

formula (A-1)

formula (A-2)

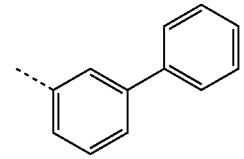

formula (A-3)

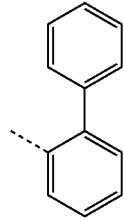

formula (A-4)

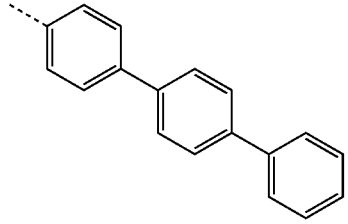

formula (A-5)

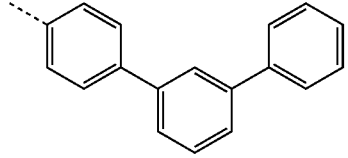

formula (A-6)

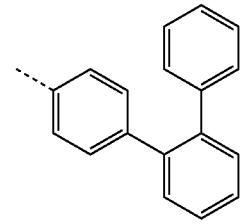

formula (A-7)

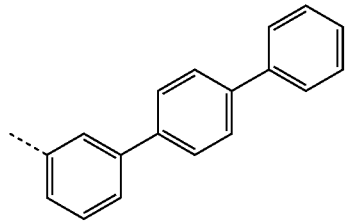

formula (A-8)

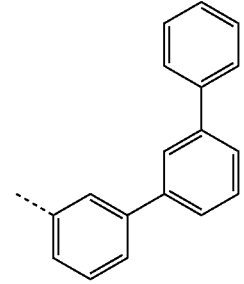

formula (A-9)

-continued formula (A-10)
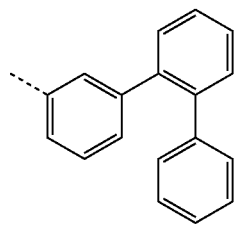

formula (A-11)
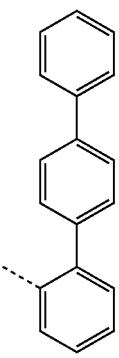

formula (A-12)
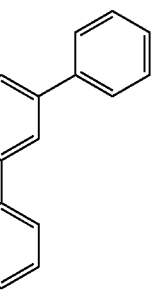

formula (A-13)
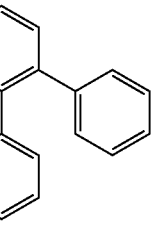

formula (A-14)
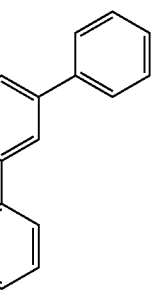

formula (A-15)
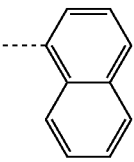

-continued formula (A-16)

formula (A-17)
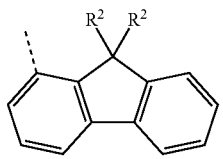

formula (A-18)
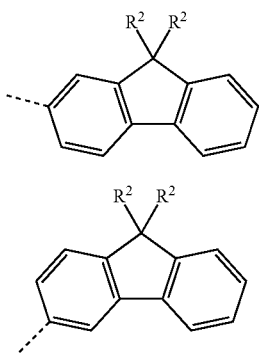

formula (A-19)
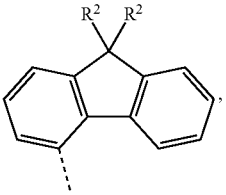

formula (A-20)
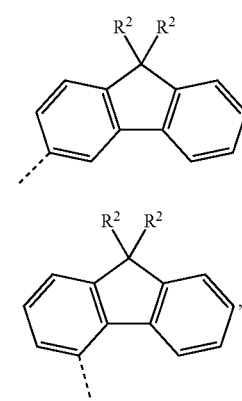

wherein $R^2$ in formulae (A-17) to (A-20), is identically or differently H, alkyl groups having 1 to 20 C atoms, or phenyl.

3. The compound according to claim 2, wherein
the group Ar* conforms to the following formula (H) and Y is O or S;
p is 1; and
the group Ar* is connected to the group L at any position.

4. The compound according to claim 3, wherein
$R^1$ is identically or differently, H, D, a straight-chain alkyl or alkoxy group having 1 to 10 C atoms or a branched or cyclic alkyl or alkoxy group having 3 to 10 C atoms, where the above-mentioned groups may each be substituted by one or more radicals $R^3$, or an aromatic ring system having 6 to 12 aromatic ring atoms, which may in each case be substituted by one or more radicals $R^3$, and $R^3$ is on each occurrence, identically or differently, H, D, F, CN, $Si(R^4)_3$ or a straight-chain alkyl or alkoxy group having 1 to 10 C atoms or a branched or cyclic alkyl or alkoxy group having 3 to 10 C atoms, where the above-mentioned groups may each be substituted by one or more radicals $R^4$, or an aromatic or heteroaromatic ring system having 5 to 18 aromatic ring atoms, which may in each case be substituted by one or more radicals $R^4$, $R^4$ is on each occurrence, identically or differently, H, D, F or an aliphatic, aromatic or heteroaromatic organic radical having 1 to 20 C atoms, in which, in addition, one or more H atoms may be replaced by D or F.

5. The compound according to claim 1, wherein the bonding position of the group L-Ar* to the aromatic six-membered ring of the basic structure of the formula (1-A-1) or formula (1-A-2) is in the para- or meta-position to the nitrogen atom.

6. The compound according to claim 1, wherein the groups $R^1$ of the group $C(R^1)_2$, do not represent an aromatic ring system and do not represent an aryl group.

7. The compound according to claim 1, wherein the compound contains no electron-deficient heteroaryl group and no keto group, no phosphorus oxide group and no sulfur oxide group.

8. A process for the preparation of the compound according to claim 1, which comprises one or more transition metal-catalysed, coupling reactions by means of which aryl or heteroaryl groups are introduced as substituents are carried out starting from a dihydroacridine derivative.

9. An oligomer, polymer or dendrimer containing one or more compounds according to claim 1, where the bond(s) to the polymer, oligomer or dendrimer is optionally localised at any position in formula (1-A-1) or formula (1-A-2) that are substituted by $R^1$ or $R^2$.

10. A formulation comprising at least one polymer, oligomer or dendrimer according to claim 9 and at least one solvent.

11. An electronic device comprising at least one polymer, oligomer or dendrimer according to claim 9.

12. A formulation comprising at least one compound according to claim 1 and at least one solvent.

13. An electronic device comprising at least one compound according to claim 1.

14. The electronic device according to claim 13, wherein the device is an organic integrated circuit, an organic field-effect transistor, an organic thin-film transistor, an organic light-emitting transistor, an organic solar cell, an organic optical detector, an organic photoreceptor, an organic field-quench device, a light-emitting electrochemical cell, an organic laser diode or an organic electroluminescent device.

15. An organic electroluminescent device which comprises the compound according to claim 1 is employed in one or more of the following functions:
   as hole-transport material in a hole-transport or hole-injection layer,
   as matrix material in an emitting layer,
   as electron-blocking material or
   as exciton-blocking material.

16. The compound according to claim 1, wherein at least one group Ar* which represents an aromatic ring system having 12 to 24 aromatic ring atoms must be present in the compound.

17. The compound according to claim 16, wherein
   $R^1$ is identically or differently, H, D, a straight-chain alkyl or alkoxy group having 1 to 10 C atoms or a branched or cyclic alkyl or alkoxy group having 3 to 10 C atoms, where the above-mentioned groups may each be substituted by one or more radicals $R^3$, or an aromatic ring system having 6 to 12 aromatic ring atoms, which may in each case be substituted by one or more radicals $R^3$, and
   $R^3$ is on each occurrence, identically or differently, H, D, F, CN, $Si(R^4)_3$ or a straight-chain alkyl or alkoxy group having 1 to 10 C atoms or a branched or cyclic alkyl or alkoxy group having 3 to 10 C atoms, where the above-mentioned groups may each be substituted by one or more radicals $R^4$, or an aromatic or heteroaromatic ring system having 5 to 18 aromatic ring atoms, which may in each case be substituted by one or more radicals $R^4$,
   $R^4$ is on each occurrence, identically or differently, H, D, F or an aliphatic, aromatic or heteroaromatic organic radical having 1 to 20 C atoms, in which, in addition, one or more H atoms may be replaced by D or F.

* * * * *